US012625149B2

(12) United States Patent
Mao

(10) Patent No.: US 12,625,149 B2
(45) Date of Patent: May 12, 2026

(54) PATHOLOGIC TDP-43 AS A BIOMARKER FOR THE DIAGNOSIS OF TDP-43 PROTEINOPATHY

(71) Applicant: UNIVERSITY OF UTAH RESEARCH FOUNDATION, Salt Lake City, UT (US)

(72) Inventor: Qinwen Mao, Salt Lake City, UT (US)

(73) Assignee: UNIVERSITY OF UTAH RESEARCH FOUNDATION, Salt Lake City, UT (US)

( * ) Notice: Subject to any disclaimer, the term of this patent is extended or adjusted under 35 U.S.C. 154(b) by 812 days.

(21) Appl. No.: 17/937,339

(22) Filed: Sep. 30, 2022

(65) Prior Publication Data

US 2023/0107901 A1      Apr. 6, 2023

Related U.S. Application Data

(60) Provisional application No. 63/252,353, filed on Oct. 5, 2021, provisional application No. 63/251,383, filed on Oct. 1, 2021.

(51) Int. Cl.
*G01N 33/68* (2006.01)

(52) U.S. Cl.
CPC . *G01N 33/6896* (2013.01); *G01N 2800/2814* (2013.01)

(58) Field of Classification Search
CPC ....... G01N 33/6896; G01N 2800/2814; G01N 2800/52; C07K 2317/30; C07K 16/18
See application file for complete search history.

(56) References Cited

U.S. PATENT DOCUMENTS

| | | | |
|---|---|---|---|
| 4,816,567 | A | 3/1989 | Cabilly et al. |
| 5,688,511 | A | 11/1997 | Gaynor et al. |
| 5,759,808 | A | 6/1998 | Casterman et al. |
| 5,800,988 | A | 9/1998 | Casterman et al. |
| 5,840,526 | A | 11/1998 | Casterman et al. |
| 5,874,541 | A | 2/1999 | Casterman et al. |
| 6,005,079 | A | 12/1999 | Casterman et al. |
| 6,015,695 | A | 1/2000 | Casterman et al. |
| 6,649,138 | B2 | 11/2003 | Adams et al. |
| 6,670,113 | B2 | 12/2003 | Hainfeld |
| 6,682,596 | B2 | 1/2004 | Zehnder et al. |
| 6,815,064 | B2 | 11/2004 | Treadway et al. |
| 7,642,064 | B2 | 1/2010 | Bieniarz et al. |
| 8,324,450 | B2 | 12/2012 | Shen et al. |
| 8,354,236 | B2 | 1/2013 | Lee et al. |
| 8,715,643 | B2 | 5/2014 | Nonaka et al. |
| 8,865,411 | B2 | 10/2014 | Gitler et al. |
| 8,889,597 | B2 | 11/2014 | Cairns et al. |
| 8,940,872 | B2 | 1/2015 | Hasegawa et al. |
| 9,044,458 | B2 | 6/2015 | Wong et al. |
| 9,128,081 | B2 | 9/2015 | Nonaka et al. |
| 9,186,356 | B2 | 11/2015 | Shen et al. |
| 9,359,363 | B2 | 6/2016 | Wolozin et al. |

| | | | |
|---|---|---|---|
| 9,441,223 | B2 | 9/2016 | Dubnau et al. |
| 9,523,128 | B2 | 12/2016 | Cairns et al. |
| 9,587,014 | B2 | 3/2017 | Nitsch et al. |
| 9,738,898 | B2 | 8/2017 | Lindquist et al. |
| 9,796,778 | B1 | 10/2017 | Chen |
| 9,844,519 | B1 | 12/2017 | Jinwal et al. |
| 9,907,804 | B2 | 3/2018 | Marshall et al. |
| 9,958,460 | B2 | 5/2018 | Goetzl |
| 10,060,933 | B2 | 8/2018 | Julien et al. |
| 10,106,803 | B2 | 10/2018 | Lindquist et al. |
| 10,191,068 | B2 | 1/2019 | Sierks et al. |
| 10,202,443 | B2 | 2/2019 | Julien et al. |
| 10,259,866 | B2 | 4/2019 | Nitsch et al. |
| 10,428,335 | B2 | 10/2019 | Lindquist et al. |
| 10,612,021 | B2 | 4/2020 | Inoue et al. |
| 10,632,169 | B2 | 4/2020 | Ko et al. |
| 10,683,544 | B2 | 6/2020 | Cairns et al. |
| 10,962,551 | B2 | 3/2021 | Wong et al. |
| 11,022,618 | B2 | 6/2021 | Sierks et al. |
| 11,028,390 | B2 | 6/2021 | Nagai et al. |
| 11,065,256 | B2 | 7/2021 | Wischik et al. |
| 11,066,669 | B2 | 7/2021 | Hagedorn et al. |
| 11,091,540 | B2 | 8/2021 | Nitsch et al. |

(Continued)

FOREIGN PATENT DOCUMENTS

| | | |
|---|---|---|
| EP | 0173494 A2 | 3/1986 |
| EP | 0184187 A2 | 6/1986 |

(Continued)

OTHER PUBLICATIONS

Arai T, et al. TDP-43 is a component of ubiquitin-positive tau-negative inclusions in frontotemporal lobar degeneration and amyotrophic lateral sclerosis. Biochem Biophys Res Commun. 2006;351(3):602-11.

Armakola, M. et al. "TDP-43 toxicity in yeast." Methods 53.3 (2011): 238-245.

Attems, J. et al. "Neuropathological correlates of cerebral multimorbidity." Current Alzheimer Research 10.6 (2013): 569-577.

Baldwin, G. C., et al. "Granulocyte-macrophage colony-stimulating factor enhances neutrophil function in acquired Immunodeficiency syndrome patients." Proceedings of the National Academy of Sciences 85.8 (1988): 2763-2766.

(Continued)

*Primary Examiner* — Olga N Chernyshev
(74) *Attorney, Agent, or Firm* — Michael Best & Friedrich LLP

(57) ABSTRACT

Disclosed herein are antibodies or antigen-binding fragments thereof and compositions comprising the same. Also disclosed are methods of detecting TAR DNA-binding protein 43 (TDP-43) in a biological sample, diagnosing a neurodegenerative disease in a subject, and selecting whether to enroll a subject in a clinical trial for frontotemporal lobar degeneration with TDP-43 inclusions (FTLD-TDP) using the antibodies or antigen-binding fragments thereof described herein. In addition, disclosed herein are immunoassay kits for selectively detecting TDP-43 in a biological sample.

8 Claims, 10 Drawing Sheets

Specification includes a Sequence Listing.

(56) References Cited

U.S. PATENT DOCUMENTS

| | | |
|---|---|---|
| 2004/0265307 A1 | 12/2004 | Singh et al. |
| 2004/0265922 A1 | 12/2004 | Bieniarz et al. |
| 2009/0263824 A1 | 10/2009 | Lee et al. |
| 2010/0136573 A1 | 6/2010 | Petrucelli et al. |
| 2010/0306862 A1 | 12/2010 | Shen et al. |
| 2010/0332417 A1 | 12/2010 | Bacus |
| 2011/0034447 A1 | 2/2011 | Nonaka et al. |
| 2011/0053857 A1 | 3/2011 | Lindquist et al. |
| 2011/0065600 A1 | 3/2011 | Cairns et al. |
| 2011/0142789 A1 | 6/2011 | Gitler et al. |
| 2011/0203007 A1 | 8/2011 | Klein et al. |
| 2011/0287453 A1 | 11/2011 | Hasegawa et al. |
| 2012/0178775 A1 | 7/2012 | Shen et al. |
| 2012/0237499 A1 | 9/2012 | Gitler et al. |
| 2012/0291146 A1 | 11/2012 | Klein et al. |
| 2013/0022544 A1 | 1/2013 | Wisniewski et al. |
| 2013/0059757 A1 | 3/2013 | Gitler |
| 2013/0184441 A1 | 7/2013 | Lee et al. |
| 2013/0219534 A1 | 8/2013 | Wong et al. |
| 2014/0080780 A1 | 3/2014 | Wolozin |
| 2014/0099660 A1 | 4/2014 | Nonaka et al. |
| 2014/0113952 A1 | 4/2014 | Dubnau et al. |
| 2014/0120562 A1 | 5/2014 | Julien et al. |
| 2014/0255304 A1 | 9/2014 | Roger et al. |
| 2015/0045248 A1 | 2/2015 | Takahashi et al. |
| 2015/0065384 A1 | 3/2015 | Cairns et al. |
| 2015/0087653 A1 | 3/2015 | Moussa |
| 2015/0111777 A1 | 4/2015 | Agbas |
| 2015/0119278 A1 | 4/2015 | Goetzl |
| 2015/0173330 A1 | 6/2015 | Okano et al. |
| 2015/0252424 A1 | 9/2015 | Gitler |
| 2015/0352232 A1 | 12/2015 | Tooyama et al. |
| 2016/0091504 A1 | 3/2016 | Julien et al. |
| 2016/0161481 A1 | 6/2016 | Willbold et al. |
| 2016/0291037 A1 | 10/2016 | Sierks et al. |
| 2017/0010284 A1 | 1/2017 | Sierks et al. |
| 2017/0067112 A1 | 3/2017 | Cairns et al. |
| 2017/0088515 A1 | 3/2017 | Wolozin et al. |
| 2017/0121770 A1 | 5/2017 | Dubnau et al. |
| 2017/0146555 A1 | 5/2017 | Wang et al. |
| 2017/0152308 A1 | 6/2017 | Nitsch et al. |
| 2017/0226508 A1 | 8/2017 | Inoue et al. |
| 2017/0298124 A1 | 10/2017 | Chen |
| 2017/0321222 A1 | 11/2017 | Lindquist et al. |
| 2017/0355756 A1 | 12/2017 | Julien et al. |
| 2017/0360726 A1 | 12/2017 | Larsen et al. |
| 2017/0360805 A1 | 12/2017 | Chen et al. |
| 2017/0369474 A1 | 12/2017 | Larsen et al. |
| 2018/0080945 A1 | 3/2018 | Goetzl |
| 2018/0217165 A1 | 8/2018 | Goetzl |
| 2018/0306810 A1 | 10/2018 | Ayala |
| 2018/0372756 A1 | 12/2018 | Wong et al. |
| 2019/0010507 A1 | 1/2019 | Lindquist et al. |
| 2019/0015395 A1 | 1/2019 | Appleford et al. |
| 2019/0029977 A1 | 1/2019 | Zankel et al. |
| 2019/0211070 A1 | 7/2019 | Wang |
| 2019/0241890 A1 | 8/2019 | Iversen |
| 2019/0250171 A1 | 8/2019 | Sierks et al. |
| 2019/0315798 A1 | 10/2019 | Shaw et al. |
| 2019/0335727 A1 | 11/2019 | Shen et al. |
| 2019/0338004 A1 | 11/2019 | Wisniewski et al. |
| 2019/0350902 A1 | 11/2019 | Njardarson et al. |
| 2019/0365795 A1 | 12/2019 | Hagedorn et al. |
| 2019/0388397 A1 | 12/2019 | Aron et al. |
| 2020/0016165 A1 | 1/2020 | Wischik et al. |
| 2020/0017577 A1 | 1/2020 | Nitsch et al. |
| 2020/0024600 A1 | 1/2020 | Hagedorn et al. |
| 2020/0093828 A1 | 3/2020 | Martinez Gil et al. |
| 2020/0095296 A1 | 3/2020 | Sulzer et al. |
| 2020/0165327 A1 | 5/2020 | Plotkin et al. |
| 2020/0165610 A1 | 5/2020 | Nagai et al. |
| 2020/0325168 A9 | 10/2020 | Shaw et al. |
| 2020/0330497 A1 | 10/2020 | Marcotulli et al. |
| 2020/0404890 A1 | 12/2020 | Sharma-kanning et al. |
| 2021/0023062 A1 | 1/2021 | Keefe et al. |
| 2021/0024621 A1 | 1/2021 | Urushitani et al. |
| 2021/0024925 A1 | 1/2021 | Hagedorn et al. |
| 2021/0121438 A1 | 4/2021 | Chang et al. |
| 2021/0139547 A1 | 5/2021 | Donnelly et al. |
| 2021/0169914 A1 | 6/2021 | Donnelly et al. |
| 2021/0238590 A1 | 8/2021 | Pulst et al. |
| 2021/0270843 A1 | 9/2021 | Fowler |

FOREIGN PATENT DOCUMENTS

| | | |
|---|---|---|
| EP | 0125023 B1 | 6/1991 |
| EP | 0171496 B1 | 5/1993 |
| WO | 1986001533 A1 | 3/1986 |
| WO | 1987002671 A1 | 5/1987 |
| WO | 2003106621 A2 | 12/2003 |
| WO | 2005003777 A2 | 1/2005 |
| WO | 2008042190 A2 | 4/2008 |
| WO | 2008151055 A1 | 12/2008 |
| WO | 2009008529 A1 | 1/2009 |
| WO | 2009027105 A2 | 3/2009 |
| WO | 2009044119 A1 | 4/2009 |
| WO | 2009099941 A2 | 8/2009 |
| WO | 2009102995 A1 | 8/2009 |
| WO | 2009125646 A1 | 10/2009 |
| WO | 2010000372 A2 | 1/2010 |
| WO | 2010015040 A1 | 2/2010 |
| WO | 2010022140 A1 | 2/2010 |
| WO | 2010053788 A1 | 5/2010 |
| WO | 2010065878 A1 | 6/2010 |
| WO | 2010111587 A1 | 9/2010 |
| WO | 2011005628 A1 | 1/2011 |
| WO | 2011057029 A1 | 5/2011 |
| WO | 2011094545 A2 | 8/2011 |
| WO | 2011109503 A1 | 9/2011 |
| WO | 2011123388 A1 | 10/2011 |
| WO | 2012004276 A2 | 1/2012 |
| WO | 2012012712 A2 | 1/2012 |
| WO | 2012021287 A2 | 2/2012 |
| WO | 2012045451 A1 | 4/2012 |
| WO | 2012103577 A1 | 8/2012 |
| WO | 2012162249 A1 | 11/2012 |
| WO | 2012174666 A1 | 12/2012 |
| WO | 2013012811 A2 | 1/2013 |
| WO | 2013061163 A2 | 2/2013 |
| WO | 2013061161 A2 | 5/2013 |
| WO | 2013064934 A1 | 5/2013 |
| WO | 2013078395 A1 | 5/2013 |
| WO | 2013082307 A1 | 6/2013 |
| WO | 2013112651 A2 | 8/2013 |
| WO | 2013112699 A2 | 8/2013 |
| WO | 2013112706 A2 | 8/2013 |
| WO | 2013166295 A1 | 11/2013 |
| WO | 2013169793 A2 | 11/2013 |
| WO | 2013180214 A1 | 12/2013 |
| WO | 2014039696 A2 | 3/2014 |
| WO | 2014109296 A1 | 7/2014 |
| WO | 2014125121 A1 | 8/2014 |
| WO | 2014132053 A1 | 9/2014 |
| WO | 2014145975 A2 | 9/2014 |
| WO | 2014161890 A1 | 10/2014 |
| WO | 2014207049 A2 | 12/2014 |
| WO | 2015048100 A1 | 4/2015 |
| WO | 2015059632 A1 | 4/2015 |
| WO | 2015061634 A2 | 4/2015 |
| WO | 2015066211 A1 | 5/2015 |
| WO | 2015077780 A1 | 5/2015 |
| WO | 2015117088 A2 | 8/2015 |
| WO | 2015143300 A1 | 9/2015 |
| WO | 2015152724 A2 | 10/2015 |
| WO | 2015157390 A1 | 10/2015 |
| WO | 2015158924 A1 | 10/2015 |
| WO | 2015200434 A1 | 12/2015 |
| WO | 2016014908 A1 | 1/2016 |
| WO | 2016023019 A2 | 2/2016 |
| WO | 2016053610 A1 | 4/2016 |
| WO | 2016059144 A1 | 4/2016 |
| WO | 2016077595 A1 | 5/2016 |
| WO | 2016086320 A1 | 6/2016 |
| WO | 2016090313 A1 | 6/2016 |

(56)         References Cited

FOREIGN PATENT DOCUMENTS

| | | | |
|---|---|---|---|
| WO | 2016090317 A1 | 6/2016 |
| WO | 2016176558 A1 | 11/2016 |
| WO | 2016201388 A2 | 12/2016 |
| WO | 2016201389 A2 | 12/2016 |
| WO | 2016205522 A2 | 12/2016 |
| WO | 2016205615 A1 | 12/2016 |
| WO | 2016210123 A1 | 12/2016 |
| WO | 2017040301 A1 | 3/2017 |
| WO | 2017066705 A1 | 4/2017 |
| WO | 2017075432 A2 | 5/2017 |
| WO | 2017102893 A1 | 6/2017 |
| WO | 2017118857 A1 | 7/2017 |
| WO | 2017152102 A2 | 9/2017 |
| WO | 2017157961 A1 | 9/2017 |
| WO | 2017173451 A1 | 10/2017 |
| WO | 2017177178 A1 | 10/2017 |
| WO | 2017180904 A1 | 10/2017 |
| WO | 2017180911 A1 | 10/2017 |
| WO | 2017193115 A1 | 11/2017 |
| WO | 2017218815 A1 | 12/2017 |
| WO | 2018006092 A1 | 1/2018 |
| WO | 2018018031 A1 | 1/2018 |
| WO | 2018019823 A1 | 2/2018 |
| WO | 2018022479 A1 | 2/2018 |
| WO | 2018081878 A1 | 5/2018 |
| WO | 2018107058 A1 | 6/2018 |
| WO | 2018119395 A1 | 6/2018 |
| WO | 2018140657 A1 | 8/2018 |
| WO | 2018165293 A1 | 9/2018 |
| WO | 2018172587 A1 | 9/2018 |
| WO | 2018187240 A1 | 10/2018 |
| WO | 2018195075 A1 | 10/2018 |
| WO | 2018200527 A1 | 11/2018 |
| WO | 2018204854 A1 | 11/2018 |
| WO | 2018213316 A1 | 11/2018 |
| WO | 2018215597 A1 | 11/2018 |
| WO | 2018215831 A2 | 11/2018 |
| WO | 2018218219 A1 | 11/2018 |
| WO | 2018218352 A1 | 12/2018 |
| WO | 2018226590 A1 | 12/2018 |
| WO | 2018231415 A1 | 12/2018 |
| WO | 2018236986 A1 | 12/2018 |
| WO | 2019028292 A1 | 2/2019 |
| WO | 2019032613 A1 | 2/2019 |
| WO | 2019079626 A1 | 4/2019 |
| WO | 2019079686 A1 | 4/2019 |
| WO | 2019084497 A1 | 5/2019 |
| WO | 2019113711 A1 | 6/2019 |
| WO | 2019133512 A1 | 7/2019 |
| WO | 2019134981 A1 | 7/2019 |
| WO | 2019144056 A1 | 7/2019 |
| WO | 2019152706 A1 | 8/2019 |
| WO | 2019152715 A1 | 8/2019 |
| WO | 2019152781 A1 | 8/2019 |
| WO | 2019157440 A1 | 8/2019 |
| WO | 2019177138 A1 | 9/2019 |
| WO | 2019178313 A1 | 9/2019 |
| WO | 2019191332 A1 | 10/2019 |
| WO | 2019211253 A1 | 11/2019 |
| WO | 2019226973 A1 | 11/2019 |
| WO | 2019233921 A1 | 12/2019 |
| WO | 2019233922 A1 | 12/2019 |
| WO | 2019241734 A1 | 12/2019 |
| WO | 2019246071 A1 | 12/2019 |
| WO | 2019246494 A1 | 12/2019 |
| WO | 2020006325 A1 | 1/2020 |
| WO | 2020006374 A2 | 1/2020 |
| WO | 2020006630 A1 | 1/2020 |
| WO | 2020020751 A1 | 1/2020 |
| WO | 2020023417 A1 | 1/2020 |
| WO | 2020027311 A1 | 2/2020 |
| WO | 2020028060 A1 | 2/2020 |
| WO | 2020028751 A2 | 2/2020 |
| WO | 2020037234 A1 | 2/2020 |
| WO | 2020047374 A1 | 3/2020 |
| WO | 2020058558 A1 | 3/2020 |
| WO | 2020081973 A1 | 4/2020 |
| WO | 2020087126 A1 | 5/2020 |
| WO | 2020093035 A1 | 5/2020 |
| WO | 2020117877 A1 | 6/2020 |
| WO | 2020118458 A1 | 6/2020 |
| WO | 2020124013 A1 | 6/2020 |
| WO | 2020150290 A2 | 7/2020 |
| WO | 2020150545 A1 | 7/2020 |
| WO | 2020157705 A1 | 8/2020 |
| WO | 2020163794 A1 | 8/2020 |
| WO | 2020190866 A1 | 9/2020 |
| WO | 2020201167 A1 | 10/2020 |
| WO | 2020201339 A1 | 10/2020 |
| WO | 2020210634 A1 | 10/2020 |
| WO | 2020230106 A1 | 11/2020 |
| WO | 2020234473 A1 | 11/2020 |
| WO | 2020247419 A2 | 12/2020 |
| WO | 2020247825 A1 | 12/2020 |
| WO | 2020247873 A1 | 12/2020 |
| WO | 2020252394 A2 | 12/2020 |
| WO | 2020254697 A1 | 12/2020 |
| WO | 2020257631 A2 | 12/2020 |
| WO | 2020264339 A1 | 12/2020 |
| WO | 2021016462 A1 | 1/2021 |
| WO | 2021022083 A2 | 2/2021 |
| WO | 2021025995 A1 | 2/2021 |
| WO | 2021026601 A1 | 2/2021 |
| WO | 2021030257 A1 | 2/2021 |
| WO | 2021030678 A1 | 2/2021 |
| WO | 2021035101 A1 | 2/2021 |
| WO | 2021048440 A1 | 3/2021 |
| WO | 2021055502 A1 | 3/2021 |
| WO | 2021077162 A1 | 4/2021 |
| WO | 2021081272 A1 | 4/2021 |
| WO | 2021110995 A1 | 6/2021 |
| WO | 2021113921 A1 | 6/2021 |
| WO | 2021126320 A1 | 6/2021 |
| WO | 2021127303 A1 | 6/2021 |
| WO | 2021133907 A1 | 7/2021 |
| WO | 2021146438 A1 | 7/2021 |
| WO | 2021150840 A1 | 7/2021 |
| WO | 2021155190 A1 | 8/2021 |
| WO | 2021159008 A2 | 8/2021 |
| WO | 2021194608 A1 | 9/2021 |
| WO | 2021195446 A2 | 9/2021 |
| WO | 2022034228 A1 | 2/2022 |
| WO | 2022189558 A2 | 9/2022 |

OTHER PUBLICATIONS

Begley DJ, et al. Structural and functional aspects of the blood-brain barrier. Prog Drug Res. 2003;61:39-78.

Berning BA, et al. The Pathobiology of TDP-43 C-Terminal Fragments in ALS and FTLD. Front Neurosci. 2019;13:335.

Better, M., et al. "*Escherichia coli* secretion of an active chimeric antibody fragment." Science 240.4855 (1988): 1041-1043.

Bird, R. E., et al. "Single-chain antigen-binding proteins." Science 242.4877 (1988): 423-426.

Blennow K, et al. Clinical utility of cerebrospinal fluid biomarkers in the diagnosis of early Alzheimer's disease. Alzheimers Dement. 2015;11(1):58-69.

Buratti E, et al. Multiple roles of TDP-43 in gene expression, splicing regulation, and human disease. Front Biosci. 2008;13:867-78.

Butko MT et al. (2013) In vivo quantitative proteomics of somatosensory cortical synapses shows which protein levels are modulated by sensory deprivation. Proc Natl Acad Sci USA. (Track I) 110 (8) E726-E735.

Cairns NJ, et al. TDP-43 in familial and sporadic frontotemporal lobar degeneration with ubiquitin inclusions. Am J Pathol. 2007;171(1):227-40.

Cairns, N. J., et al. "Neuropathologic diagnostic and nosologic criteria for frontotemporal lobar degeneration: consensus of the Consortium for Frontotemporal Lobar Degeneration." Acta neuropathologica 114.1 (2007): 5-22.

(56) References Cited

OTHER PUBLICATIONS

Cashman, N. R., et al. "Targeting of misfolded, pathogenic TDP-43 with rationally designed antibodies: Nonhuman/Target identification and validation studies: Proteostasis." Alzheimer's & Dementia 16 (2020): e045221 (2 pages).

Cherry, J. Michael. "Computer manipulation of DNA and protein sequences." Current Protocols in Molecular Biology 30.1 (1995): 7.7.1-7.7.23, including section 7.7.18, Table 7.7.1.

Conklin HM, et al. (2015). Computerized Cognitive Training for Amelioration of Cognitive Late Effects among Childhood Cancer Survivors: A Randomized Controlled Trial. Journal of Clinical Oncology, 33:3894-3902.

Constantine NT, et al. Enhanced chemiluminescence as a means of increasing the sensitivity of western blot assays for HIV antibody. J Virol Methods. 1994;47(1-2):153-64.

Culver BP, et al. Proteomic analysis of wild-type and mutant huntingtin-associated proteins in mouse brains identifies unique interactions and involvement in protein synthesis. J Biol Chem. 2012;287(26):21599-614.

De Wit J, et al. (2013) Unbiased Discovery of Glypican as a Novel Receptor for LRRTM4 in Regulating Excitatory Synapse Development. Neuron. 79(4): 696-711.

Feneberg, E., et al. "Towards a TDP-43-based biomarker for ALS and FTLD." Molecular neurobiology 55.10 (2018): 7789-7801.

Fonslow BR, Yates JR. 3.12—Proteolytic Digestion Methods for Shotgun Proteomics. In: Pawliszyn J, editor. Comprehensive Sampling and Sample Preparation. Oxford: Academic Press; 2012. p. 261-76.

Forman MS, et al. Frontotemporal dementia: clinicopathological correlations. Ann Neurol. 2006;59(6):952-62.

Fuentealba RA, et al. Interaction with polyglutamine aggregates reveals a Q/N-rich domain in TDP-43. J Biol Chem. 2010;285(34):26304-14.

Gefen T, et al. Combined Pathologies in FTLD-TDP Types A and C. J Neuropathol Exp Neurol. 2018;77(5):405-12.

Gendron TF, et al. Review: transactive response DNA-binding protein 43 (TDP-43): mechanisms of neurodegeneration. Neuropathol Appl Neurobiol. 2010;36(2):97-112.

Geyer PE, et al. Revisiting biomarker discovery by plasma proteomics. Mol Syst Biol. 2017;13(9):942.

Goossens, J., et al. "TDP-43 as a possible biomarker for frontotemporal lobar degeneration: a systematic review of existing antibodies." Acta neuropathologica communications 3.1 (2015): 1-8.

Hanley, J. A., et al. "The meaning and use of the area under a receiver operating characteristic (ROC) curve." Radiology 143.1 (1982): 29-36.

Hark, T. J., et al. "Pulse-chase proteomics of the App knockin mouse models of Alzheimer's disease reveals that synaptic dysfunction originates in presynaptic terminals." Cell systems 12.2 (2021): 141-158.

Hashimoto-Gotoh, T., et al. "An oligodeoxyribonucleotide-directed dual amber method for site-directed mutagenesis." Gene 152.2 (1995): 271-275.

He, Q., et al. "Critical period inhibition of NKCC1 rectifies synapse plasticity in the somatosensory cortex and restores adult tactile response maps in fragile X mice." Molecular psychiatry 24.11 (2019): 1732-1747.

Hickox AE, et al. (2016) Global Analysis of Protein Expression of Inner Ear Hair Cells. J Neurosci. 2016 1320-1339.

Hultschig, C., et al. "Recent advances of protein microarrays." Current opinion in chemical biology 10.1 (2006): 4-10.

Huston, J. S., et al. "Protein engineering of antibody binding sites: recovery of specific activity in an anti-digoxin single-chain Fv analogue produced in *Escherichia coli*." Proceedings of the National Academy of Sciences 85.16 (1988): 5879-5883.

Hyman, B. T., et al. "National Institute on Aging-Alzheimer's Association guidelines for the neuropathologic assessment of Alzheimer's disease." Alzheimer's & dementia 8.1 (2012): 1-13.

Jara JH, et al. MCP1-CCR2 and neuroinflammation in the ALS motor cortex with TDP-43 pathology. J Neuroinflammation. 2019;16(1):196.

Jeong H, et al. (2009) Acetylation targets mutant Huntingtin to autophagosomes for degradation. Cell. 137(1):60-72.

Jha S, et al. Trans-kingdom mimicry underlies ribosome customization by a poxvirus kinase. Nature. 2017;546 (7660):651-5.

Jongkamonwiwat, N., et al. "Noise exposures causing hearing loss generate proteotoxic stress and activate the proteostasis network." Cell reports 33.8 (2020): 108431.

Jucker, M. et al. "Pathogenic protein seeding in Alzheimer disease and other neurodegenerative disorders." Annals of neurology 70.4 (2011): 532-540.

Kametani F, et al. Identification of casein kinase-1 phosphorylation sites on TDP-43. Biochem Biophys Res Commun. 2009;382(2):405-9.

Kametani F, et al. Mass spectrometric analysis of accumulated TDP-43 in amyotrophic lateral sclerosis brains. Sci Rep. 2016;6:23281.

Kawles, A., et al. "Cortical and subcortical pathological burden and neuronal loss in an autopsy series of FTLD-TDP-type C." Brain 145.3 (2022): 1069-1078.

Kim, E.-J., et al. "Mixed TDP-43 proteinopathy and tauopathy in frontotemporal lobar degeneration: nine case series." Journal of neurology 265. 12 (2018): 2960-2971.

Kirk-Othmer, Encyclopedia of chemical technology, 4th ed., executive editor, J. I. Kroschwitz; editor, M Howe-Grant, John Wiley & Sons, 1993, vol. 15, p. 518-562.

Kramer, W. et al. "[18] Oligonucleotide-directed construction of mutations via gapped duplex DNA." Methods in enzymology. vol. 154. Academic Press, 1987. 350-367.

Kramer, W., et al. "The gapped duplex DNA approach to oligonucleotide-directed mutation construction." Nucleic acids research 12.24 (1984): 9441-9456.

Kuhle J, et al. Comparison of three analytical platforms for quantification of the neurofilament light chain in blood samples: ELISA, electrochemiluminescence immunoassay and Simoa. Clin Chem Lab Med. 2016;54(10):1655-61.

Kuhle J, et al. Serum neurofilament light chain in early relapsing remitting MS is increased and correlates with CSF levels and with MRI measures of disease severity. Mult Scler. 2016;22(12):1550-9.

Kunkel, T. A. "Rapid and efficient site-specific mutagenesis without phenotypic selection." Proceedings of the National Academy of Sciences 82.2 (1985): 488-492.

International Search Report and Written Opinion for Application No. PCT/US2022/077410 dated Feb. 7, 2023 (21 pages).

Kwong, L. K., et al. "Novel monoclonal antibodies to normal and pathologically altered human TDP-43 proteins." Acta neuropathologica communications 2.1 (2014): 1-9.

Kyte, J. et al. "A simple method for displaying the hydropathic character of a protein." Journal of molecular biology 157.1 (1982): 105-132.

Li Y, et al. A Highly Sensitive Sandwich ELISA to Detect CSF Progranulin: A Potential Biomarker for CNS Disorders. J Neuropathol Exp Neurol. 2019;78(5):406-15.

Li Y, et al. Biological function analysis of monoclonal antibodies against human granulins in vitro using U251 cells as a model. Protein Expr Purif. Feb. 2017;130:55-62.

Li Y, et al. Generation of a novel HEK293 luciferase reporter cell line by CRISPR/Cas9-mediated site-specific integration in the genome to explore the transcriptional regulation of the PGRN gene. Bioengineered. 2019;10(1):98-107.

Li, W., et al. "Heat shock-induced phosphorylation of TAR DNA-binding protein 43 (TDP-43) by MAPK/ERK kinase regulates TDP-43 function." Journal of Biological Chemistry 292.12 (2017): 5089-5100.

Lin, P.-Y., et al. "Overexpression of heat shock factor 1 maintains TAR DNA binding protein 43 solubility via induction of inducible heat shock protein 70 in cultured cells." Journal of neuroscience research 94.7 (2016): 671-682.

Ling SC, et al. Converging mechanisms in ALS and FTD: disrupted RNA and protein homeostasis. Neuron. 2013;79(3):416-38.

(56)                     References Cited

OTHER PUBLICATIONS

Liu, A. Y., et al. "Chimeric mouse-human IgG1 antibody that can mediate lysis of cancer cells." Proceedings of the National Academy of Sciences 84.10 (1987): 3439-3443.

Liu, A. Y., et al. "Production of a mouse-human chimeric monoclonal antibody to CD20 with potent Fc-dependent biologic activity." The Journal of Immunology 139.10 (1987): 3521-3526.

Mackenzie IR, et al. Nomenclature and nosology for neuropathologic subtypes of frontotemporal lobar degeneration: an update. Acta Neuropathol. 2010;119(1):1-4.

Mackenzie IR, et al. Nomenclature for neuropathologic subtypes of frontotemporal lobar degeneration: consensus recommendations. Acta Neuropathol. 2009;117(1):15-8.

Mackenzie IR, et al. TDP-43 and FUS in amyotrophic lateral sclerosis and frontotemporal dementia. Lancet Neurol. 2010;9(10):995-1007.

Mao Q. et al. Disease and Region Specificity of Granulin Immunopositivities in Alzheimer Disease and Frontotemporal Lobar Degeneration. J Neuropathol Exp Neurol. Nov. 1, 2017;76(11):957-968.

Mao Q. et al. FTLD-TDP With and Without GRN Mutations Cause Different Patterns of CA1 Pathology. J Neuropathol Exp Neurol. 2019;78(9):844-53.

McKhann GM, et al. Clinical and pathological diagnosis of frontotemporal dementia: report of the Work Group on Frontotemporal Dementia and Pick's Disease. Arch Neurol. 2001;58(11):1803-9.

Miki, Y., et al. "Accumulation of the sigma-1 receptor is common to neuronal nuclear inclusions in various neurodegenerative diseases." Neuropathology 34.2 (2014): 148-158.

Montine TJ, et al. National Institute on Aging-Alzheimer's Association guidelines for the neuropathologic assessment of Alzheimer's disease: a practical approach. Acta Neuropathol. 2012;123(1):1-11.

Neumann, M., et al. "TDP-43 proteinopathy in frontotemporal lobar degeneration and amyotrophic lateral sclerosis: protein misfolding diseases without amyloidosis." Archives of neurology 64.10 (2007): 1388-1394.

Neumann, M., et al. "Ubiquitinated TDP-43 in frontotemporal lobar degeneration and amyotrophic lateral sclerosis." Science 314.5796 (2006): 130-133.

Ng, JSW, et al. "Using tetracysteine-tagged TDP-43 with a biarsenical dye to monitor real-time trafficking in a cell model of amyotrophic lateral sclerosis." Biochemistry 58.39 (2019): 4086-4095.

Nishihira Y, et al. Revisiting the utility of TDP-43 immunoreactive (TDP-43-ir) pathology to classify FTLD-TDP subtypes. Acta Neuropathol. 2019;138(1):167-9.

Nishimoto, Y., et al. "Characterization of alternative isoforms and inclusion body of the TAR DNA-binding protein-43." Journal of Biological Chemistry 285.1 (2010): 608-619.

Nishimura, Y., et al. "Recombinant human-mouse chimeric monoclonal antibody specific for common acute lymphocytic leukemia antigen." Cancer research 47.4 (1987): 999-1005.

O'Sullivan ML et al. (2012) Postsynaptic FLRT proteins are endogenous ligands for the black widow spider venom receptor Latrophilin and regulate excitatory synapse development and function. Neuron. 73(5):903-10.

Park, S. K., et al. "A quantitative analysis software tool for mass spectrometry-based proteomics." Nature methods 5.4 (2008): 319-322.

Park, SKR, et al. "Census 2: isobaric labeling data analysis." Bioinformatics 30.15 (2014): 2208-2209.

Pesiridis, G. S., et al. "A 'two-hit' hypothesis for inclusion formation by carboxyl-terminal fragments of TDP-43 protein inked to RNA depletion and impaired microtubule-dependent transport." Journal of Biological Chemistry 286.21 (2011): 18845-18855.

Pham E, et al. (2010) Progressive accumulation of Abeta oligomers in the brains of patients with Alzheimer's disease is associated with selective alterations in synaptic scaffold proteins. FEBS J. 277(14):3051-67.

Pounds S.B., et al. (2012). Empirical Bayesian Selection of Hypothesis Testing Procedures for Analysis of Sequence Count Expression Data. Statistical Applications in Genetics and Molecular Biology, 11(5), article 7.

Rascovsky K, et al. Sensitivity of revised diagnostic criteria for the behavioural variant of frontotemporal dementia. Brain. 2011;134(Pt 9):2456-77.

Ratnavalli E, et al. The prevalence of frontotemporal dementia. Neurology. 2002;58(11):1615-21.

Rogalski E, et al. Cognitive trajectories and spectrum of neuropathology in SuperAgers: The first 10 cases. Hippocampus. 2019;29(5):458-67.

Rosso SM, et al. Frontotemporal dementia in The Netherlands: patient characteristics and prevalence estimates from a population-based study. Brain. 2003; 126(Pt 9):2016-22.

Savas JN et al. (2008) Huntington's disease protein contributes to RNAi through association with Argonaute and P-bodies. Proc Natl Acad Sci USA. (Track II) 105(31):10820-25.

Savas JN et al. (2010) A role for Huntington's disease protein in dendritic neuronal RNA granules. J Biol Chem. 285(17):13142-53.

Savas JN et al. (2012) Extremely long-lived nuclear pore proteins in the rat brain. Science. 24;335(6071):942.

Savas JN et al. (2014) Ecto-Fc MS identifies ligand-receptor interactions through extracellular domain Fc fusion protein baits and shotgun proteomic analysis. Nat Protocols. 9(9):2061-74.

Savas JN et al. (2015) Proteomic analysis of protein turnover by metabolic whole rodent pulse-chase isotopic labeling and shotgun mass spectrometry analysis. Methods Mol Biol. 1410:293-304.

Savas JN et al. (2015) The Sorting Receptor SorCS1 Regulates Trafficking of Neurexin and AMPA Receptors. Neuron. 19;87(4):764-80.

Savas JN et al. (2017) Amyloid accumulation drives proteome-wide alterations in mouse models of Alzheimer's disease like pathology. Cell Rep. 21(9):2614-2627.

Scialò, C., et al. "TDP-43 real-time quaking induced conversion reaction optimization and detection of seeding activity in CSF of amyotrophic lateral sclerosis and frontotemporal dementia patients." Brain communications 2.2 (2020): fcaa142.

Shanks NF et al. (2012) Differences in AMPA and kainate receptor interactomes facilitate identification of AMPA receptor auxiliary subunit GSG1L. Cell Rep. 28;1(6):590-8.

Shanks NF et al. Molecular dissection of the interaction between the AMPA receptor and cornichon homolog-3. J Neurosci. 2014;34(36):12104-20.

Shaw, D. R., et al. "Mouse/human chimeric antibodies to a tumor-associated antigen: biologic activity of the four human IgG subclasses." JNCI: Journal of the National Cancer Institute 80.19 (1988): 1553-1559.

Shevchenko A, et al. In-gel digestion for mass spectrometric characterization of proteins and proteomes. Nat Protoc. 2006;1(6):2856-60.

Shodai, A., et al. "Conserved acidic amino acid residues in a second RNA recognition motif regulate assembly and function of TDP-43." PloS one 7.12 (2012): e52776.

Sun, L. K., et al. "Chimeric antibody with human constant regions and mouse variable regions directed against carcinoma-associated antigen 17-1A." Proceedings of the National Academy of Sciences 84.1 (1987): 214-218.

Tabb, D. L., et al. "DTASelect and Contrast: tools for assembling and comparing protein identifications from shotgun proteomics." Journal of proteome research 1.1 (2002): 21-26.

Tanji, K., et al. "p62/sequestosome 1 binds to TDP-43 in brains with frontotemporal lobar degeneration with TDP-43 inclusions." Journal of neuroscience research 90.10 (2012): 2034-2042.

Tatebe H, et al. Quantification of plasma phosphorylated tau to use as a biomarker for brain Alzheimer pathology: pilot case-control studies including patients with Alzheimer's disease and down syndrome. Mol Neurodegener. 2017;12 (1):63.

Toyama BH et al. (2013) Identification of long-lived proteins reveals exceptional stability of essential cellular structures. Cell. 154 (5): 971-82.

(56) References Cited

OTHER PUBLICATIONS

Vaccaro, A., et al. "Mutant TDP-43 and FUS cause age-dependent paralysis and neurodegeneration in C. elegans." PloS one 7.2 (2012): e31321.

Venkataraman, L., et al. "Isolation and characterization of antibody fragments selective for human FTD brain derived TDP-43 variants." BMC Neuroscience 21 (2020) 11 pages.

Ward, E. S., et al. "Binding activities of a repertoire of single immunoglobulin variable domains secreted from *Escherichia coli*." Nature 341.6242 (1989): 544-546.

Wood, C. R., et al. "The synthesis and in vivo assembly of functional antibodies in yeast." Nature 314.6010 (1985): 446-449.

Xia H et al. RNAi suppresses polyglutamine-induced neurodegeneration in a model of spinocerebellar ataxia. Nat Med. Aug. 2004;10(8):816-20.

Xia H et al. siRNA-mediated gene silencing in vitro and in vivo. Nat Biotechnol. Oct. 2002;20(10):1006-10.

Xia H et al. The HIV Tat protein transduction domain improves the biodistribution of beta-glucuronidase expressed from recombinant viral vectors. Nat Biotechnol. Jul. 2001;19(7):640-4.

Xu, T. et al. "ProLuCID: An improved SEQUEST-like algorithm with enhanced sensitivity and specificity." Journal of proteomics 129 (2015): 16-24.

Zhang H. et al. (2011). On Fitting Generalized Linear Mixed-effects Models for Binary Responses using Different Statistical Packages. Statistics in Medicine, 30, 2562-2572.

Zhang H. et al. (2011). On Modeling Longitudinal Binomial Responses—Implications from Two Dueling Paradigms. Journal of Applied Statistics, 38, 2373-2390.

Zhang H. et al. (2012). A new look at the difference between the GEE and the GLMM when modeling longitudinal count responses. Journal of Applied Statistics, 39:2067-2079.

Zhang H. et al. (2013). A Strategy to Model Nonmonotonic Dose-Response Curve and Estimate IC50. Plos One, 8: e69301.

Zhang H. et al. (2015). A non-parametric model to address overdispersed count response in a longitudinal data setting with missingness. Statistical Method in Medical Research, 26:1461-1475.

Zhang H., et al. (2004). Cpc1, a Chlamydomonas central pair protein with an adenylate kinase domain. Journal of Cell Science 117:4179-4188.

Zhang H., et al. (2007). Acute Inflammation Alters Bicarbonate Transport in Mouse Ileum. Journal of Physiology 581:1221-33.

Zhang X.H. et al. (2005). Identification of a novel protein for memory regulation in the hippocampus. Biochemistry and Biophysics Research Communication, 334, 418-424.

Zhang, Z., et al. "Treatment evaluation for a data-driven subgroup in adaptive enrichment designs of clinical trials." Statistics in Medicine 37.1 (2018): 1-11.

Zhu L., et al. (2013). Joint Analysis of Longitudinal Data and Recurrent Episodes Data with Application to Medical Cost Analysis. Biometrical Journal, 55, 5-16.

Zhu, J., et al. "Suppression of progranulin expression leads to formation of intranuclear TDP-43 inclusions in vitro: a cell model of frontotemporal lobar degeneration." Journal of Neuropathology & Experimental Neurology 78.12 (2019): 1124-1129.

Zhuo, X.-F., et al. "Solid-state NMR reveals the structural transformation of the TDP-43 amyloidogenic region upon fibrillation." Journal of the American Chemical Society 142.7 (2020): 3412-3421.

Zoller, M. J., et al. "[32] Oligonucleotide-directed mutagenesis of DNA fragments cloned into M13 vectors." Methods in enzymology. vol. 100. Academic Press, 1983. 468-500.

European Patent Office. Extended European Search Report for Application No. 22877638.1, dated Aug. 1, 2025 (9 pages).

Pozzi, S., et al. "Monoclonal full-length antibody against TAR DNA binding protein 43 reduces related proteinopathy in neurons." JCI insight 5.21 (2020): e140420 (19 pages).

PATHOLOGIC TDP-43 AS A BIOMARKER FOR THE DIAGNOSIS OF TDP-43 PROTEINOPATHY

CROSS-REFERENCE TO RELATED APPLICATIONS

This application claims priority to U.S. Provisional Patent Application No. 63/251,383, filed Oct. 1, 2021, and U.S. Provisional Patent Application No. 63/252,353 filed Oct. 5, 2021, which are incorporated herein by reference in their entireties.

REFERENCE TO SEQUENCE LISTING

This application was filed with a Sequence Listing XML in ST.26 XML format in accordance with 37 C.F.R. § 1.821. The Sequence Listing XML file submitted in the USPTO Patent Center, "026389-9326-US03_sequence_listing_xml_7 May 2025.xml," was created on May 7, 2025, contains 26 sequences, has a file size of 28.0 kilobytes (28,672 bytes), and is incorporated by reference in its entirety into the specification.

FIELD

This disclosure relates to antibodies or antigen-binding fragments thereof and compositions comprising the same. The disclosure further relates to methods of detecting TAR DNA-binding protein 43 (TDP-43) in a biological sample, diagnosing a neurodegenerative disease in a subject, and selecting whether to enroll a subject in a clinical trial for frontotemporal lobar degeneration with TDP-43 inclusions (FTLD-TDP) using the antibodies or antigen-binding fragments thereof described herein. In addition, the disclosure relates to immunoassay kits for selectively detecting TDP-43 in a biological sample.

BACKGROUND

Populations are aging and neurodegenerative disease is becoming a growing and intractable health challenge. While Alzheimer's disease (AD) is the most common cause of dementia, frontotemporal dementia (FTD) is the second most common in people under 65. FTD is a heterogeneous neurodegenerative disease characterized by progressive behavior and/or language impairments that include a range of clinical subtypes, e.g., behavioral variant FTD, progressive non-fluent aphasia, and semantic dementia. Pathologically, most patients have frontotemporal lobar degeneration (FTLD). About half of those patients show an accumulation of hyperphosphorylated tau proteins (in a subtype called FTLD-tau), while most others show an accumulation of the transactive DNA-binding protein TDP-43 (the subtype FTLD-TDP). However, these clinical conditions may also be caused by unusual presentations of AD. Because different underlying pathologies require specific therapeutic interventions, robust biomarkers are urgently needed to correctly select appropriate drugs for individual patients based on their specific underlying molecular pathology (i.e., FTLD-tau, FTLD-TDP, or AD). Though signature cerebrospinal fluid (CSF) markers exist for AD (low Aβ42 together with high T-tau and P-tau), currently there are no reliable structural/functional imaging methodologies nor CSF/serum liquid biomarker-based methodologies available for diagnosing FTLD-tau or FTLD-TDP.

Thus, there is a need for identification of a robust plasma biomarkers for diagnosing FTLD-TDP and highly sensitive and specific immunoassays for the detection and quantification of the biomarker.

SUMMARY

In an aspect, the disclosure relates to an antibody or antigen-binding fragment thereof comprising an immunoglobulin heavy chain (HC) variable domain sequence and an immunoglobulin light chain (LC) variable domain sequence, wherein: (a) the immunoglobulin HC variable domain sequence comprises (i) an HC CDR1 comprising the amino acid sequence of SEQ ID NO: 4, (ii) an HC CDR2 comprising the amino acid sequence of SEQ ID NO: 5, and (iii) an HC CDR3 comprising the amino acid sequence of SEQ ID NO: 6; and (b) the immunoglobulin LC variable domain sequence comprises (i) an LC CDR1 comprising the amino acid sequence of SEQ ID NO: 8, (ii) an LC CDR2 comprising the amino acid sequence of SEQ ID NO: 9, and (iii) an LC CDR3 comprising the amino acid sequence of SEQ ID NO: 10. In an embodiment, the immunoglobulin HC variable domain sequence comprises the amino acid sequence of SEQ ID NO: 3; and the immunoglobulin LC variable domain sequence comprises the amino acid sequence of SEQ ID NO: 7.

In a further aspect, the disclosure relates to an antibody or antigen-binding fragment thereof comprising an immunoglobulin heavy chain (HC) variable domain sequence and an immunoglobulin light chain (LC) variable domain sequence, wherein: (a) the immunoglobulin HC variable domain sequence comprises (i) an HC CDR1 comprising the amino acid sequence of SEQ ID NO: 12, (ii) an HC CDR2 comprising the amino acid sequence of SEQ ID NO: 13, and (iii) an HC CDR3 comprising the amino acid sequence of SEQ ID NO: 14; and (b) the immunoglobulin LC variable domain sequence comprises (i) an LC CDR1 comprising the amino acid sequence of SEQ ID NO: 16, (ii) an LC CDR2 comprising the amino acid sequence of SEQ ID NO: 17, and (iii) an LC CDR3 comprising the amino acid sequence of SEQ ID NO: 18. In an embodiment, the immunoglobulin HC variable domain sequence comprises the amino acid sequence of SEQ ID NO: 11; and the immunoglobulin LC variable domain sequence comprises the amino acid sequence of SEQ ID NO: 15.

Another aspect of the disclosure provides an antibody or antigen-binding fragment thereof comprising an immunoglobulin heavy chain (HC) variable domain sequence and an immunoglobulin light chain (LC) variable domain sequence, wherein: (a) the immunoglobulin HC variable domain sequence comprises (i) an HC CDR1 comprising the amino acid sequence of SEQ ID NO: 20, (ii) an HC CDR2 comprising the amino acid sequence of SEQ ID NO: 21, and (iii) an HC CDR3 comprising the amino acid sequence of SEQ ID NO: 22; and (b) the immunoglobulin LC variable domain sequence comprises (i) an LC CDR1 comprising the amino acid sequence of SEQ ID NO: 24, (ii) an LC CDR2 comprising the amino acid sequence of SEQ ID NO: 25, and (iii) an LC CDR3 comprising the amino acid sequence of SEQ ID NO: 26. In an embodiment, the immunoglobulin HC variable domain sequence comprises the amino acid sequence of SEQ ID NO: 19; and the immunoglobulin LC variable domain sequence comprises the amino acid sequence of SEQ ID NO: 23. In another embodiment, the immunoglobulin heavy chain variable region and the immunoglobulin light chain variable region together bind at least a portion of TAR DNA-binding protein 43 (TDP-43; SEQ ID NO: 1). In another embodiment, the immunoglobulin heavy chain variable region and the immunoglobulin light chain variable region together bind at least a portion of SEQ ID NO: 2.

Another aspect of the disclosure provides an isolated nucleic acid comprising a nucleotide sequence encoding the antibody or antigen-binding fragment thereof as described herein.

Another aspect of the disclosure provides a use of one or more of the antibodies or antigen-binding fragments thereof as described herein to prescreen a subject for a clinical trial.

Another aspect of the disclosure provides an immunoassay comprising one or more of the antibodies or antigen-binding fragments thereof as described herein.

Another aspect of the disclosure provides a method of detecting TAR DNA-binding protein 43 (TDP-43; SEQ ID NO: 1) in a biological sample, the method comprising: contacting the sample with an antibody or antigen-binding fragment thereof, wherein the antibody or antigen-binding fragment comprises an immunoglobulin heavy chain (HC) variable domain sequence and an immunoglobulin light chain (LC) variable domain sequence, wherein: (a) the immunoglobulin HC variable domain sequence comprises (i) an HC CDR1 comprising the amino acid sequence of SEQ ID NO: 4, (ii) an HC CDR2 comprising the amino acid sequence of SEQ ID NO: 5, and (iii) an HC CDR3 comprising the amino acid sequence of SEQ ID NO: 6; and (b) the immunoglobulin LC variable domain sequence comprises (i) an LC CDR1 comprising the amino acid sequence of SEQ ID NO: 8, (ii) an LC CDR2 comprising the amino acid sequence of SEQ ID NO: 9, and (iii) an LC CDR3 comprising the amino acid sequence of SEQ ID NO: 10. In an embodiment, the method further comprises contacting the sample with a second antibody or antigen-binding fragment thereof, wherein the second antibody or antigen-binding fragment comprises an immunoglobulin HC variable domain sequence and an immunoglobulin LC variable domain sequence, wherein: (a) the immunoglobulin HC variable domain sequence comprises (i) an HC CDR1 comprising the amino acid sequence of SEQ ID NO: 12, (ii) an HC CDR2 comprising the amino acid sequence of SEQ ID NO: 13, and (iii) an HC CDR3 comprising the amino acid sequence of SEQ ID NO: 14; and (b) the immunoglobulin LC variable domain sequence comprises (i) an LC CDR1 comprising the amino acid sequence of SEQ ID NO: 16, (ii) an LC CDR2 comprising the amino acid sequence of SEQ ID NO: 17, and (iii) an LC CDR3 comprising the amino acid sequence of SEQ ID NO: 18. In another embodiment, the method further comprises contacting the sample with a second antibody or antigen-binding fragment thereof, wherein the second antibody or antigen-binding fragment comprises an immunoglobulin HC variable domain sequence and an immunoglobulin LC variable domain sequence, wherein: (a) the immunoglobulin HC variable domain sequence comprises (i) an HC CDR1 comprising the amino acid sequence of SEQ ID NO: 20, (ii) an HC CDR2 comprising the amino acid sequence of SEQ ID NO: 21, and (iii) an HC CDR3 comprising the amino acid sequence of SEQ ID NO: 22; and (b) the immunoglobulin LC variable domain sequence comprises (i) an LC CDR1 comprising the amino acid sequence of SEQ ID NO: 24, (ii) an LC CDR2 comprising the amino acid sequence of SEQ ID NO: 25, and (iii) an LC CDR3 comprising the amino acid sequence of SEQ ID NO: 26. In another embodiment, the TDP-43 is misfolded. In another embodiment, the sample comprises a cell or a tissue sample. In another embodiment, the sample comprises plasma, serum, or cerebrospinal fluid (CSF). In another embodiment, the sample is obtained from a subject that is diagnosed as having, suspected as having, or at risk of having or developing a neurodegenerative disease. In another embodiment, the neurodegenerative disease is frontotemporal lobar degeneration (FTLD). In another embodiment, the detection comprises one or more of immunohistochemistry (IHC), Meso Scale Discovery (MSD) biomarker assay, Western blotting, flow cytometry, radioimmunoassay (RIA), counting immunoassay (CIA), enzyme immunoassays (EIA) or enzyme-linked immunosorbent assays (ELISA), fluoroimmunoassay (FIA), or chemiluminescence immunoassay (CLIA).

Another aspect of the disclosure provides a method of diagnosing a neurodegenerative disease in a subject, the method comprising detecting the presence of TAR DNA-binding protein 43 (TDP-43; SEQ ID NO: 1) in a biological sample from the subject, the method comprising: contacting the sample with an antibody or antigen-binding fragment thereof, wherein the antibody or antigen-binding fragment comprises an immunoglobulin heavy chain (HC) variable domain sequence and an immunoglobulin light chain (LC) variable domain sequence, wherein: (a) the immunoglobulin HC variable domain sequence comprises (i) an HC CDR1 comprising the amino acid sequence of SEQ ID NO: 4, (ii) an HC CDR2 comprising the amino acid sequence of SEQ ID NO: 5, and (iii) an HC CDR3 comprising the amino acid sequence of SEQ ID NO: 6; and (b) the immunoglobulin LC variable domain sequence comprises (i) an LC CDR1 comprising the amino acid sequence of SEQ ID NO: 8, (ii) an LC CDR2 comprising the amino acid sequence of SEQ ID NO: 9, and (iii) an LC CDR3 comprising the amino acid sequence of SEQ ID NO: 10; wherein the presence of TDP-43 is indicative of the subject having a neurodegenerative disease. In an embodiment, the method further comprises contacting the sample with a second antibody or antigen-binding fragment thereof, wherein the second antibody or antigen-binding fragment comprises an immunoglobulin HC variable domain sequence and an immunoglobulin LC variable domain sequence, wherein: (a) the immunoglobulin HC variable domain sequence comprises (i) an HC CDR1 comprising the amino acid sequence of SEQ ID NO: 12, (ii) an HC CDR2 comprising the amino acid sequence of SEQ ID NO: 13, and (iii) an HC CDR3 comprising the amino acid sequence of SEQ ID NO: 14; and (b) the immunoglobulin LC variable domain sequence comprises (i) an LC CDR1 comprising the amino acid sequence of SEQ ID NO: 16, (ii) an LC CDR2 comprising the amino acid sequence of SEQ ID NO: 17, and (iii) an LC CDR3 comprising the amino acid sequence of SEQ ID NO: 18. In another embodiment, the method further comprises contacting the sample with a second antibody or antigen-binding fragment thereof, wherein the second antibody or antigen-binding fragment comprises an immunoglobulin HC variable domain sequence and an immunoglobulin LC variable domain sequence, wherein: (a) the immunoglobulin HC variable domain sequence comprises (i) an HC CDR1 comprising the amino acid sequence of SEQ ID NO: 20, (ii) an HC CDR2 comprising the amino acid sequence of SEQ ID NO: 21, and (iii) an HC CDR3 comprising the amino acid sequence of SEQ ID NO: 22; and (b) the immunoglobulin LC variable domain sequence comprises (i) an LC CDR1 comprising the amino acid sequence of SEQ ID NO: 24, (ii) an LC CDR2 comprising the amino acid sequence of SEQ ID NO: 25, and (iii) an LC CDR3 comprising the amino acid sequence of SEQ ID NO: 26. In another embodiment, the neurodegenerative disease is frontotemporal lobar degeneration (FTLD).

Another aspect of the disclosure provides an immunoassay kit for selectively detecting TAR DNA-binding protein 43 (TDP-43; SEQ ID NO: 1) in a biological sample, the kit comprising: an antibody or antigen-binding fragment thereof, wherein the antibody or antigen-binding fragment comprises an immunoglobulin heavy chain (HC) variable domain sequence and an immunoglobulin light chain (LC) variable domain sequence, wherein: (a) the immunoglobulin HC variable domain sequence comprises (i) an HC CDR1 comprising the amino acid sequence of SEQ ID NO: 4, (ii) an HC CDR2 comprising the amino acid sequence of SEQ ID NO: 5, and (iii) an HC CDR3 comprising the amino acid sequence of SEQ ID NO: 6; and (b) the immunoglobulin LC variable domain sequence comprises (i) an LC CDR1 comprising the amino acid sequence of SEQ ID NO: 8, (ii) an LC CDR2 comprising the amino acid sequence of SEQ ID NO: 9, and (iii) an LC CDR3 comprising the amino acid sequence of SEQ ID NO: 10; and, a detection reagent. In an embodiment, the kit further comprises a solid support for the antibody or antigen-binding fragment thereof. In another embodiment, the kit further comprises a detection means. In another embodiment, the detection means is one or more of fluorescent, luminescent, radioactive, and colorimetric. In another embodiment, the detection reagent is one or more of colorimetric substrates, chemiluminescent substrates, and fluorescent substrates. In another embodiment, comprising a second antibody or antigen-binding fragment thereof, wherein the second antibody or antigen-binding fragment comprises an immunoglobulin HC variable domain sequence and an immunoglobulin LC variable domain sequence, wherein: (a) the immunoglobulin HC variable domain sequence comprises (i) an HC CDR1 comprising the amino acid sequence of SEQ ID NO: 12, (ii) an HC CDR2 comprising the amino acid sequence of SEQ ID NO: 13, and (iii) an HC CDR3 comprising the amino acid sequence of SEQ ID NO: 14; and (b) the immunoglobulin LC variable domain sequence comprises (i) an LC CDR1 comprising the amino acid sequence of SEQ ID NO: 16, (ii) an LC CDR2 comprising the amino acid sequence of SEQ ID NO: 17, and (iii) an LC CDR3 comprising the amino acid sequence of SEQ ID NO: 18. In another embodiment, the kit further comprises a second antibody or antigen-binding fragment thereof, wherein the second antibody or antigen-binding fragment comprises an immunoglobulin HC variable domain sequence and an immunoglobulin LC variable domain sequence, wherein: (a) the immunoglobulin HC variable domain sequence comprises (i) an HC CDR1 comprising the amino acid sequence of SEQ ID NO: 20, (ii) an HC CDR2 comprising the amino acid sequence of SEQ ID NO: 21, and (iii) an HC CDR3 comprising the amino acid sequence of SEQ ID NO: 22; and (b) the immunoglobulin LC variable domain sequence comprises (i) an LC CDR1 comprising the amino acid sequence of SEQ ID NO: 24, (ii) an LC CDR2 comprising the amino acid sequence of SEQ ID NO: 25, and (iii) an LC CDR3 comprising the amino acid sequence of SEQ ID NO: 26.

Another aspect of the disclosure provides a method for selecting whether to enroll a subject in a clinical trial for frontotemporal lobar degeneration with TAR DNA-binding protein 43 inclusions (FTLD-TDP), comprising: (a) measuring expression levels of TAR DNA-binding protein 43 (TDP-43; SEQ ID NO: 1) in a sample from the subject, wherein the measuring comprises contacting the sample with an antibody or antigen-binding fragment thereof, wherein the antibody or antigen-binding fragment comprises an immunoglobulin heavy chain (HC) variable domain sequence and an immunoglobulin light chain (LC) variable domain sequence, wherein: (a1) the immunoglobulin HC variable domain sequence comprises (a1a) an HC CDR1 comprising the amino acid sequence of SEQ ID NO: 4, (a1b) an HC CDR2 comprising the amino acid sequence of SEQ ID NO: 5, and (a1c) an HC CDR3 comprising the amino acid sequence of SEQ ID NO: 6; and (a2) the immunoglobulin LC variable domain sequence comprises (a2a) an LC CDR1 comprising the amino acid sequence of SEQ ID NO: 8, (a2b) an LC CDR2 comprising the amino acid sequence of SEQ ID NO: 9, and (a2c) an LC CDR3 comprising the amino acid sequence of SEQ ID NO: 10; (b) comparing the expression levels of the TDP-43 to a threshold expression level; and, wherein: (b1) if the expression levels of TDP-43 are above the threshold expression level, the subject is selected for the clinical trial; or, (b2) if the expression levels of TDP-43 are below the threshold expression level, the subject is not selected for the clinical trial. In an embodiment, the measuring further comprises contacting the sample with a second antibody or antigen-binding fragment thereof, wherein the second antibody or antigen-binding fragment comprises an immunoglobulin HC variable domain sequence and an immunoglobulin LC variable domain sequence, wherein: (a) the immunoglobulin HC variable domain sequence comprises (i) an HC CDR1 comprising the amino acid sequence of SEQ ID NO: 12, (ii) an HC CDR2 comprising the amino acid sequence of SEQ ID NO: 13, and (iii) an HC CDR3 comprising the amino acid sequence of SEQ ID NO: 14; and (b) the immunoglobulin LC variable domain sequence comprises (i) an LC CDR1 comprising the amino acid sequence of SEQ ID NO: 16, (ii) an LC CDR2 comprising the amino acid sequence of SEQ ID NO: 17, and (iii) an LC CDR3 comprising the amino acid sequence of SEQ ID NO: 18. In another embodiment, the measuring further comprises contacting the sample with a second antibody or antigen-binding fragment thereof, wherein the second antibody or antigen-binding fragment comprises an immunoglobulin HC variable domain sequence and an immunoglobulin LC variable domain sequence, wherein: (a) the immunoglobulin HC variable domain sequence comprises (i) an HC CDR1 comprising the amino acid sequence of SEQ ID NO: 20, (ii) an HC CDR2 comprising the amino acid sequence of SEQ ID NO: 21, and (iii) an HC CDR3 comprising the amino acid sequence of SEQ ID NO: 22; and (b) the immunoglobulin LC variable domain sequence comprises (i) an LC CDR1 comprising the amino acid sequence of SEQ ID NO: 24, (ii) an LC CDR2 comprising the amino acid sequence of SEQ ID NO: 25, and (iii) an LC CDR3 comprising the amino acid sequence of SEQ ID NO: 26.

The disclosure provides for other aspects and embodiments that will be apparent in light of the following detailed description and accompanying figures.

BRIEF DESCRIPTION OF THE DRAWINGS

FIG. 5A is images of immunofluorescent staining with MAb #9. The immunofluorescent staining images reveal immunopositivity in HEK293 cells transfected with a TDP-43-expressing plasmid (arrows). The p409/410 MAb was a positive control and the mouse IgG was a negative control. FIG. 5B shows images of MAb #9 immunostaining. Immunoreactivity of MAb #9 was ablated by competition with a peptide harboring the epitope recognized by MAb #9 in anterior horn motor neurons (arrows) of a subject who suffered from ALS. The scale bar is 50 μm.

FIG. 6A is a bar chart showing absorbance values from an ELISA using MAb #9 against plasma samples from subjects diagnosed with various pathologies. FIG. 6B is images of immunoblotting of the plasma samples with the p409/410 MAb and MAb #9. Type A1 is FTLD-TDP Type A sample 1; AD+TDP is AD with TDP-43 pathology; AD-TDP is AD without TDP-43 pathology; PSP is progressive supranuclear palsy; CBD is corticobasal degeneration.

FIG. 7A is images of immunostaining with MAb #9 and p409/410 MAb. MAb #9 detects similar pathologic TDP-43 inclusions as those seen with the p409/410 MAb (arrows), except for more fine neurites in the frontal cortex of a subject who suffered from FTLD-TDP Type A (arrowhead), novel fine neurites in the frontal cortex of Type B (arrowhead), and novel inclusions in the hippocampus of a subject who suffered from AD with TDP pathology (arrowhead). In Type A, the density of the MAb #9-positive inclusions is highest in layer 2 (inset of hematoxylin and eosin [H&E] image), which has the most severe neuronal loss of all layers. The scale bar is 50 μm. FIG. 7B is immunofluorescent images of MAb #9 immunostaining that reveals more TDP-43 pathology (arrowheads) in the anterior horn motor neurons of a subject who suffered from ALS with a C9 mutation. The arrow shows the only inclusion positive for both the p409/410 MAb and MAb #9. The scale bar is 50 μm. FIG. 7C is a bar chart showing semiquantification of TDP-43 pathology. **, p<0.01; n=5.

DETAILED DESCRIPTION

Figure 1:
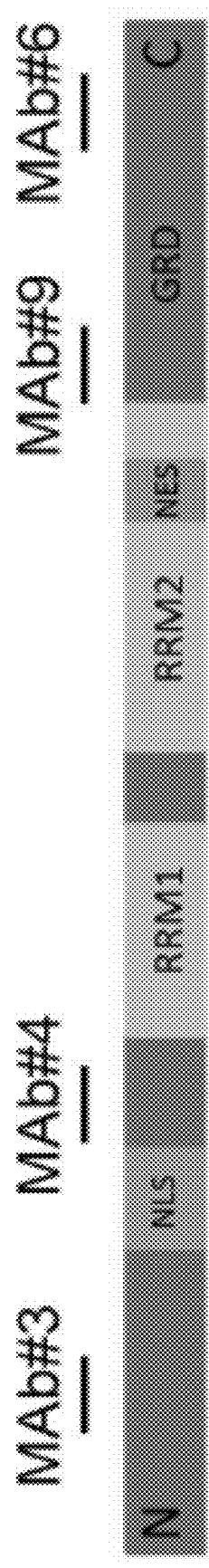
FIG. 1 is a schematic showing epitopes in TDP-43 recognized by monoclonal antibodies (MAbs) #3, #4, #9, and #6.

The presently disclosed subject matter is introduced with sufficient details to provide an understanding of one or more particular embodiments of broader inventive subject matters. The descriptions expound upon and exemplify features of those embodiments without limiting the inventive subject matters to the explicitly described embodiments and features. Considerations in view of these descriptions will likely give rise to additional and similar embodiments and features without departing from the scope of the presently disclosed subject matter.

Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and," and "the" include plural references unless the context clearly dictates otherwise. The present disclosure also contemplates other embodiments "comprising," "consisting of," and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

The term "about" or "approximately" as used herein as applied to one or more values of interest, refers to a value that is similar to a stated reference value, or within an acceptable error range for the particular value as determined by one of ordinary skill in the art, which will depend in part on how the value is measured or determined, including the limitations of the measurement system. In certain aspects, the term "about" refers to a range of values that fall within 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value). Alternatively, "about" can mean within 3 or more than 3 standard deviations, per the practice in the art. Alternatively, such as with respect to biological systems or processes, the term "about" can mean within an order of magnitude, preferably within 5-fold, and more preferably within 2-fold, of a value.

"Amino acid" as used herein refers to naturally occurring and non-natural synthetic amino acids, as well as amino acid analogs and amino acid mimetics that function in a manner similar to the naturally occurring amino acids. Naturally occurring amino acids are those encoded by the genetic code. Amino acids can be referred to herein by either their commonly known three-letter symbols or by the one-letter symbols recommended by the IUPAC-IUB Biochemical Nomenclature Commission. Amino acids include the side chain and polypeptide backbone portions.

As used herein, the term "antibody" collectively refers to immunoglobulins or immunoglobulin-like molecules including by way of example and without limitation, IgA, IgD, IgE, IgG and IgM, combinations thereof, and similar molecules produced during an immune response in any vertebrate, for example, in mammals such as humans, goats, rabbits and mice, as well as non-mammalian species, such as shark immunoglobulins. The term "antibody" includes intact immunoglobulins and "antibody fragments" or "antigen binding fragments" that specifically bind to a molecule of interest (or a group of highly similar molecules of interest) to the substantial exclusion of binding to other molecules (for example, antibodies and antibody fragments that have a binding constant for the molecule of interest that is at least 103 $M^{-1}$ greater, at least 104 $M^{-1}$ greater, or at least 105 $M^{-1}$ greater than a binding constant for other molecules in a biological sample). The term "antibody" also includes genetically engineered forms such as chimeric antibodies (for example, humanized murine antibodies), heteroconjugate antibodies (such as, bispecific antibodies). See also, Pierce Catalog and Handbook, 1994-1995 (Pierce Chemical Co., Rockford, Ill.); Kuby, J., Immunology, 3rd Ed., W. H. Freeman & Co., New York, 1997. More particularly, "antibody" refers to a polypeptide ligand comprising at least a light chain or heavy chain immunoglobulin variable region which specifically recognizes and binds an epitope of an antigen. Antibodies are composed of a heavy and a light chain, each of which has a variable region, termed the variable heavy (VH) region and the variable light (VL) region. Together, the VH region and the VL region are responsible for binding the antigen recognized by the antibody.

Typically, an immunoglobulin has heavy (H) chains and light (L) chains interconnected by disulfide bonds. There are two types of light chain, lambda (λ) and kappa (κ). There are five main heavy chain classes (or isotypes) which determine the functional activity of an antibody molecule: IgM, IgD, IgG, IgA and IgE. Each heavy and light chain contains a constant region and a variable region, (the regions are also known as "domains"). In combination, the heavy and the light chain variable regions specifically bind the antigen. Light and heavy chain variable regions contain a "framework" region interrupted by three hypervariable regions, also called "complementarity-determining regions" or "CDRs". The extent of the framework region and CDRs have been defined (see, Kabat et al., Sequences of Proteins of Immunological Interest, U.S. Department of Health and Human Services, 1991, which is hereby incorporated by reference). The Kabat database is now maintained online. The sequences of the framework regions of different light or heavy chains are relatively conserved within a species. The framework region of an antibody, that is the combined framework regions of the constituent light and heavy chains, largely adopt a B-sheet conformation and the CDRs form loops which connect, and in some cases form part of, the B-sheet structure. Thus, framework regions act to form a scaffold that provides for positioning the CDRs in correct orientation by inter-chain, non-covalent interactions. The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a VH CDR3 is located in the variable domain of the heavy chain of the antibody in which it is found, whereas a VL CDR1 is the CDR1 from the variable domain of the light chain of the antibody in which it is found. An antibody that binds pathologic TDP-43 will have a specific VH region and the VL region sequence, and thus specific CDR sequences. Antibodies with different specificities (i.e., different combining sites for different antigens) have different CDRs. Although it is the CDRs that vary from antibody to antibody, only a limited number of amino acid positions within the CDRs are directly involved in antigen binding. These positions within the CDRs are called specificity determining residues (SDRs).

The term "antibody" is further intended to encompass digestion fragments, specified portions, derivatives, and variants thereof, including antibody mimetics or comprising portions of antibodies that mimic the structure and/or function of an antibody or specified fragment or portion thereof, including single chain antibodies and fragments thereof. Examples of binding fragments encompassed within the term "antigen binding portion" of an antibody include a Fab fragment, a monovalent fragment consisting of the VL, VH, CL and CH, domains; a F(ab')2 fragment, a bivalent fragment comprising two Fab fragments linked by a disulfide bridge at the hinge region; a Fd fragment consisting of the VH and CH, domains; a Fv fragment consisting of the VL and VH domains of a single arm of an antibody, a dAb fragment (Ward et al. (1989) Nature 341:544-546), which consists of a VH domain; and an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv)). Bird et al. (1988) Science 242:423-426 and Huston et al. (1988) Proc. Natl. Acad Sci. USA 85:5879-5883. Single chain antibodies are also intended to be encompassed within the term "fragment of an antibody." Any of the above-noted antibody fragments are obtained using conventional techniques known to those of skill in the art, and the fragments are screened for binding specificity and neutralization activity in the same manner as are intact antibodies.

"Antibody fragments" or "antigen binding fragments" include proteolytic antibody fragments (such as $F(ab')_2$ fragments, Fab' fragments, Fab'-SH fragments and Fab fragments as are known in the art), recombinant antibody fragments (such as sFv fragments, $dsF_v$ fragments, bispecific sFv fragments, bispecific $dsF_v$ fragments, $F(ab)'_2$ fragments, single chain Fv proteins ("scFv"), disulfide stabilized Fv proteins ("$dsF_v$"), diabodies, and triabodies (as are known in the art), and camelid antibodies (see, for example, U.S. Pat. Nos. 6,015,695; 6,005,079; 5,874,541; 5,840,526; 5,800, 988; and 5,759,808). An scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains.

As used herein, the term "antibody derivative" is intended to encompass molecules that bind an epitope as defined herein and which are modifications or derivatives of an isolated pathologic TDP-43-binding antibody of this disclosure. Derivatives include, but are not limited to, for example, bispecific, heterospecific, trispecific, tetraspecific, multispecific antibodies, diabodies, chimeric, recombinant, and humanized. As used herein, the term "bispecific molecule" is intended to include any agent, e.g., a protein, peptide, or protein or peptide complex, which has two different binding specificities. As used herein, the term "multispecific molecule" or "heterospecific molecule" is intended to include any agent, e.g., a protein, peptide, or protein or peptide complex, which has more than two different binding specificities. As used herein, the term "heteroantibodies" refers to two or more antibodies, antibody binding fragments (e.g., Fab), derivatives thereof, or antigen binding regions linked together, at least two of which have different specificities.

The term "antibody variant" is intended to include antibodies produced in a species other than a rabbit. It also includes antibodies containing post-translational modifications to the linear polypeptide sequence of the antibody or fragment. It further encompasses fully human antibodies.

As used herein, the term "antigen" refers to a compound, composition, or substance that may be specifically bound by the products of specific humoral or cellular immunity, such as an antibody molecule or T-cell receptor. Antigens can be any type of molecule including, for example, haptens, simple intermediary metabolites, sugars (e.g., oligosaccharides), lipids, and hormones as well as macromolecules such as complex carbohydrates (e.g., polysaccharides), phospholipids, peptides, oligopeptides, polypeptides, and proteins. Common categories of antigens include, but are not limited to, viral antigens, bacterial antigens, fungal antigens, protozoa and other parasitic antigens, antigens involved in neurological disease, tumor antigens, antigens involved in autoimmune disease, allergy and graft rejection, toxins, and other miscellaneous antigens.

As used herein, an "assay" or "diagnostic assay" can be of any type of assay applied in the field of diagnostics. Such an assay may be based on the binding of an analyte to be detected to one or more capture probes with a certain affinity.

As used herein, "binding affinity" refers to the tendency of one molecule to bind (typically non-covalently) with another molecule, such as the tendency of a member of a specific binding pair for another member of a specific binding pair. A binding affinity can be measured as a binding constant, which binding affinity for a specific binding pair (such as an antibody/antigen pair) can be at least $1\times10^{-5}$ M, at least $1\times10^{-6}$ M, at least $1\times10^{-7}$ M, at least $1\times10^{-8}$ M, at least $1\times10^{-9}$ M, at least $1\times10^{-10}$ M, at least $1\times10^{-11}$ M, or at least $1\times10^{-12}$ M. Binding affinity may be calculated by a modification of the Scatchard method described by Frankel et al., Mol. Immunol., 16:101-106, 1979 or by an antigen/antibody dissociation rate. A high binding affinity may be measured by a competition radioimmunoassay. A high binding affinity for an antibody/antigen pair may be at least about $1\times10^{-8}$ M, at least about $1.5\times10^{-8}$ M, at least about $2.0\times10^{-8}$ M, at least about $2.5\times10^{-8}$ M, at least about $3.0\times10^{-8}$ M, at least about $3.5\times10^{-8}$ M, at least about $4.0\times10^{-8}$ M, at least about $4.5\times10^{-8}$ M, or at least about $5.0\times10^{-8}$ M.

"Binding region" as used herein refers to the region within a target region of an antigen, and particularly an antigenic protein (e.g., TDP-43), that is recognized and bound by an antibody described herein.

As used herein, the term "biological equivalent thereof" is intended to be synonymous with "equivalent thereof" when referring to a reference protein, antibody, polypeptide, polynucleotide, or nucleic acid, and intends those having minimal homology while still maintaining desired structure or functionality. Unless specifically recited herein, it is contemplated that any nucleic acid, polynucleotide, polypeptide, protein, or antibody mentioned herein also includes equivalents thereof. For example, an equivalent intends at least about 80% homology or identity and alternatively, at least about 85%, or alternatively at least about 90%, or alternatively at least about 95%, or alternatively 98% percent homology or identity and exhibits substantially equivalent biological activity to the reference protein, polypeptide, antibody, or nucleic acid. In one aspect, the term "equivalent" or "biological equivalent" of an antibody means the ability of the antibody to selectively bind its epitope protein or fragment thereof as measured by ELISA, IHC, or other suitable methods. Biologically equivalent antibodies include, but are not limited to, those antibodies, peptides, antibody fragments, antibody variant, antibody derivative, and antibody mimetics that bind to the same epitope as the reference antibody. One skilled in the art can prepare an antibody functionally equivalent to the antibodies of the present disclosure by introducing appropriate mutations into the antibody using site-directed mutagenesis (Hashimoto-Gotoh, T. et al., Gene 152, 271-275 (1995); Zoller & Smith, Methods Enzymol. 100, 468-500 (1983); Kramer, W. et al., Nucleic Acids Res. 12, 9441-9456 (1984); Kramer W. & Fritz H J., Methods. Enzymol. 154, 350-367 (1987); Kunkel, T A., Proc Natl Acad Sci USA. 82, 488-492 (1985); and Kunkel, Methods Enzymol. 85, 2763-2766 (1988)). Antibodies that are functionally equivalent to the antibodies of the present disclosure and comprise an amino acid sequence comprising mutation of one or more amino acids in the amino acid sequence of an antibody of the present disclosure are also included in the antibodies of the present disclosure. In such mutants, the number of amino acids that are mutated may be generally 50 amino acids or less, preferably 30 or less, and more preferably 10 or less (for example, 5 amino acids or less). An amino acid residue may be mutated into one that conserves the properties of the amino acid side chain. For example, based on their side chain properties, amino acids are classified into: hydrophobic amino acids (A, I, L, M, F, P, W, Y, and V); hydrophilic amino acids (R, D, N, C, E, Q, G, H, K, S, and T); amino acids having aliphatic side-chains (G, A, V, L, I, and P); amino acids having hydroxyl group-containing side-chains (S, T, and Y); amino acids having sulfur atom-containing side-chains (C and M); amino acids having carboxylic acid- and amide-containing side-chains (D, N, E, and Q); base-containing side-chains (R, K, and H); and amino acids having aromatic-containing side-chains (H, F, Y, and W).

As used herein, the term "chimeric antibody" means an antibody in which the Fc constant region of a monoclonal antibody from one species (e.g., a mouse Fc constant region) is replaced, using recombinant DNA techniques, with an Fc constant region from an antibody of another species (e.g., a human Fc constant region). See generally, Robinson et al., PCT/US86/02269; Akira et al., European Patent Application 184,187; Taniguchi, European Patent Application 171,496; Morrison et al., European Patent Application 173,494; Neuberger et al., WO 86/01533; Cabilly et al. U.S. Pat. No. 4,816,567; Cabilly et al., European Patent Application 125, 023; Better et al., Science 240:1041-1043, 1988; Liu et al., Proc. Natl. Acad. Sci. USA 84:3439-3443, 1987; Liu et al., J. Immunol. 139:3521-3526, 1987; Sun et al., Proc. Natl. Acad. Sci. USA 84:214-218, 1987; Nishimura et al., Cancer Res 47:999-1005, 1987; Wood et al., Nature 314:446-449, 1885; and Shaw et al., J. Natl. Cancer Inst. 80:1553-1559, 1988. For example, the target binding region or site may be from a non-human source (e.g. mouse or primate) and the constant region may be human.

The terms "control," "reference level," and "reference" are used herein interchangeably. The reference level may be a predetermined value or range, which is employed as a benchmark against which to assess the measured result. "Control group" as used herein refers to a group of control subjects or cells. A control may be a subject or cell without a synthetic peptide mimetic as detailed herein. A control may be a subject, or a sample therefrom, whose disease state is known. The subject, or sample therefrom, may be healthy, diseased, diseased prior to treatment, diseased during treatment, or diseased after treatment, or a combination thereof.

As used herein, the term "detectable label" refers to a molecule or material that can produce a detectable (such as visually, electronically, or otherwise) signal that indicates the presence and/or concentration of the label in a sample. When conjugated to a specific binding molecule, the detectable label can be used to locate and/or quantify the target to which the specific binding molecule is directed. Thereby, the presence and/or concentration of the target in a sample can be detected by detecting the signal produced by the detectable label. A detectable label can be detected directly or indirectly, and several different detectable labels conjugated to different specific-binding molecules can be used in combination to detect one or more targets. For example, a first detectable label conjugated to an antibody specific to a target can be detected indirectly through the use of a second detectable label that is conjugated to a molecule that specifically binds the first detectable label. Multiple detectable labels that can be separately detected can be conjugated to different specific binding molecules that specifically bind different targets to provide a multiplexed assay that can provide simultaneous detection of the multiple targets in a sample. A detectable signal can be generated by any mechanism including absorption, emission and/or scattering of a photon (including radio frequency, microwave frequency, infrared frequency, visible frequency, and ultra-violet frequency photons). Detectable labels include colored, fluorescent, phosphorescent, and luminescent molecules and materials, catalysts (such as enzymes) that convert one substance into another substance to provide a detectable difference (such as by converting a colorless substance into a colored substance or vice versa, or by producing a precipitate or increasing sample turbidity), haptens that can be detected through antibody-hapten binding interactions using additional detectably labeled antibody conjugates, and paramagnetic and magnetic molecules or materials. Particular examples of detectable labels include enzymes such as horseradish peroxidase, alkaline phosphatase, acid phosphatase, glucose oxidase, β-galactosidase, or β-glucuronidase; fluorophores such as fluoresceins, luminophores, coumarins, BODIPY dyes, resorufins, and rhodamines (many additional examples of fluorescent molecules can be found in The Handbook—A Guide to Fluorescent Probes and Labeling Technologies, Molecular Probes, Eugene, Oreg.); nanoparticles such as quantum dots (obtained, for example, from QuantumDot Corp, Invitrogen Nanocrystal Technologies, Hayward, Calif.; see also, U.S. Pat. Nos. 6,815,064, 6,682,596 and 6,649,138, each of which patents is incorporated by reference herein); metal chelates such as DOTA and DPTA chelates of radioactive or paramagnetic metal ions like Gd3+; and liposomes, for example, liposomes containing trapped fluorescent molecules. Where the detectable label includes an enzyme, a detectable substrate such as a chromogen, a fluorogenic compound, or a luminogenic compound can be used in combination with the enzyme to generate a detectable signal (a wide variety of such compounds are commercially available, for example, from Invitrogen Corporation, Eugene, Oreg.). Particular examples of chromogenic compounds include diaminobenzidine (DAB), 4-nitrophenylphospate (pNPP), fast red, bromochloroindolyl phosphate (BCIP), nitro blue tetrazolium (NBT), BCIP/ NBT, fast red, AP Orange, AP blue, tetramethylbenzidine (TMB), 2,2'-azino-di-[3-ethylbenzothiazoline sulphonate]

(ABTS), o-dianisidine, 4-chloronaphthol (4-CN), nitrophenyl-3-D-galactopyranoside (ONPG), 0-phenylenediamine (OPD), 5-bromo-4-chloro-3-indolyl-β-galactopyranoside (X-Gal), methylumbelliferyl-β-D-galactopyranoside (MU-Gal), p-nitrophenyl-α-D-galactopyranoside (PNP), 5-bromo-4-chloro-3-indolyl-β-D-glucuronide (X-Gluc), 3-amino-9-ethyl carbazol (AEC), fuchsin, iodonitrotetrazolium (INT), tetrazolium blue, and tetrazolium violet. Alternatively, an enzyme can be used in a metallographic detection scheme. Metallographic detection methods include using an enzyme such as alkaline phosphatase in combination with a water-soluble metal ion and a redox-inactive substrate of the enzyme. The substrate is converted to a redox-active agent by the enzyme, and the redox-active agent reduces the metal ion, causing it to form a detectable precipitate (see, for example, U.S. Pat. No. 7,642,064, PCT Publication No. 2005/003777, and U.S. Patent Application Publication No. 2004/0265922; each of which is incorporated by reference herein). Metallographic detection methods include using an oxido-reductase enzyme (such as horseradish peroxidase) along with a water-soluble metal ion, an oxidizing agent, and a reducing agent, again to form a detectable precipitate (see, for example, U.S. Pat. No. 6,670,113, which is incorporated by reference herein).

As used herein, an "epitope" or "antigenic determinant" refers to particular chemical groups or contiguous or non-contiguous peptide sequences on a molecule that an antibody binds to. An antibody may bind to a particular antigenic epitope. Epitopes usually consist of chemically active surface groupings of molecules such as amino acids or sugar side chains and usually have specific three-dimensional structural characteristics, as well as specific charge characteristics. Conformational and non-conformational epitopes are distinguished in that the binding to the former but not the latter is lost in the presence of denaturing solvents. An epitope may be unique to a misfolded protein. An epitope may be present in a misfolded protein and not in the native or normal conformation of the protein. In an embodiment, an antibody or fragment thereof as described herein may recognize an epitope in misfolded or pathologic TDP-43 and not in native or normal or non-pathologic TDP-43.

As used herein, "homology" or "identical", percent "identity" or "similarity", when used in the context of two or more nucleic acids or polypeptide sequences, refers to two or more sequences or subsequences that are the same or have a specified percentage of nucleotides or amino acid residues that are the same, e.g., at least 60%, 65%, 70%, 75%, 80%, 85%, 90%, 91%, 92%, 93%, 94%, 95%, 96%, 97%, 98%, 99%, or higher identity over a specified region (e.g., nucleotide sequence encoding an antibody described herein or amino acid sequence of an antibody described herein). Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. The alignment and the percent homology or sequence identity can be determined using software programs known in the art, for example those described in Current Protocols in Molecular Biology (Ausubel et al., eds. 1987) Supplement 30, section 7.7.18, Table 7.7.1. Default parameters may be used for alignment. For example, an alignment program is BLAST, using default parameters. In particular, preferred programs are BLASTN and BLASTP. The terms "homology," "identical," percent "identity," or "similarity" also refer to, or can be applied to, the complement of a test sequence. The terms also include sequences that have deletions and/or additions, as well as those that have substitutions. As described herein, the preferred algorithms can account for gaps and the like. Preferably, identity exists over a region that is at least about 25 amino acids or nucleotides in length, or over a region that is at least 50-100 amino acids or nucleotides in length. An "unrelated" or "non-homologous" sequence shares less than 40% identity, or alternatively less than 25% identity, with one of the sequences of the present disclosure.

As used herein, the term "monoclonal antibody" or "MAb" refers to an antibody produced by a single clone of B-lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells (i.e., "hybridomas"). Monoclonal antibodies include humanized monoclonal antibodies.

As used herein, "neurodegenerative disease" refers to a group of conditions that result from progressive damage to neurons and nervous system connections that are essential for mobility, coordination, strength, sensation, and cognition. In particular, the neurodegenerative disease may be frontotemporal lobar degeneration (FTLD). "FTLD" refers to a group of disorders based on their neuropathology that cause damage and dysfunction of the frontal and temporal lobes of the brain. Many possible symptoms can result from FTLD, including, but not limited to, unusual behaviors, emotional problems, trouble communicating, difficulty with work, difficulty with walking, or combinations thereof. Alzheimer's disease (AD) is another neurodegenerative disorder that is a progressive deteriorative condition of the brain that affects memory, thought, and language. The degenerative changes of Alzheimer's disease lead to patches or plaques in the brain and the entanglement of nerve fibers (neurofibrillary tangles). Memory loss and behavioral changes occur as a result of these changes in brain tissue. AD, in contrast to FTLD, is usually a slow progressive illness that occurs in midlife but becomes increasingly more common over the age of 65 years. Difficulty with short-term memory is usually the first symptom of AD and early behavioral changes may not be noticed. As the disease progresses, memory loss increases and there are changes in personality, mood, and behavior. Disturbances of judgment and concentration occur, along with confusion and restlessness. The type, severity, sequence, and progression of mental changes vary widely. Long periods with little change are common, although occasionally the disease can be rapidly progressive. Alzheimer's disease generally affects most of the brain, whereas FTLD primarily affects the frontal and temporal lobes of the brain.

As used herein, "pathological" or "pathologic" pertains to or arises from disease. Pathological protein such as pathologic TDP-43 can be phosphorylated, be sensitive to phosphatases, have a different conformation from normal or non-pathological or healthy proteins, be misfolded, accumulate and form intranuclear and cytoplasmic aggregates.

A "peptide" or "polypeptide" is a linked sequence of two or more amino acids linked by peptide bonds. The polypeptide can be natural, synthetic, or a modification or combination of natural and synthetic. Peptides and polypeptides include proteins such as binding proteins, receptors, and antibodies. The terms "polypeptide," "protein," and "peptide" are used interchangeably herein. "Primary structure" refers to the amino acid sequence of a particular peptide.

"Secondary structure" refers to locally ordered, three dimensional structures within a polypeptide. Certain structures within proteins are commonly referred to as domains, for example, enzymatic domains, extracellular domains, transmembrane domains, pore domains, and cytoplasmic tail domains. "Domains" are portions of a polypeptide that form a compact unit of the polypeptide and are typically 15 to 350 amino acids long. Exemplary domains include domains with enzymatic activity or ligand binding activity. Typical domains are made up of sections of lesser organization such as stretches of beta-sheet and alpha-helices. "Tertiary structure" refers to the complete three-dimensional structure of a polypeptide monomer. "Quaternary structure" refers to the three-dimensional structure formed by the noncovalent association of independent tertiary units. A "motif" is a portion of a polypeptide sequence and includes at least two amino acids. A motif may be 2 to 20, 2 to 15, or 2 to 10 amino acids in length. A motif may include 3, 4, 5, 6, or 7 sequential amino acids. A domain may be comprised of a series of the same type of motif.

"Proteinopathy," e.g., any disease or condition that results from the abnormal synthesis, folding, post-translational modification, or deposition of protein in cells or tissues. Proteinopathy as used herein includes pathological proteins, such as pathological TDP-43 that can present epitopes not found in the TDP-43 protein in its native conformation.

"Sample" or "test sample" as used herein can mean any sample in which the presence and/or level of a target is to be detected or determined or any sample comprising an antibody or component thereof as detailed herein. Samples may include liquids, solutions, emulsions, or suspensions. Samples may include a medical sample. Samples may include any biological fluid or tissue, such as blood, whole blood, fractions of blood such as plasma and serum, muscle, interstitial fluid, sweat, saliva, urine, tears, synovial fluid, bone marrow, cerebrospinal fluid, nasal secretions, sputum, amniotic fluid, bronchoalveolar lavage fluid, gastric lavage, emesis, fecal matter, lung tissue, peripheral blood mononuclear cells, total white blood cells, lymph node cells, spleen cells, tonsil cells, cancer cells, tumor cells, bile, digestive fluid, skin, or combinations thereof. In some embodiments, the sample comprises an aliquot of a larger sample. In other embodiments, the sample comprises a biological fluid. Samples can be obtained by any means known in the art. The sample can be used directly as obtained from a patient or can be pre-treated, such as by filtration, distillation, extraction, concentration, centrifugation, inactivation of interfering components, addition of reagents, and the like, to modify the character of the sample in some manner as discussed herein or otherwise as is known in the art.

"Sensitivity" and "specificity" as used herein with regard to a diagnostic and/or prognostic test depends on more than just the analytical "quality" of the test, they also depend on the definition of what constitutes an abnormal result. In practice, Receiver Operating Characteristic curves (ROC curves), are typically calculated by plotting the value of a variable versus its relative frequency in "normal" (i.e., apparently healthy individuals not having a particular disorder or condition) and "disease" populations. For any particular marker, a distribution of marker levels for subjects with and without a disease will likely overlap. Under such conditions, a test does not absolutely distinguish a normal condition from a disease condition with 100% accuracy, and the area of overlap indicates where the test cannot distinguish normal from disease. A threshold is selected, below which the test is considered to be abnormal and above which the test is considered to be normal, or vice versa. The area under the ROC curve is a measure of the probability that the perceived measurement will allow correct identification of a condition. ROC curves can be used even when test results do not necessarily give an accurate number. As long as one can rank results, one can create a ROC curve. For example, results of a test on "disease" samples might be ranked according to degree (e.g., 1=low, 2=normal, and 3=high). This ranking can be correlated to results in the "normal" population, and a ROC curve created. These methods are well known in the art. See, e.g., Hanley et al. 1982. Radiology 143:29-36. For example, a threshold may be selected to provide a ROC curve area of greater than about 0.5, about 0.7, about 0.8, about 0.85, or about 0.9.

"Subject" and "patient" as used herein interchangeably refers to any vertebrate, including, but not limited to, a mammal that wants or is in need of the herein described compositions or methods. The subject may be a human or a non-human. The subject may be a vertebrate. The subject may be a mammal. The mammal may be a primate or a non-primate. The mammal can be a non-primate such as, for example, cow, pig, camel, llama, hedgehog, anteater, platypus, elephant, alpaca, horse, goat, rabbit, sheep, hamster, guinea pig, cat, dog, rat, and mouse. The mammal can be a primate such as a human. The mammal can be a non-human primate such as, for example, monkey, cynomolgus monkey, rhesus monkey, chimpanzee, gorilla, orangutan, and gibbon. The subject may be of any age or stage of development, such as, for example, an adult, an adolescent, or an infant. The subject may be male or female. In some embodiments, the subject has a specific genetic marker. The subject may be undergoing treatment either for the disease or condition being diagnosed or for another disease or condition, or other forms of treatment.

"Treatment" or "treating" or "treatment" when referring to protection of a subject from a disease, means suppressing, repressing, reversing, alleviating, ameliorating, or inhibiting the progress of disease, or completely eliminating a disease. A treatment may be either performed in an acute or chronic way. The term also refers to reducing the severity of a disease or symptoms associated with such disease prior to affliction with the disease. Preventing the disease can involve diagnosing a disease and administering a therapeutic composition to a subject prior to onset of the disease. Suppressing the disease involves administering a therapeutic composition to a subject after induction of the disease but before its clinical appearance. Repressing or ameliorating the disease involves administering a therapeutic composition to a subject after clinical appearance of the disease.

"Variant" with respect to a peptide or polypeptide that differs in amino acid sequence by the insertion, deletion, or conservative substitution of amino acids, but retain at least one biological activity. Variant may also mean a protein with an amino acid sequence that is substantially identical to a referenced protein with an amino acid sequence that retains at least one biological activity. Representative examples of "biological activity" include the ability to be bound by a specific antibody or polypeptide or to promote a particular response. Variant can mean a functional fragment thereof. Variant can also mean multiple copies of a polypeptide. The multiple copies can be in tandem or separated by a linker. A conservative substitution of an amino acid, for example, replacing an amino acid with a different amino acid of similar properties (for example, hydrophilicity, degree and distribution of charged regions) is recognized in the art as typically involving a minor change. These minor changes may be identified, in part, by considering the hydropathic index of amino acids, as understood in the art (Kyte et al., J. Mol. Biol. 1982, 157, 105-132). The hydropathic index of an amino acid is based on a consideration of its hydrophobicity and charge. It is known in the art that amino acids of similar hydropathic indexes may be substituted and still retain protein function. In one aspect, amino acids having hydropathic indexes of ±2 are substituted. The hydrophilicity of amino acids may also be used to reveal substitutions that would result in proteins retaining biological function. A consideration of the hydrophilicity of amino acids in the context of a peptide permits calculation of the greatest local average hydrophilicity of that peptide. Substitutions may be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

Unless otherwise defined herein, scientific and technical terms used in connection with the present disclosure shall have the meanings that are commonly understood by those of ordinary skill in the art. For example, any nomenclatures used in connection with, and techniques of, diagnostics, including medical or clinical diagnostics, cell and tissue culture, molecular biology, immunology, microbiology, genetics, and protein and nucleic acid chemistry and hybridization described herein are those that are well known and commonly used in the art. The meaning and scope of the terms should be clear; in the event however of any latent ambiguity, definitions provided herein take precedent over any dictionary or extrinsic definition. Further, unless otherwise required by context, singular terms shall include pluralities and plural terms shall include the singular.

Antibodies and Antigen-Binding Fragments Thereof

Provided herein are antibody or antigen-binding fragments thereof comprising an immunoglobulin heavy chain (HC) variable domain sequence and an immunoglobulin light chain (LC) variable domain sequence, wherein the heavy chain and light chain immunoglobulin variable domain sequences form an antigen binding site that binds to at least a portion of TAR DNA-binding protein 43 (TDP-43; SEQ ID NO: 1).

Also provided herein are antibody or antigen-binding fragments thereof comprising an immunoglobulin HC variable domain sequence and an immunoglobulin LC variable domain sequence, wherein the heavy chain and light chain immunoglobulin variable domain sequences form an antigen binding site that binds to at least a portion of the amino acid sequence of SEQ ID NO: 2.

Further provided herein are antibody or antigen-binding fragments thereof comprising an immunoglobulin heavy chain (HC) variable domain sequence and an immunoglobulin light chain (LC) variable domain sequence. The immunoglobulin HC variable domain sequence may comprise an HC CDR1 comprising the amino acid sequence of SEQ ID NO: 4, SEQ ID NO: 12, or SEQ ID NO: 20; an HC CDR2 comprising the amino acid sequence of SEQ ID NO: 5, SEQ ID NO: 13, or SEQ ID NO: 21; and an HC CDR3 comprising the amino acid sequence of SEQ ID NO: 6, SEQ ID NO: 14, or SEQ ID NO: 22. The immunoglobulin LC variable domain sequence may comprise an LC CDR1 comprising the amino acid sequence of SEQ ID NO: 8, SEQ ID NO: 16, or SEQ ID NO: 24; an LC CDR2 comprising the amino acid sequence of SEQ ID NO: 9, SEQ ID NO: 17, or SEQ ID NO: 25; and an LC CDR3 comprising the amino acid sequence of SEQ ID NO: 10, SEQ ID NO: 18, or SEQ ID NO: 26. The immunoglobulin HC variable domain sequence may comprise the amino acid sequence of SEQ ID NO: 3, SEQ ID NO: 11, or SEQ ID NO: 19. The immunoglobulin LC variable domain sequence may comprise the amino acid sequence of SEQ ID NO: 7, SEQ ID NO: 15, or SEQ ID NO: 23.

The antibodies as described herein may be a full-length antibody. The antibodies as described herein may be a monoclonal antibody. The antibodies described herein may comprise an Fc domain. The antibodies described herein may be a rabbit antibody, a human antibody, or a humanized antibody, or is non-immunogenic in a human. The antibodies as described herein may be a Fab, F(ab)'$_2$, Fab', scF$_v$, or F$_v$. One or more amino acid residues in a CDR of the antibodies or fragments thereof described herein may be substituted with another amino acid. The substitution may be conservative in the sense of being a substitution within the same family of amino acids.

Immunoassays

Further provided herein are immunoassays comprising one or more of the above-described antibodies or antigen-binding fragments thereof. In some embodiments, the immunoassay may comprise one or more of the antibodies or antigen-binding fragments thereof as described herein. The immunoassay may be a sandwich immunoassay wherein two antibodies or antigen-binding fragments thereof as described herein are comprised by the immunoassay where one antibody or antigen-binding fragment thereof is a capture antibody, and a second antibody or antigen-binding fragment thereof is a detection antibody to form an immune complex. An immunoassay as described herein may be a radioimmunoassay (RIA), enzyme immunoassay (EIA), Enzyme-linked immunoassays (ELISA), immunohistochemistry (IHC), Meso Scale Discovery (MSD) biomarker assay (MesoScale, Inc., Rockville, Maryland), Western blotting, flow cytometry, counting immunoassay (CIA), fluoroimmnoassay (FIA), chemiluminescence immunoassay (CLIA), Luminex-based bead arrays (Luminex, Corp., Austin, TX), protein microarray assays, or rapid test formats such as immunochromatographic strip tests.

The immunoassays can be homogenous or heterogeneous assays, competitive and non-competitive assays. In a particular, the immunoassay may be in the form of a sandwich assay, which is a non-competitive immunoassay, wherein the molecule to be detected and/or quantified is bound to a first antibody and to a second antibody. The first antibody may be bound to a solid phase, e.g., a bead, a surface of a well or other container, a chip or a strip, and the second antibody is an antibody which is labeled, e.g., with a dye, with a radioisotope, or a reactive or catalytically active moiety or vice versa. The amount of labeled antibody bound to the analyte is then measured by an appropriate method. The general composition and procedures involved with "sandwich assays" are well-established and known to the skilled person (The Immunoassay Handbook, Ed. David Wild, Elsevier LTD, Oxford; 3rd ed. (May 2005), ISBN-13:978-0080445267; Hultschig C et al., Curr Opin Chem Biol. 2006 February; 10 (1): 4-10. PMID: 16376134, incorporated herein by reference).

For example, the immunoassay may comprise two antibodies as described herein which are both present as dispersions in a liquid reaction mixture or one of the antibodies (e.g., the first antibody) may be labeled and the other antibody (e.g., the second antibody) may be bound to a solid phase or can be bound selectively to a solid phase wherein a first labelling component is attached to the first antibody, wherein said first labelling component is part of a labelling system based on fluorescence- or chemiluminescence-quenching or amplification, and a second labelling component of said marking system is attached to the second antibody, so that upon binding of both capture molecules to the analyte a measurable signal is generated that allows for the detection of the formed sandwich complexes in the solution comprising the sample.

Fluorescence based assays may comprise the use of dyes, which may be selected from the group comprising FAM (5- or 6-carboxyfluorescein), VIC, NED, Fluorescein, Fluoresceinisothiocyanate (FITC), IRD-700/800, Cyanine dyes, such as CY3, CYS, CY3.5, CY5.5, Cy7, Xanthen, 6-Carboxy-2',4',7',4,7-hexachlorofluorescein (HEX), TET, 6-Carboxy-4',5'-dichloro-2',7'-dimethodyfluorescein (JOE), N,N,N',N'-Tetramethyl-6-carboxyrhodamine (TAMRA), 6-Carboxy-X-rhodamine (ROX), 5-Carboxyrhodamine-6G (R6G5), 6-carboxyrhodamine-6G (RG6), Rhodamine, Rhodamine Green, Rhodamine Red, Rhodamine 110, BODIPY dyes, such as BODIPY TMR, Oregon Green, Coumarins such as Umbelliferone, Benzimides, such as Hoechst 33258; Phenanthridines, such as Texas Red, Yakima Yellow, Alexa Fluor, PET, Ethidiumbromide, Acridinium dyes, Carbazol dyes, Phenoxazine dyes, Porphyrine dyes, Polymethin dyes, and the like.

Chemiluminescence based assays may comprise the use of dyes, based on the physical principles described for chemiluminescent materials in Kirk-Othmer, Encyclopedia of chemical technology, 4th ed., executive editor, J. I. Kroschwitz; editor, M Howe-Grant, John Wiley & Sons, 1993, vol. 15, p. 518-562, incorporated herein by reference, including citations on pages 551-562. Chemiluminescent dyes may include acridinium esters, dioxetanes, or luminol.

Methods

Methods of Detecting TDP-43 in a Biological Sample

TDP-43 is composed of 414 amino acids, and functions as a heterogeneous nuclear ribonucleoprotein. The recognized domains of TDP-43 include two highly conserved RNA-recognition motifs and a glycine-rich C-terminal domain. Under normal conditions, TDP-43 mainly localizes to the nucleus, and functions to regulate gene transcription and mRNA splicing. In FTLD-TDP cases, TDP-43 changes conformation, misfolds, and accumulates in intranuclear and cytoplasmic aggregates. These aggregates result in the loss of nuclear TDP-43 function and are themselves toxic. Depending on the distribution and relative abundance of these TDP-43 aggregates, FTLD-TDP can be further classified into four distinct histopathologic types, A-D. TDP-43 aggregates are predominantly composed of pathologic TDP-43 proteins: mainly 45 kDa phosphorylated full-length TDP-43 and 25 kDa C-terminal fragments. Notably, both the full-length and C-terminal fragments of TDP-43 are phosphatase-sensitive, indicating disease-associated hyperphosphorylation. TDP-43's phosphorylation sites are mostly located in the glycine-rich C-terminal domain of the protein.

Pathologic TDP-43 in plasma may be used as a biomarker for FTLD. A promising approach for developing a biomarker for FTLD is the quantification of disease-specific biochemical markers present in patients' biofluids, such as CSF and plasma. Brain-derived pathologic TDP-43 is a top candidate as a biomarker for FTLD. However, there are several hurdles that will have to be overcome to make pathologic TDP-43 a robust biomarker, including: it is challenging to measure pathologic TDP-43 in cerebrospinal fluid (CSF) and plasma samples since they also contain normal TDP-43; the level of brain-derived, pathologic TDP-43 is low in plasma because protein exchange between the brain and blood is highly regulated through the blood-brain barrier; the pathologic TDP-43 level may be slightly higher in CSF due to the direct contact of the CSF compartment with the brain; currently there are no antibodies specific for the pathologic form of TDP-43; to measure pathologic TDP-43 in patients' biofluids, nearly all reported studies have used antibodies that bind to phosphorylated epitopes at the C-terminus of TDP-43 and such antibodies likely detect both forms of pathologic TDP-43 (i.e., full-length and C-terminal fragments) as well as non-pathologic nuclear TDP-43 through the non-specific binding of phosphorylated epitopes. To address these hurdles, the antibodies described herein are highly sensitive and specific for the pathologic form of TDP-43 and the immunoassays described herein are highly sensitive and quantitative for detecting brain-derived pathologic TDP-43, while limiting the contribution of normal TDP-43 signals in biofluids obtained from subjects.

Provided herein are methods of detecting TDP-43 in a biological sample. The methods may comprise contacting a sample with an antibody or antigen-binding fragment thereof as described herein. The methods may further comprise contacting the biological sample with a second antibody or antigen-binding fragment thereof as described herein. The TDP-43 may be pathologic TDP-43, misfolded TDP-43, or a combination thereof. The sample may comprise a cell, tissue sample, or a biological fluid. The sample may be a plasma, serum, or CSF sample. The sample may be obtained from a subject that is diagnosed as having, suspected as having, or at risk of having or developing a neurodegenerative disease. The neurodegenerative disease may be frontotemporal lobar degeneration (FTLD) or frontotemporal dementia (FTD). Detecting TDP-43 may comprise an immunoassay as described herein.

Methods of Diagnosing a Neurodegenerative Disease

Provided herein are methods of diagnosing a neurodegenerative disease in a subject. The method may comprise detecting the presence of TDP-43 in a biological sample from the subject as described herein. The neurodegenerative disease may be frontotemporal lobar degeneration (FTLD) or frontotemporal dementia (FTD).

Methods for Selecting Whether to Enroll a Subject in a Clinical Trial for Frontotemporal Lobar Degeneration with TAR DNA-Binding Protein 43 Inclusions (FTLD-TDP)

Provided herein are methods for selecting whether to enroll a subject in a clinical trial for FTLD-TDP. The method may include measuring expression levels of TDP-43 in a sample from the subject, wherein the measuring may comprise contacting the sample with one or more antibodies or antigen-binding fragments thereof as described herein. The method may further include comparing the expression levels of the TDP-43 to a threshold expression level. If the expression levels of TDP-43 are above the threshold expression level, the subject may be selected for the clinical trial. If the expression levels of TDP-43 are below the threshold expression level, the subject is not selected for the clinical trial.

Kits

Provided herein is an immunoassay kit, which may be used to selectively detect TDP-43 in a biological sample. The kit may comprise one or more antibodies or fragments thereof as described herein or an immunoassay comprising the same as described herein, for any of the methods as described herein, a detection reagent, and instructions for using said kit. The kit may further comprise a solid support for the antibody or antigen-binding fragment thereof. The kit may also comprise a detection means.

Instructions included in kits may be affixed to packaging material or may be included as a package insert. While the instructions are typically written on printed materials they are not limited to such. Any medium capable of storing such instructions and communicating them to an end user is contemplated by this disclosure. Such media include, but are not limited to, electronic storage media (e.g., magnetic discs, tapes, cartridges, chips), optical media (e.g., CD ROM), and the like. As used herein, the term "instructions" may also include the address of an internet site that provides the instructions.

EXAMPLES

The foregoing may be better understood by reference to the following examples, which are presented for purposes of illustration and are not intended to limit the scope of the invention. The present disclosure has multiple aspects and embodiments, as illustrated by the non-limiting examples below.

Example 1

Materials and Methods

Subjects. This study will include plasma (n=50 per group) and CSF (n=30 per group) samples from neuropathologically confirmed FTLD-TDP, FTLD-tau, and AD patients, and from normal aging individuals. The plasma and CSF samples have been obtained from the brain banks of the Alzheimer's Disease Centers (ADCs) of Northwestern University, the University of Pittsburgh, and the University of Pennsylvania. The inclusion and exclusion criteria are listed in Table 1.

TABLE 1

Inclusion and exclusion criteria.

| Group | Inclusion Criteria | Exclusion Criteria |
|---|---|---|
| FTLD-TDP | Subjects meet the pathology diagnostic guideline for FTLD-TDP (Mackenzie et al., *Acta Neuropathol.* 2009;117(1):15-8; Cairns et al., *Acta Neuropathol.* 2007;114(1):5-22; Mackenzie et al., *Acta Neuropathol.* 2010;119(1):1-4; McKhann et al., *Arch Neurol.* 2001;58(11):1803-9). | Any of the following: 1. Subjects meet the 2012 National Institute on Aging and Alzheimer's Association (NIA-AA) diagnostic guideline for moderate or high AD neuropathologic change (Hyman et al., *Alzheimers Dement.* 2012;8(1):1-13; Montine et al., *Acta Neuropathol.* 2012;123(1):1-11). 2. Subjects meet the pathology diagnostic guideline for FTLD-tau (Mackenzie et al., *Acta Neuropathol.* 2009;117(1):15-8; Cairns et al., *Acta* |

TABLE 1-continued

Inclusion and exclusion criteria.

| Group | Inclusion Criteria | Exclusion Criteria |
|---|---|---|
| | | *Neuropathol.* 2007;114(1):5-22; Mackenzie et al., *Acta Neuropathol.* 2010;119(1):1-4; McKhann et al., *Arch Neurol.* 2001;58(11):1803-9). 3. Subjects have stroke history with pathology confirmation. |
| FTLD-tau | Subjects meet the pathology diagnostic guideline for FTLD-tau (Mackenzie et al., *Acta Neuropathol.* 2009;117(1):15-8; Cairns et al., *Acta Neuropathol.* 2007;114(1):5-22; Mackenzie et al., *Acta Neuropathol.* 2010;119(1):1-4; McKhann et al., *Arch Neurol.* 2001;58(11):1803-9). | Any of the following: 1. Subjects meet the 2012 NIA-AA diagnostic guideline for moderate or high AD neuropathologic change. 2. Subjects meet the pathology diagnostic guideline for FTLD-TDP (Mackenzie et al., *Acta Neuropathol.* 2009;117(1):15-8; Cairns et al., *Acta Neuropathol.* 2007;114(1):5-22; Mackenzie et al., *Acta Neuropathol.* 2010;119(1):1-4; McKhann et al., *Arch Neurol.* 2001;58(11):1803-9). 3. Subjects have stroke history with pathology confirmation. |
| AD | Subjects meet the 2012 NIA-AA diagnostic guideline for moderate or high AD neuropathologic change (Hyman et al., *Alzheimers Dement.* 2012;8(1):1-13; Montine et al., *Acta Neuropathol.* 2012;123(1):1-11). | Any of the following: 1. Subjects meet the pathology diagnostic guideline for FTLD-TDP and FTLD-tau (Mackenzie et al., *Acta Neuropathol.* 2009;117(1):15-8; Cairns et al., *Acta Neuropathol.* 2007;114(1):5-22; Mackenzie et al., *Acta Neuropathol.* 2010;119(1):1-4; McKhann et al., *Arch Neurol.* 2001;58(11):1803-9). 2. Subjects have stroke history with pathology confirmation. |
| Control | Age > 40 years. Subjects who received lumbar puncture for exclusion diagnostics, where a negative finding was obtained. | 1. Any subjects with infarct, hemorrhage, epilepsy, tumor, traumatic brain injury, or other neurodegenerative disease. |

ELISA for Pathologic TDP-43 levels, and statistical analysis plan and sample size consideration. Plasma/CSF pathologic TDP-43 levels will be measured by an ELISA system described herein, with strict performance acceptance criteria and quality control samples on each plate. With each assay, the clinical samples will be processed together with a blank solution (sample diluent) and the (prepared) calibrator solutions. Low, medium, and high TDP-43 concentration quality control samples will be run on each assay plate, with an acceptance coefficient of variance (CV) cutoff of ≤20%. All samples will be run in triplicate. TDP-43 replicates with a CV>20% will be excluded from the analyses. All reported concentrations should fall within the qualified range of the assays. TDP-43 concentrations will be determined on a standard curve by plotting optical density versus concentration, using four-parameter logistic curve-fitting. Plasma/CSF data will be presented using box-plots, and potential outliers will be carefully examined and removed if necessary. Differences between plasma/CSF TDP-43 levels of FTLD-TDP patients with those of each of the other groups, i.e., FTLD-tau patients, AD patients, and control individuals, will be evaluated by two-sample t-test. Although the outcome might not follow normal distribution, a t-test is still expected to be appropriate based on Central Limit Theorem and the proposed sample size (n=50 for plasma and n=30 for CSF). To address the multiple testing issue, Bonferroni's adjustment will be applied. A receiver operating characteristic (ROC) curve will be plotted using plasma/CSF TDP-43 levels to diagnose of FTLD-TDP, but with different threshold criteria. The areas under the curve (AUC) for plasma and CSF TDP-43 levels will be compared. Fifty subjects would result in 80% statistical power to detect an AUC of 0.68 at a one-sided p<0.05 while assuming the actual AUC is 0.86. Similar ROC analyses will also be performed between FTLD-TDP, FTLD-tau, AD, and the aging control group to show the differences in TDP-43 levels between patients and controls. Statistical analyses will be performed using SAS 9.4. The Pearson's Correlation between CSF and plasma TDP-43 levels will be directly estimated with its 95% confidence interval.

Example 2

Production of Novel MAbs Against TDP-43

New TDP-43 MAbs were generated for the development of a disease-specific biomarker of FTLD-TDP. More than 3,000 Mab clones were screened by indirect ELISA and 13 promising MAbs were identified, which were then subjected to further epitope mapping by Western blotting. The epitope regions of four of those antibodies, illustrated in FIG. 1, are the N-terminus for MAbs #3 (AA 25-50) and #4 (AA 98-120) and the glycine-rich C-terminal domain for MAb #6 (AA 390-410) and #9 (AA 280-300).

Example 3

MAb Immunoreactivity in Human Tissues

Figure 2:
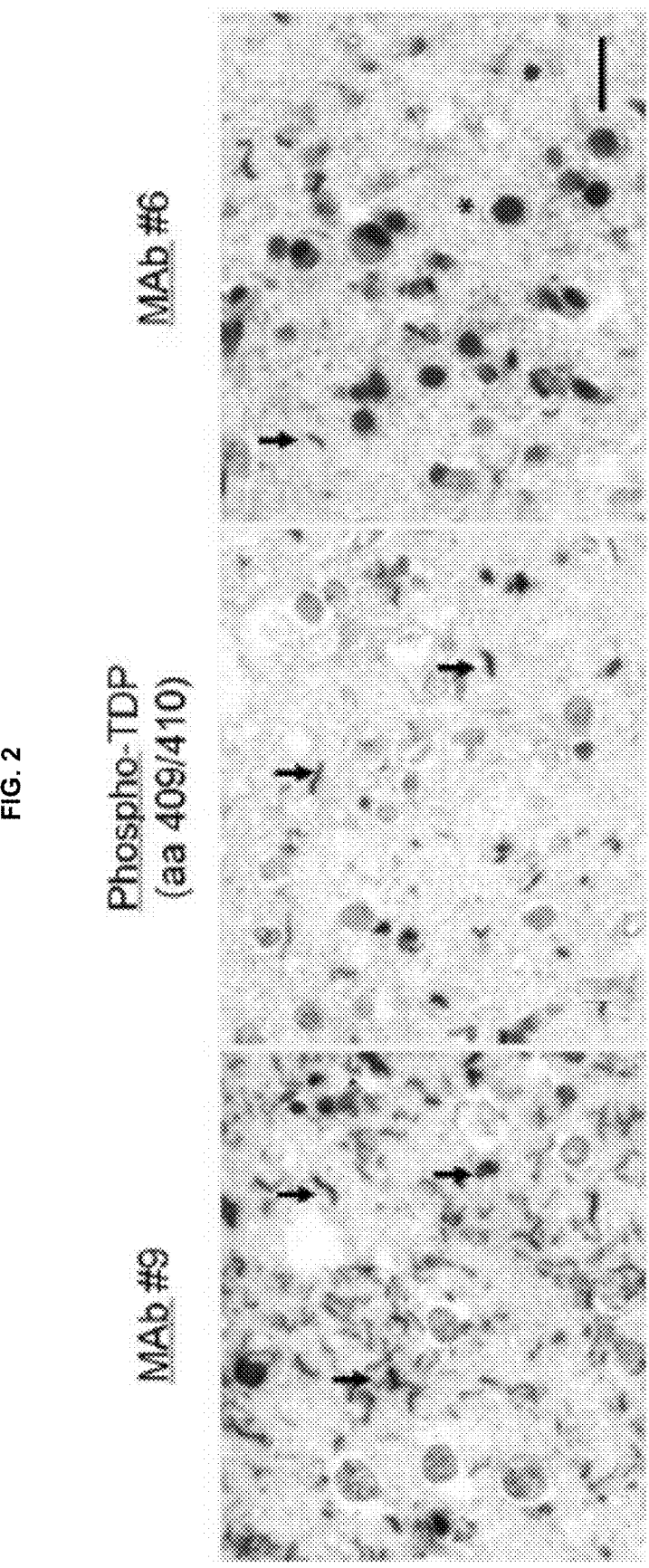
FIG. 2 is immunostaining images showing that MAb #9 preferentially recognizes pathologic TDP-43. MAb #9 robustly detects pathologic TDP-43 inclusions shown by the arrows with no or very minimal nuclear staining in the frontal cortex of an individual who suffered from FTLD. This was similar to a known antibody (aa 409/410) that is specific for phospho TDP-43. In contrast, MAb #6 recognizes both pathologic TDP-43 inclusions (arrows) and normal nuclear TDP-43 (asterisk) in the frontal cortex of an individual who suffered from FTLD. The scale bar is 20 μm.
Figure 3:
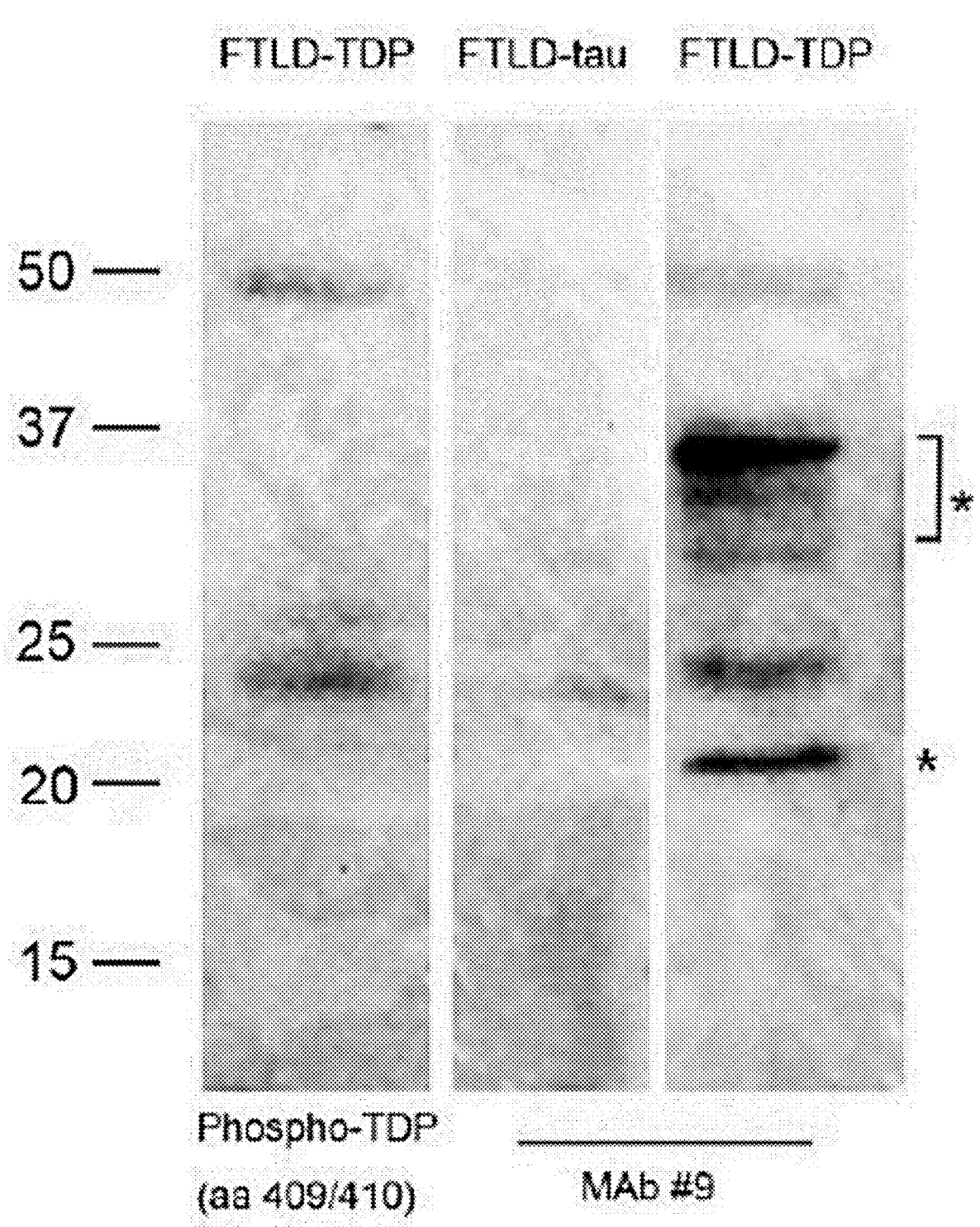
FIG. 3 is images of immunoblotting of CSF samples from subjects with FTLD-TDP and FTLD-tau using MAb #9 and 409/410 antibodies. MAb #9 revealed strong 20 kDa and 30-35 kDa fragments (shown by the asterisk) in FTLD-TDP subjects which are not seen when the 409/410 antibody was used.

The antibodies described above were tested in the brain tissue slices obtained from FTLD-TDP patients. MAbs #3 and #4 showed robust immunoreactivity for normal nuclear TDP-43 and minimal to weak reactivity for pathologic inclusions. MAb #6 was immunoreactive to both normal nuclear TDP-43 and pathologic inclusions. MAb #9 was strongly immunoreactive to all forms of pathological TDP-43 inclusions, with minimal reactivity for normal TDP-43 (FIG. 2). Immunoblotting analyses of urea soluble extracts from human FTLD-TDP brain tissues showed that MAbs #3 and #4 recognized full-length TDP-43 but not the C-terminal fragments of TDP-43, while MAb #6 recognized both. Moreover, MAbs #3 and #4 also did not detect the pathologic hyperphosphorylated 45 kDa band nor the high molecular weight smears, which were detected by MAb #6. Notably, MAb #9 only showed reactivity to pathologic TDP-43 species, with minimal reactivity to normal full-length TDP-43, which indicates that it is specific to pathologic TDP-43. Immunoblotting analyses of CSF from FTLD-TDP patients with MAb #9 showed similar results (FIG. 3).

Example 4

MAb #9 is Specific for Pathologic TDP-43

MAb #9 is unique from all reported MAbs that are specific for C-terminal TDP-43. Consistently until now, studies have shown that all C-terminal TDP-43-specific antibodies are immunoreactive not only to pathologic TDP-43 but also to normal nuclear TDP-43 (Feneberg et al., Mol Neurobiol. 2018; 55 (10): 7789-801). However, MAb #9 as described herein displayed high reactivity to pathologic TDP-43 inclusions, in the absence of significant reactivity to normal nuclear TDP-43 (FIG. 2). The underlying reason for this phenomenon is unknown, but it is likely due to the fact that MAb #9 recognizes an epitope that is only selectively exposed in pathologic TDP-43. This ability of MAb #9 to preferentially detect pathologic TDP-43 inclusions, with minimal or no normal nuclear TDP-43 immunohistochemical staining, is similar to the staining pattern seen with pathologic phospho-TDP-43-specific MAbs, such as the p409/410 MAb. However, MAb #9 appeared even more sensitive and was able to reveal a greater degree of pathology in different brain regions of FTLD-TDP patients compared to p409/410 MAb (FIG. 2). In addition, the TDP-43 pathology load revealed by MAb #9 is closely related to the severity of local neuronal loss, which was not reliably seen in studies using the p409/410 MAb. Interestingly, immunoblotting analyses of CSF samples from FTLD-TDP patients with MAb #9 revealed strong 20 kDa and 30-35 kDa fragments, which are rarely observed in brain tissues of human FTLD-TDP patients, in addition to the 45 kDa and 25 kDa fragments that were also revealed by p409/410 MAb (FIG. 3).

Example 5

ELISA Studies

ELISA systems were established to detect both normal and pathologic TDP-43 with the MAbs described herein. For normal full-length TDP-43, first antibodies were screened for the best pair and then a sandwich ELISA was established using MAbs #3 and #4 as the capture and detection antibody, respectively. This platform showed that the lower limit of detection for human recombinant rTDP-43 (OriGene Technologies, Rockville, MD) was 25 µg/mL. Using this sensitive ELISA, the amount of TDP-43 in HEK293 cell lysates and supernatant was able to be quantified. Then, a sandwich ELISA was set up using MAbs #9 and #6 as the capture and detection antibody, respectively, for detecting pathologic TDP-43. Using this sensitive ELISA, the amount of TDP-43 in the CSF samples from human FTLD-TDP patients was quantified, with a lower limit of detection of 60 µg/mL. Thus, these ELISA systems, and especially the ELISA for detecting pathologic TDP-43, represent new and valuable tools for biomarker discovery and investigation, tools that may accelerate the diagnosis of FTLD-TDP, and may be useful for the screening and selection of FTLD-TDP patients for inclusion in clinical trials.

Example 6

Verification of TDP-43 ELISA System with Tandem Mass Spectrometry

Tandem mass spectrometry (MS)-based proteomic analysis will be performed to: determine amino acid sequence of the pathologic form of TDP-43 detected by MAbs #9; perform large-scale relative quantitative proteomic analysis of pathologic TDP-43 across all 50 plasma and 30 CSF samples from FTLD-Tau, FTLD-TDP-43, AD, and age matched controls; and quantify the absolute level of pathologic TDP-43 in a subset of the plasma and CSF samples. For the experiment aimed to determine the relative quantification of plasma and CSF TDP-43 it is expected that compelling discovery-based quantitative results showing that all or nearly all the FTLD-TDP-43 cases have significantly elevated levels of pathologic TDP-43 will be obtained.

Figure 4:
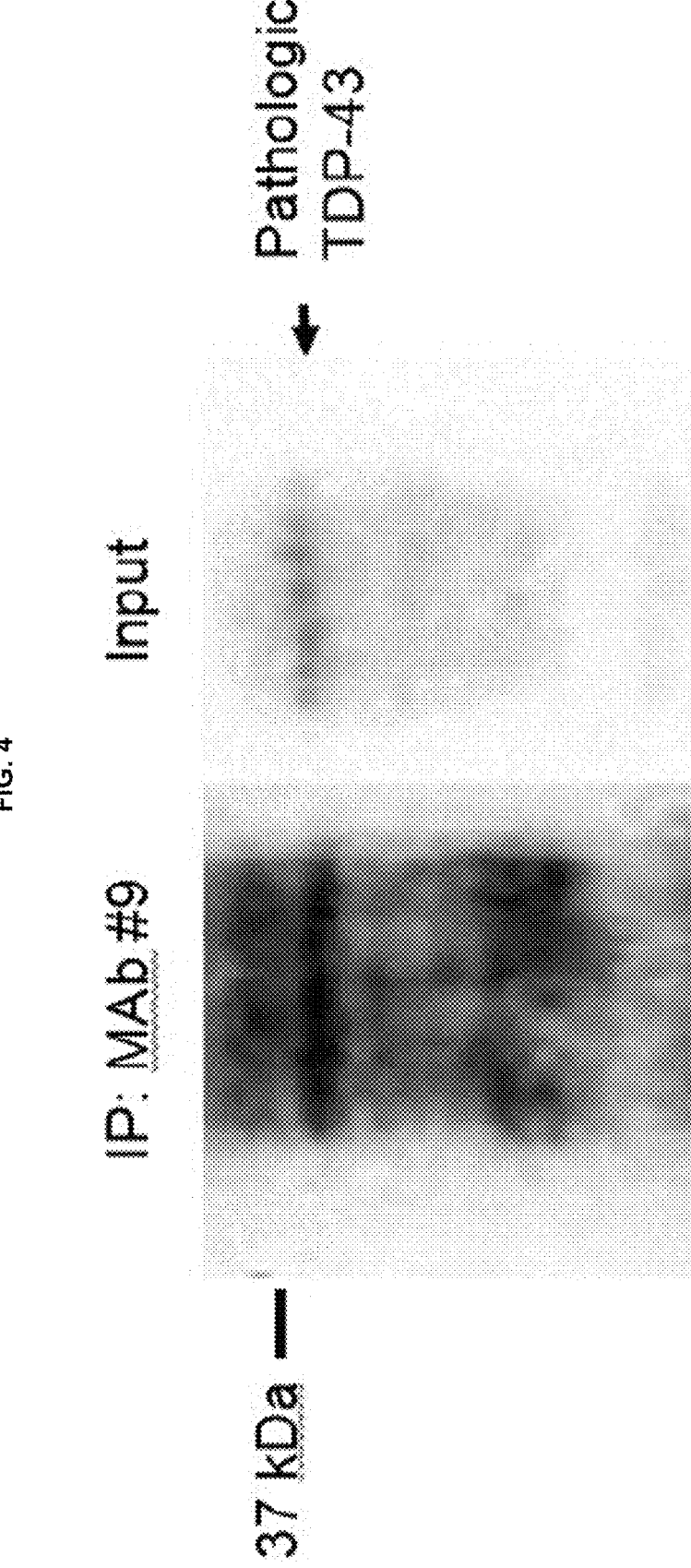
FIG. 4 is images of immunoprecipitation of pathologic TDP-43 from CSF of a subject who suffered from FTLD-TDP using MAb #9.

Preliminary data showed that MAb #9 was useful for immunoprecipitation (IP) for pathologic TDP-43 (FIG. 4). The TDP-43 IP will be further optimized using MAb #9. The recovery of TDP-43 will be assessed with Western blots (WBs) and the purity will be assessed with silver staining. Large batches of MAb #9 will be coupled to Dynabeads M-270 Epoxy beads (i.e., 2.8 µm superparamagnetic beads with surface exposed epoxy groups). By covalently coupling the primary amino and sulfhydryl groups in antibodies to the beads, the amount of IgG protein present in the purified material will be limited. The efficiency of antibody/bead coupling will be assessed by SDS-PAGE using silver staining and WB. In these initial experiments the amount of antibody and input plasma/CSF for robust purification of pathologic TDP-43 will also be optimized. With this knowledge in hand, pathologic TDP-43 will be immunoprecipitated with MAb #9 from plasma and CSF and the purified proteins will be resolved with SDS-PAGE. Next, a gel slice will be excised at 30-45 kDa to reduce sample complexity and increase the likelihood that mass spectrometry can characterize the complete amino acid composition of pathologic TDP-43. To increase sequence coverage of TDP-43, parallel in-gel digestion with several proteases including trypsin, Lys-C, Glu-C, Asp-N, and Lys-N will be performed.

The peptides will be separated, analyzed, identified, and mapped to reference TDP-43 amino acid sequence from Uniprot or NCBI (Savas et al., Science. 2012; 335 (6071): 942; Jha et al., Nature. 2017; 546 (7660): 651-5). Briefly, the peptides will be autosampler-loaded onto a C18 vented trap/analytical column assembly and separated with a Rapid Separation Liquid Chromatography (RSLC) ultra-high pressure nano-flow liquid chromatography system (Thermo Fisher, Waltham, MA). The intact peptides will be electrosprayed into the gas phase by applying a voltage to a stainless steel emitter tip directly into a Orbitrap Fusion Tribrid mass spectrometer. To analyze the proteomic data, ProLuCID (Xu et al., J Proteomics. 2015 Nov. 3; 129:16-24), DTASelect (Tabb et al., Journal of Proteome Research, 2002, 1 (1), pp 21-26), and Census (Park et al., 2014.

Bioinformatics. 30 (15): 2208-9; Park et al., 2008. Nature methods 5, 319-322) bioinformatic analysis software within the IP2 environment (integratedproteomics.com) will be used. To further interrogate the data, Skyline (MacCoss Lab, University of Washington) will be used. These software packages will be used and allow for identification of peptides and proteins and control the 1% false discovery rate based on the target decoy strategy. These software packages also allow for quantification of peptide abundance relative to the heavy-labeled internal standards based on the area under the curve from reconstructed chromatograms.

In the next experiment the reliability of the ELISA results will be tested with unbiased MS analysis. In these experiments a leading analytical workflow based on isobaric tandem mass tags (TMT) and multinotch MS3 analysis will be used (He et al., Mol Psychiatry. 2019; 24 (11): 1732-47). Specifically, large-scale relative quantitative proteomic analysis of pathologic TDP-43 levels across all 50 plasma and 30 CSF samples from FTLD-Tau, FTLD-TDP-43, AD, and age matched controls will be performed. The goal here is to confirm the ELISA based clear results that can easily differentiate the FTLD-TDP samples from the others based on elevated levels of pathologic TDP-43.

Each patient derived sample (plasma or CSF) will be subjected to IP with Mab #9 using the conditions determined above. The purified material will be denatured with 6 M guanidine hydrochloride, reduced, alkylated, and digested to peptides with trypsin and LysC proteases. The peptides will be purified with reverse phase resin and chemically labeled with one TMT tags. 16plex TMT reagent (Thermo Fisher, Waltham, MA) will be used and in each MS analysis run 4 FTLD-Tau, 4 FTLD-TDP, 4 AD, and 4 age matched controls will be combined. In total at least 13×16plex experiments for plasma and 8×16plex experiments for CSF will be performed. The peptides will be identified and relative quantification will be performed with the bioinformatic analysis software described above.

In the final experiment, the absolute abundance of pathologic TDP-43 will be measured in a subset of the plasma and CSF samples. The goal here is to obtain orthogonal MS based measures to compare and confirm those obtained with ELISA. While the precise measures obtained with MS may not be highly correlated to those from ELISA, it is expected that the measures and the trends will be similar.

The first step will be to affinity purify pathologic TDP-43 with MAb #9 and digest the purified material with trypsin. Next, at least 3 chemically synthesized SpikeTide TQL peptides containing a single heavy C-terminal arginine residue (JPT Peptide Technologies GmbH, Berlin, Germany) will be spiked in. SpikeTide TQL peptides are strategic since they are quantified using a proprietary Quanti-Tag. Peptides are released from tag by trypic digestion and aliquoted at 0.5 nM. These peptides will be spiked into the peptide mixtures at 5 different concentrations and purified with C18 Ziptips in to obtain a standard curve. The purified peptide concentrated using a SpeedVac vacuum concentrator (Labconco Corporation, Kansas City, MO), and analyzed by LC-MS/MS with a 2- or 4-hour analysis runs with an Orbitrap Fusion MS. The resulting spectra will be extracted, searched, and quantified with Prolucid/Sequest DTASelect and Census. The reconstructed MS1 chromatograms (area under the curves relative to the know amount of heavy peptide spiked into the sample) were used to determine the absolute peptide quantities.

It is anticipated that the proposed studies will objectively cross-verify the data from the ELISA. The quality of the CSF/plasma samples may vary depending on the patient's end stage condition; hence, the CSF/plasma samples will be cleaned up by immunoprecipitation using the specific MAb against pathologic TDP-43.

The ELISA system described herein will be transformed into a multiplex, Meso Scale Discovery (MSD)-based immunoassay (Meso Scale Diagnostics, LLC, Rockville, MD) that also includes other major dementia biomarkers, such as AD signature markers (A$\beta$42, T-tau, and P-tau181P), PGRN, and neurofilament light (NfL) subunit, for the diagnosis and follow-up of dementia-related diseases. Using MSD-based immunoassay, the sensitivity of a previous PGRN ELISA was increased from 60 ng/ml to 9 µg/ml. In addition to higher sensitivity (Constantine et al., J Virol Methods. 1994; 47 (1-2): 153-64; Kuhle et al., Clin Chem Lab Med. 2016; 54 (10): 1655-61; Tatebe et al., Mol Neurodegener. 2017; 12 (1): 63; Kuhle et al., Mult Scler. 2016; 22 (12): 1550-9), an MSD-based immunoassay also has the advantage of being quicker, requiring less sample volume to run, as well as having better reproducibility and precision.

Example 7

Determination of Whether Plasma Pathologic TDP-43 Levels Reflect the Severity of Pathology in FTLD-TDP Brains Brain pathology will be quantified by measuring neuronal loss and gliosis and TDP-43 pathology burden, and this will elucidate the correlation between severity of brain pathology and plasma pathologic TDP-43 levels in FTLD-TDP patients. In addition to the plasma and CSF specimens of the above Examples, hematoxylin & eosin (H&E) slides and paraffin blocks of brain tissue from different brain regions from patients with FTLD-TDP will be obtained from the brain banks and analyzed.

It will be determined if plasma and CSF pathologic TDP-43 is a sensitive and specific biomarker for disease progression in FTLD-TDP. Using the novel ELISA described herein, the pathologic TDP-43 levels will be measured in the plasma/CSF of FTLD-TDP patients at early, middle, and late stages, and it will be determined if the plasma/CSF pathologic TDP-43 levels increase as the disease progresses. If this is true, plasma/CSF pathologic TDP-43 levels could be valuable for monitoring disease progression and evaluating treatment effectiveness.

If the plasma pathologic TDP-43 level reflects the severity of pathology in FTLD-TDP brains, plasma pathologic TDP-43 levels could further be used as a biomarker to monitor disease progression of FTLD-TDP and monitor the effectiveness of treatments for this disease. It is hypothesized that the worse neuronal loss and gliosis and/or TDP-43 pathology burden will be observed in the FTLD-TDP brain, and a higher the pathologic TDP-43 level will be observed in the plasma from patients with the most severe disease.

This study will include a subset of FTLD-TDP patients (n=30) that have both plasma/CSF and brain tissue (H&E slides and paraffin blocks of different brain regions) available. To semi quantify brain pathology, the frontal cortex and hippocampus of FTLD-TDP cases will be examined for neuronal loss and gliosis, as well as for TDP-43 burden. Neuronal loss and gliosis will be assessed on H&E-stained slides and will be graded as 0=none, 1=mild, 2=moderate, or 3=severe. An average score for neuronal loss/gliosis will be obtained from both brain regions. TDP-43 burden will be assessed on the frontal cortical and hippocampal sections immunostained with MAb #9. The overall TDP-43 burden will be graded on the same scale as that used for neuronal loss and gliosis, i.e., 0=none, 1=mild, 2=moderate, or 3=severe. Similarly, an average score for TDP-43 burden will be obtained from both brain regions. A linear model and generalized linear model, depending on the distribution of outcome, will be used with the plasma TDP-43 level as the covariate and the neuronal loss/gliosis or TDP-43 pathology burden as the outcome. Similar analyses will be performed using the CSF TDP-43 level as the covariate. The regression parameters using plasma or CSF TDP-43 levels will also be compared.

It is expected that the plasma pathologic TDP-43 level will reflect the pathology severity of FTLD-TDP brains. Plasma pathologic TDP-43 levels might show close correlation with either the severity of neuronal loss and gliosis or TDP-43 pathology burden, or both. The CSF pathologic TDP-43 level may show a closer correlation with brain pathology than the plasma pathologic TDP-43 level, which will be reassuring and will help validate plasma pathologic TDP-43 as a biomarker. There is a possibility that brain pathology and plasma pathologic TDP-43 levels show no obvious correlation. If this is the case, the FTLD-TDP brains will be divided into three groups based on their histopathologic type A, B, and C and brain pathology will be correlated with plasma pathologic TDP-43 levels separately for each group (FTLD-TDP type D is so rare, there are too few cases available for evaluation).

Example 8

A Novel MAb Against Human Pathologic TDP-43

Figures 5A, 5B:
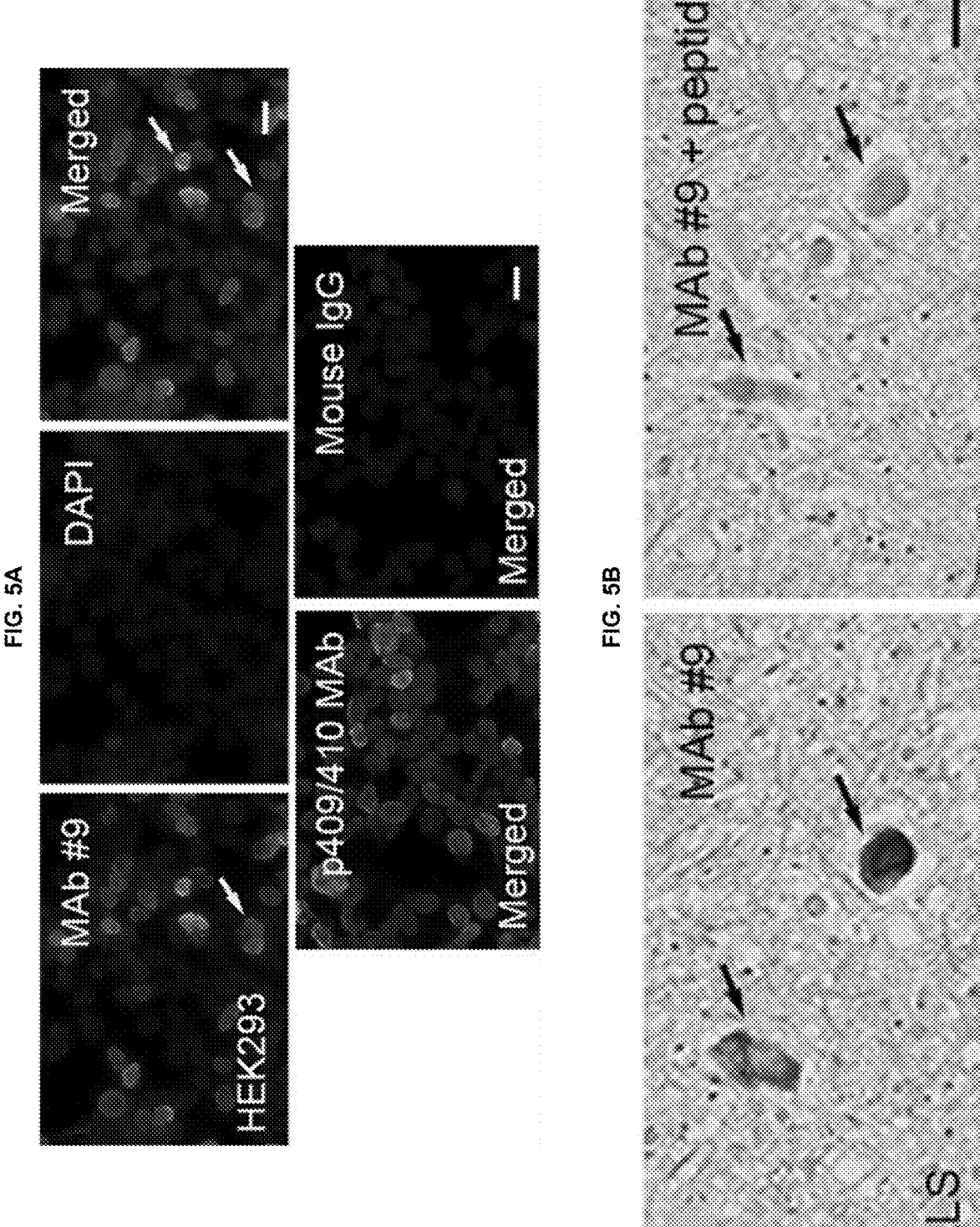
FIGS. 5A-5B show immunofluorescent and immunostaining images to analyze the specificity of MAb #9.

New TDP-43 MAbs were generated to develop a disease-specific biomarker of TDP-43 pathology. Murine MAbs were raised against human recombinant TDP-43. More than 5,000 MAb clones were screened by indirect enzyme-linked immunosorbent assay (ELISA). Promising MAbs were then tested by immunohistochemistry with brain samples from FTLD-TDP patients. Most of these antibodies showed robust immunoreactivity for normal nuclear TDP-43 and weak to strong reactivity for pathologic inclusions—except for MAb #9. MAb #9, whose epitope region is at the C-terminus, aa280-300, was strongly immunoreactive to all forms of pathologic TDP-43 inclusions, with minimal reactivity for normal TDP-43. The specificity of MAb #9 was further confirmed using HEK293 cells transfected with TDP-43-expressing plasmid and an absorption test (FIGS. 5A-5B).

Figure 6A:
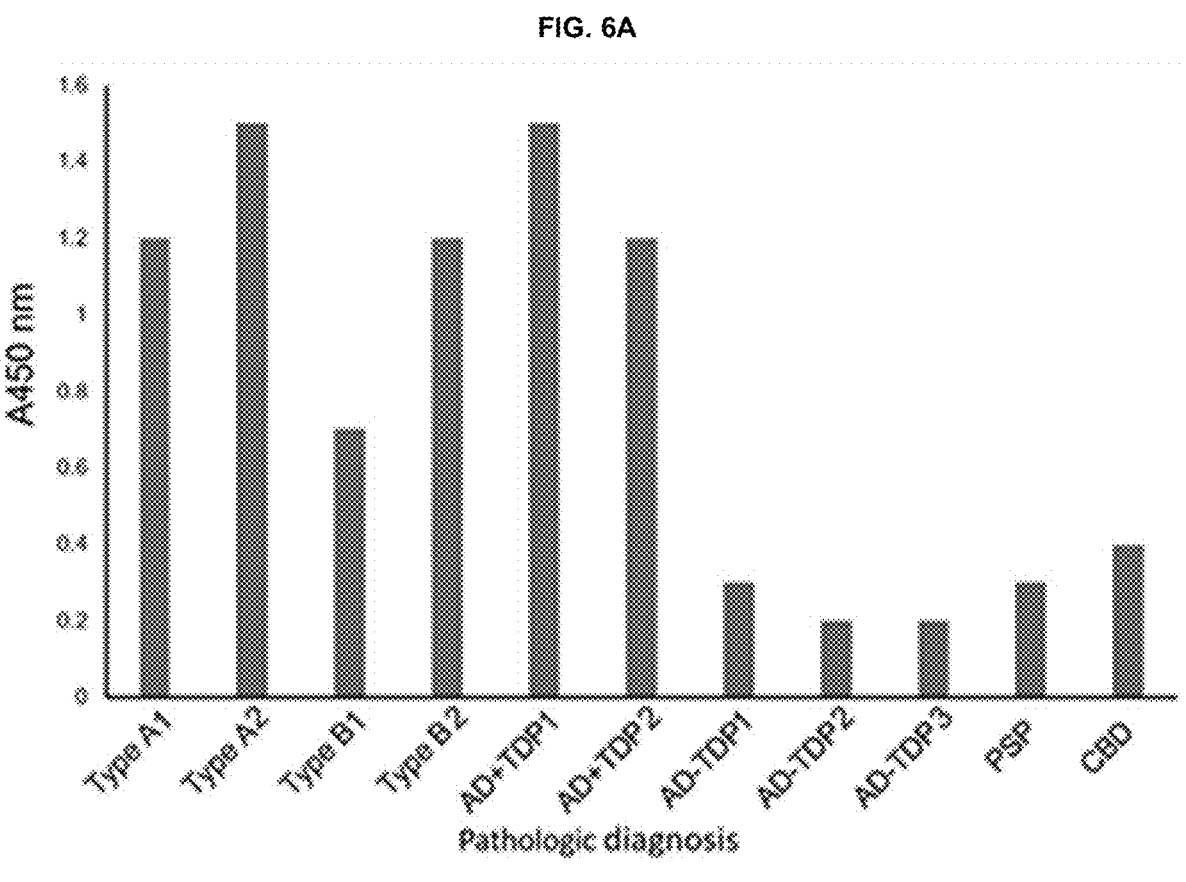
FIGS. 6A-6B show that MAb #9 detects pathologic TDP-43 in plasma.
Figure 6B:
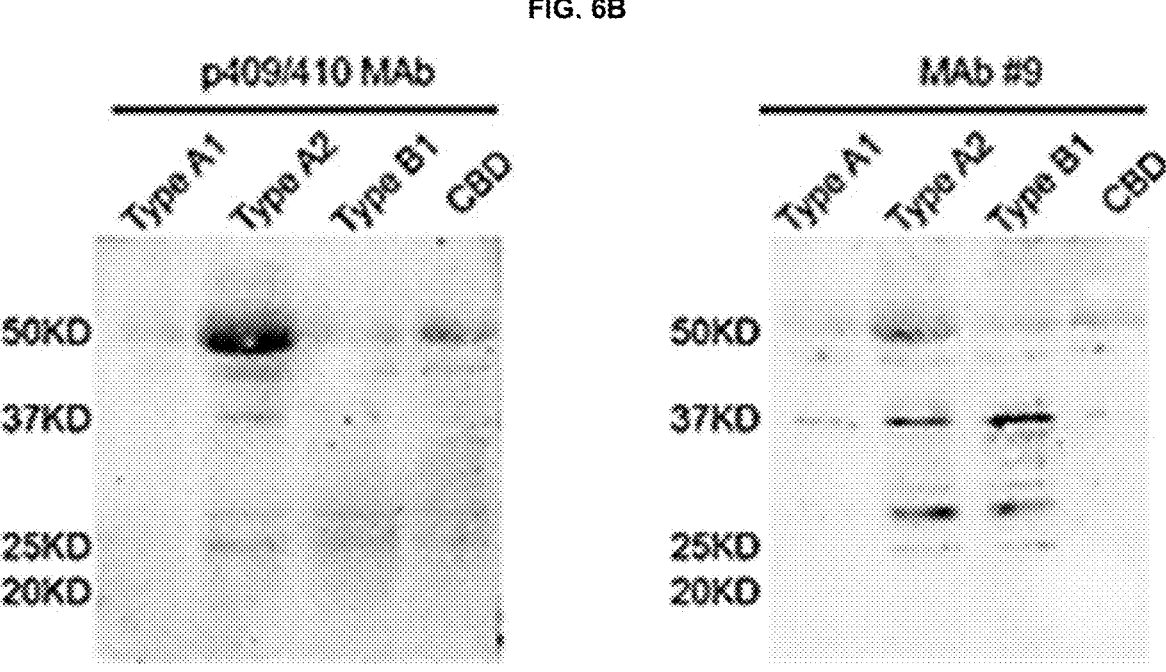

Interestingly, a sandwich ELISA using MAb #9 and another MAb (MAb #4) against the C-terminus of TDP-43 showed promise for detecting pathologic TDP-43 levels in the plasma (FIG. 6A) and CSF from patients of FTLD-TDP, and AD with TDP pathology. Thus, this ELISA system represents new and valuable tool for biomarker investigation and discovery, and may prove useful in accelerating TDP-43 proteinopathy diagnoses and/or selecting TDP-43 patient for clinical trials of new therapeutic agents. Western blot with MAb #9 on some plasma samples (FTLD-type A1, -type A2, -type B1, and CBD (corticobasal degeneration) in FIG. 6A) revealed a different band pattern compared to that with the control antibody, p409/410 MAb (Cosmo Bio USA, Inc., Carlsbad, CA; FIG. 6B). Specifically, MAb #9 revealed stronger bands of 35 kDa than the p409/410 MAb, though both antibodies revealed the typical 45 and 25 kDa bands of pathologic TDP-43. It is worth noting that the 35 kDa TDP-43 fragment, though it has been reported in ALS, has rarely been seen in human tissue.

Figure 7A:
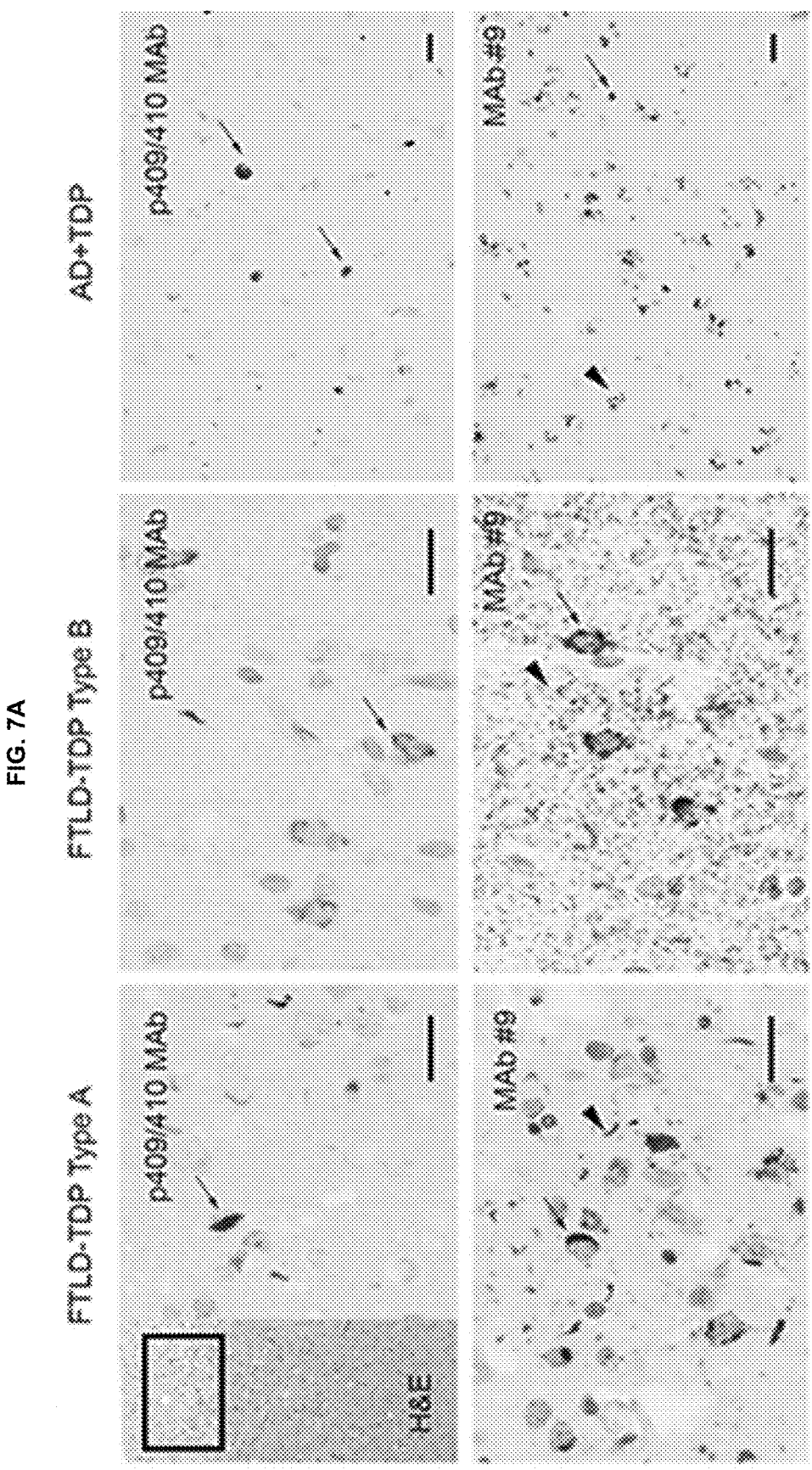
FIGS. 7A-7C show that MAb #9 detects a novel TDP-43 pathology.
Figure 7B:
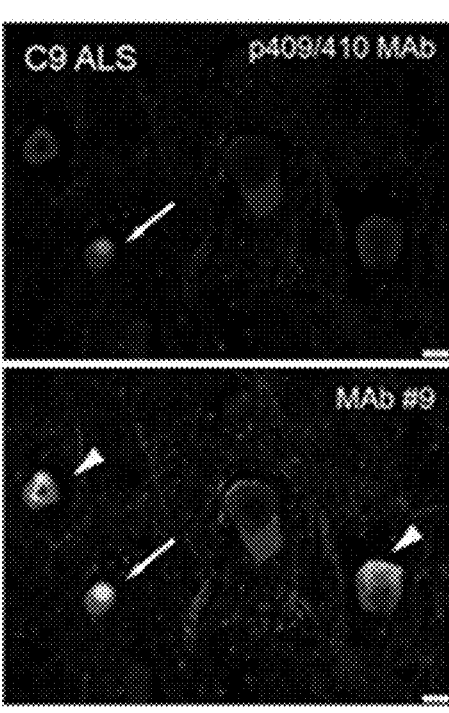
Figure 7C:
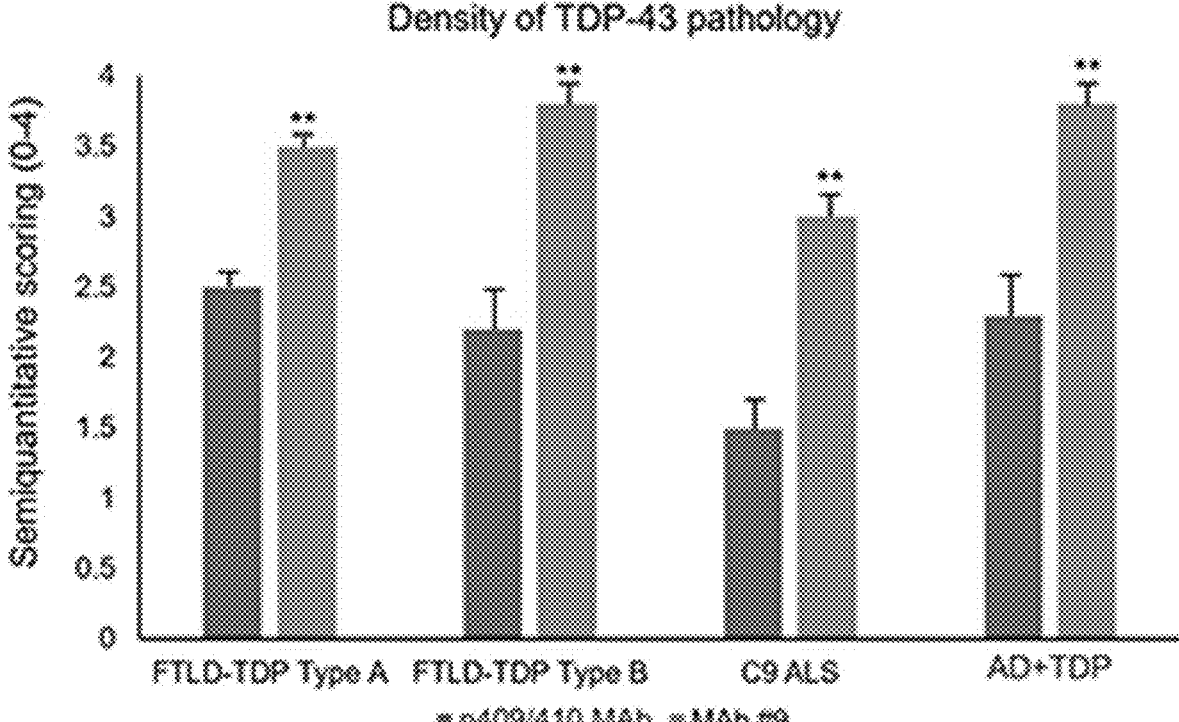
Figure 8:
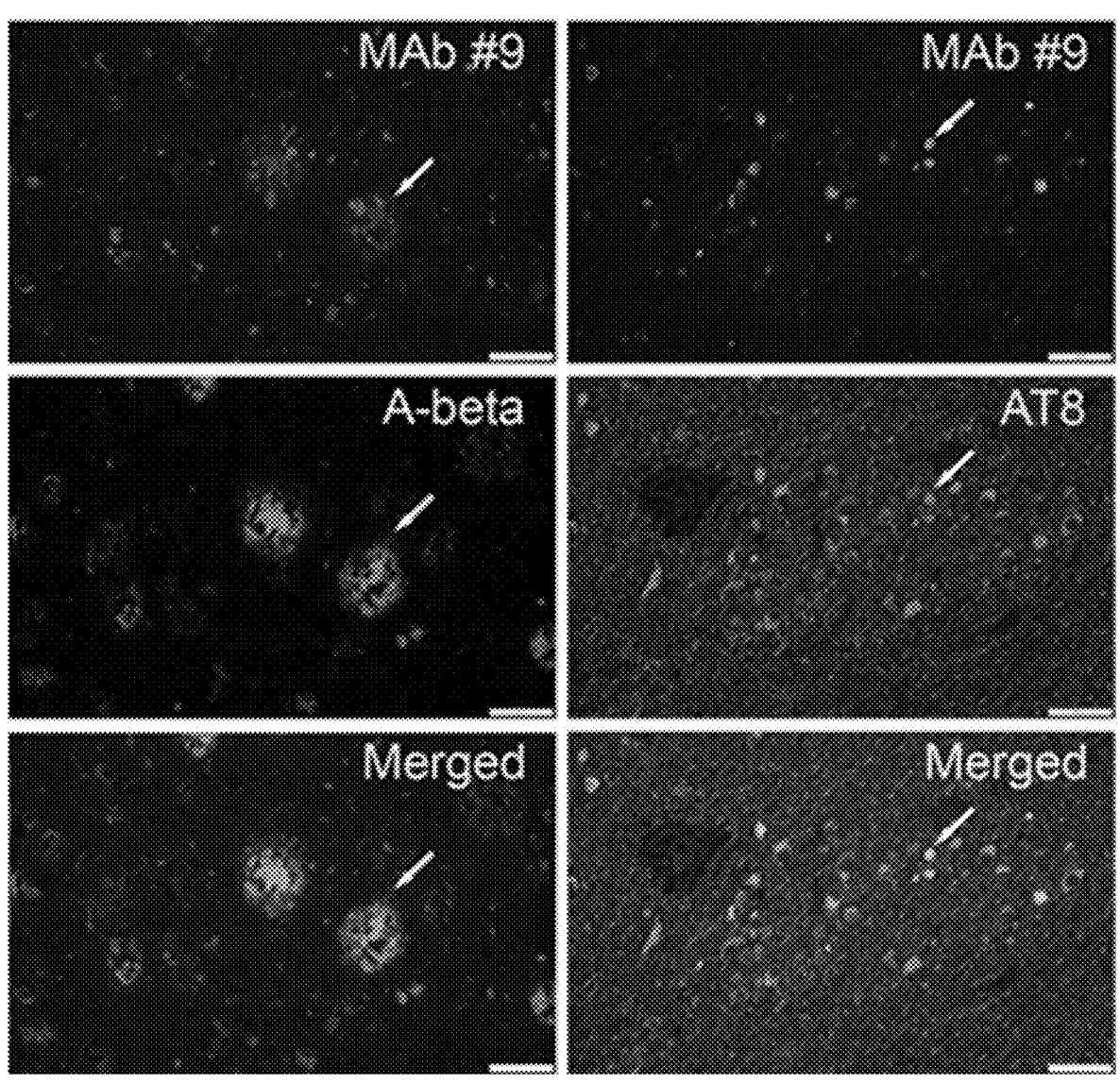
FIG. 8 is images of immunofluorescent staining showing MAb #9-immunopositivity (cy3, orange) is co-localized (arrows) with beta-amyloid (FITC, green), which has not been reported before, and tau (FITC, green) in the amygdala of a subject who suffered from AD with TDP pathology brain. The scale bar is 50 μm.

This ability of MAb #9 to preferentially detect pathologic TDP-43 inclusions is similar to that seen with phospho-TDP-43-specific MAbs, such as the p409/410 MAb, as evidenced by similar staining patterns (FIGS. 7A-7B). However, MAb #9 was more sensitive and could reveal an overall greater degree of TDP-43 pathology than the p409/410 MAb (FIG. 7C). Specifically, MAb #9 could reveal more fine neurites in the frontal cortex of FTLD-TDP type A brains, and could reveal dense fine neurites in the frontal cortex of type B brains that are rarely revealed by the p409/410 MAb (FIG. 7A). In addition, the density of TDP-43-positive fine neurites revealed by MAb #9 was closely related to the severity of local neuronal loss (FIG. 7A), which was not reliably seen in studies using the p409/410 MAb (Feneberg et al., Mol Neurobiol. 2018; 55 (10): 7789-801; Goossens et al., Acta Neuropathol Commun. 2015; 3:15; Kawles et al., Brain. 2021). Interestingly, MAb #9 also revealed novel TDP-43 inclusions in cases of AD with medial temporal TDP-43 pathology (FIG. 7A and FIG. 8).

Example 9

Novel ELISA for Quantifying TDP-43

Figure 9:
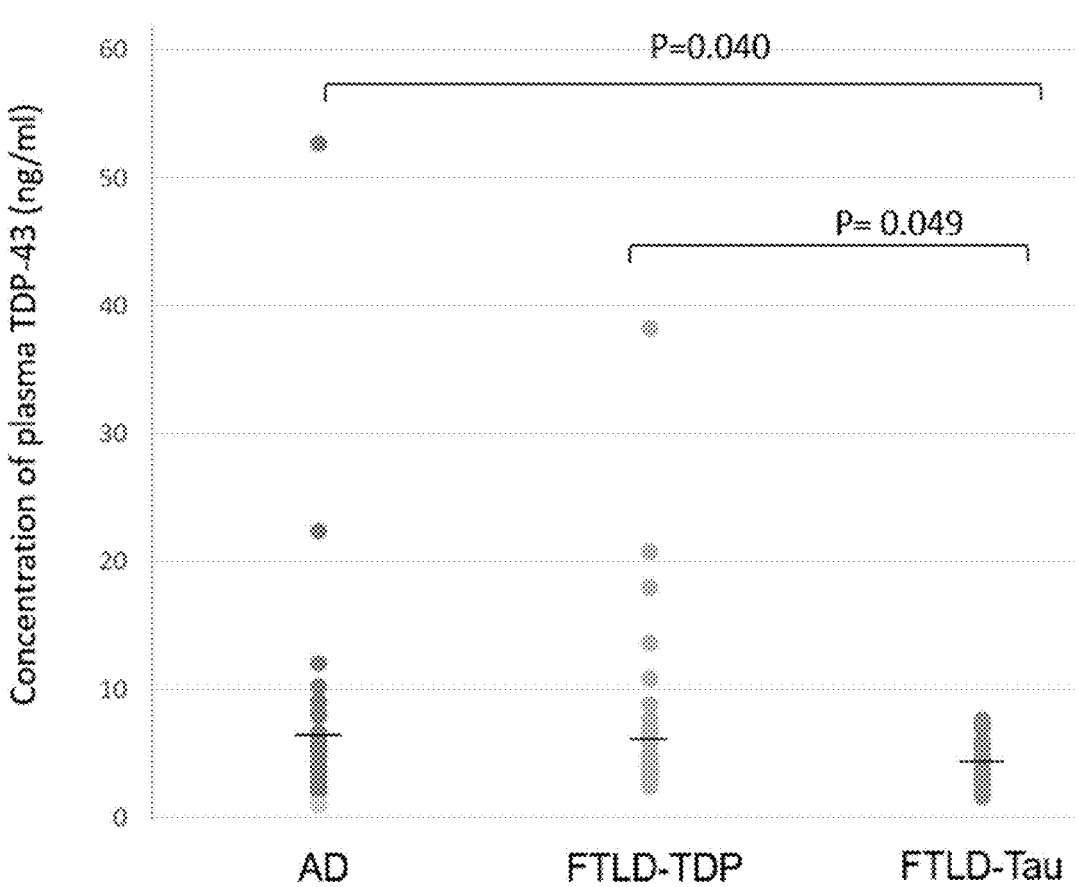
FIG. 9 is a scatter dot plot showing TDP-43 levels in plasma from subjects who suffered from FTLD-TDP (n=35), FTLD-Tau (n=34), and AD (n=22). The comparisons between TDP-43 concentration distribution were calculated by the Mann-Whitney U test. The median of plasma TDP-43 concentrations were 5.8, 5.4, and 4.0 ng/ml in AD, FTLD-TDP, and FTLD-Tau subjects.

An ELISA was developed for quantifying TDP-43 levels by using the best antibody pair, MAb #9 and MAb #4. MAb #4 was used as the capture antibody, and MAb #9 was used as the detection antibody. After screening by checkerboard titration followed by ELISA, the optimal concentrations of capture MAb #4 was 0.5 µg/mL and that of the detection MAb #9 was 1:2000. Then the standard dose-response curve for TDP-43 was established by using the two-fold serially diluted recombinant rTDP-43 protein (OriGene Technologies, Rockville, MD). BSA was used to establish the baseline. Human plasma samples from 35 FTLD-TDP, 34 FTLD-Tau, and 22 AD patients were used for quantifying TDP-43 levels using the established ELISA system (FIG. 9).

The foregoing description of the specific aspects will so fully reveal the general nature of the invention that others can, by applying knowledge within the skill of the art, readily modify and/or adapt for various applications such specific aspects, without undue experimentation, without departing from the general concept of the present disclosure. Therefore, such adaptations and modifications are intended to be within the meaning and range of equivalents of the disclosed aspects, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present disclosure should not be limited by any of the above-described exemplary aspects, but should be defined only in accordance with the following claims and their equivalents.

All publications, patents, patent applications, and/or other documents cited in this application are incorporated by reference in their entirety for all purposes to the same extent as if each individual publication, patent, patent application, and/or other document were individually indicated to be incorporated by reference for all purposes.

For reasons of completeness, various aspects of the invention are set out in the following numbered clauses:

Clause 1. An antibody or antigen-binding fragment thereof comprising an immunoglobulin heavy chain (HC) variable domain sequence and an immunoglobulin light chain (LC) variable domain sequence, wherein: (a) the immunoglobulin HC variable domain sequence comprises (i) an HC CDR1 comprising the amino acid sequence of SEQ ID NO: 4, (ii) an HC CDR2 comprising the amino acid sequence of SEQ ID NO: 5, and (iii) an HC CDR3 comprising the amino acid sequence of SEQ ID NO: 6; and (b) the immunoglobulin LC variable domain sequence comprises (i) an LC CDR1 comprising the amino acid sequence of SEQ ID NO: 8, (ii) an LC CDR2 comprising the amino acid sequence of SEQ ID NO: 9, and (iii) an LC CDR3 comprising the amino acid sequence of SEQ ID NO: 10.

Clause 2. The antibody or antigen-binding fragment thereof of clause 1, wherein the immunoglobulin HC variable domain sequence comprises the amino acid sequence of SEQ ID NO: 3; and the immunoglobulin LC variable domain sequence comprises the amino acid sequence of SEQ ID NO: 7.

Clause 3. An antibody or antigen-binding fragment thereof comprising an immunoglobulin heavy chain (HC) variable domain sequence and an immunoglobulin light chain (LC) variable domain sequence, wherein: (a) the immunoglobulin HC variable domain sequence comprises (i) an HC CDR1 comprising the amino acid sequence of SEQ ID NO: 12, (ii) an HC CDR2 comprising the amino acid sequence of SEQ ID NO: 13, and (iii) an HC CDR3 comprising the amino acid sequence of SEQ ID NO: 14; and (b) the immunoglobulin LC variable domain sequence comprises (i) an LC CDR1 comprising the amino acid sequence of SEQ ID NO: 16, (ii) an LC CDR2 comprising the amino acid sequence of SEQ ID NO: 17, and (iii) an LC CDR3 comprising the amino acid sequence of SEQ ID NO: 18.

Clause 4. The antibody or antigen-binding fragment thereof of clause 3, wherein the immunoglobulin HC variable domain sequence comprises the amino acid sequence of SEQ ID NO: 11; and the immunoglobulin LC variable domain sequence comprises the amino acid sequence of SEQ ID NO: 15.

Clause 5. An antibody or antigen-binding fragment thereof comprising an immunoglobulin heavy chain (HC) variable domain sequence and an immunoglobulin light chain (LC) variable domain sequence, wherein: (a) the immunoglobulin HC variable domain sequence comprises (i) an HC CDR1 comprising the amino acid sequence of SEQ ID NO: 20, (ii) an HC CDR2 comprising the amino acid sequence of SEQ ID NO: 21, and (iii) an HC CDR3 comprising the amino acid sequence of SEQ ID NO: 22; and (b) the immunoglobulin LC variable domain sequence comprises (i) an LC CDR1 comprising the amino acid sequence of SEQ ID NO: 24, (ii) an LC CDR2 comprising the amino acid sequence of SEQ ID NO: 25, and (iii) an LC CDR3 comprising the amino acid sequence of SEQ ID NO: 26.

Clause 6. The antibody or antigen-binding fragment thereof of clause 5, wherein the immunoglobulin HC variable domain sequence comprises the amino acid sequence of SEQ ID NO: 19; and the immunoglobulin LC variable domain sequence comprises the amino acid sequence of SEQ ID NO: 23.

Clause 7. The antibody or antigen-binding fragment thereof of any one of clauses 1-6, wherein the immunoglobulin heavy chain variable region and the immunoglobulin light chain variable region together bind at least a portion of TAR DNA-binding protein 43 (TDP-43; SEQ ID NO: 1).

Clause 8. The antibody or antigen-binding fragment thereof of any one of clauses 1-7, wherein the immunoglobulin heavy chain variable region and the immunoglobulin light chain variable region together bind at least a portion of SEQ ID NO: 2.

Clause 9. An isolated nucleic acid comprising a nucleotide sequence encoding the antibody or antigen-binding fragment thereof of any one of clauses 1-8.

Clause 10. Use of one or more of the antibodies or antigen-binding fragments thereof of any one of clauses 1-8 to prescreen a subject for a clinical trial.

Clause 11. An immunoassay comprising one or more of the antibodies or antigen-binding fragments thereof of any one of clauses 1-8.

Clause 12. A method of detecting TAR DNA-binding protein 43 (TDP-43; SEQ ID NO: 1) in a biological sample, the method comprising: contacting the sample with an antibody or antigen-binding fragment thereof, wherein the antibody or antigen-binding fragment comprises an immunoglobulin heavy chain (HC) variable domain sequence and an immunoglobulin light chain (LC) variable domain sequence, wherein: (a) the immunoglobulin HC variable domain sequence comprises (i) an HC CDR1 comprising the amino acid sequence of SEQ ID NO: 4, (ii) an HC CDR2 comprising the amino acid sequence of SEQ ID NO: 5, and (iii) an HC CDR3 comprising the amino acid sequence of SEQ ID NO: 6; and (b) the immunoglobulin LC variable domain sequence comprises (i) an LC CDR1 comprising the amino acid sequence of SEQ ID NO: 8, (ii) an LC CDR2 comprising the amino acid sequence of SEQ ID NO: 9, and (iii) an LC CDR3 comprising the amino acid sequence of SEQ ID NO: 10.

Clause 13. The method of clause 12, wherein the method further comprises contacting the sample with a second antibody or antigen-binding fragment thereof, wherein the second antibody or antigen-binding fragment comprises an immunoglobulin HC variable domain sequence and an immunoglobulin LC variable domain sequence, wherein: (a) the immunoglobulin HC variable domain sequence comprises (i) an HC CDR1 comprising the amino acid sequence of SEQ ID NO: 12, (ii) an HC CDR2 comprising the amino acid sequence of SEQ ID NO: 13, and (iii) an HC CDR3 comprising the amino acid sequence of SEQ ID NO: 14; and (b) the immunoglobulin LC variable domain sequence comprises (i) an LC CDR1 comprising the amino acid sequence of SEQ ID NO: 16, (ii) an LC CDR2 comprising the amino acid sequence of SEQ ID NO: 17, and (iii) an LC CDR3 comprising the amino acid sequence of SEQ ID NO: 18.

Clause 14. The method of clause 12, wherein the method further comprises contacting the sample with a second antibody or antigen-binding fragment thereof, wherein the second antibody or antigen-binding fragment comprises an immunoglobulin HC variable domain sequence and an immunoglobulin LC variable domain sequence, wherein: (a) the immunoglobulin HC variable domain sequence comprises (i) an HC CDR1 comprising the amino acid sequence of SEQ ID NO: 20, (ii) an HC CDR2 comprising the amino acid sequence of SEQ ID NO: 21, and (iii) an HC CDR3 comprising the amino acid sequence of SEQ ID NO: 22; and (b) the immunoglobulin LC variable domain sequence comprises (i) an LC CDR1 comprising the amino acid sequence of SEQ ID NO: 24, (ii) an LC CDR2 comprising the amino acid sequence of SEQ ID NO: 25, and (iii) an LC CDR3 comprising the amino acid sequence of SEQ ID NO: 26.

Clause 15. The method of any one of clauses 12-14, wherein the TDP-43 is misfolded.

Clause 16. The method of any one of clauses 12-15, wherein the sample comprises a cell or a tissue sample.

Clause 17. The method of any one of clauses 12-16, wherein the sample comprises plasma, serum, or cerebrospinal fluid (CSF).

Clause 18. The method of any one of clauses 12-17, wherein the sample is obtained from a subject that is diagnosed as having, suspected as having, or at risk of having or developing a neurodegenerative disease.

Clause 19. The method of clause 18, wherein the neurodegenerative disease is frontotemporal lobar degeneration (FTLD).

Clause 20. The method of any one of clauses 12-19, wherein the detection comprises one or more of immunohistochemistry (IHC), Meso Scale Discovery (MSD) biomarker assay, Western blotting, flow cytometry, radioimmunoassay (RIA), counting immunoassay (CIA), enzyme immunoassays (EIA) or enzyme-linked immunosorbent assays (ELISA), fluoroimmnoassay (FIA), or chemiluminescence immunoassay (CLIA).

Clause 21. A method of diagnosing a neurodegenerative disease in a subject, the method comprising detecting the presence of TAR DNA-binding protein 43 (TDP-43; SEQ ID NO: 1) in a biological sample from the subject, the method comprising: contacting the sample with an antibody or antigen-binding fragment thereof, wherein the antibody or antigen-binding fragment comprises an immunoglobulin heavy chain (HC) variable domain sequence and an immunoglobulin light chain (LC) variable domain sequence, wherein: (a) the immunoglobulin HC variable domain sequence comprises (i) an HC CDR1 comprising the amino acid sequence of SEQ ID NO: 4, (ii) an HC CDR2 comprising the amino acid sequence of SEQ ID NO: 5, and (iii) an HC CDR3 comprising the amino acid sequence of SEQ ID NO: 6; and (b) the immunoglobulin LC variable domain sequence comprises (i) an LC CDR1 comprising the amino acid sequence of SEQ ID NO: 8, (ii) an LC CDR2 comprising the amino acid sequence of SEQ ID NO: 9, and (iii) an LC CDR3 comprising the amino acid sequence of SEQ ID NO: 10; wherein the presence of TDP-43 is indicative of the subject having a neurodegenerative disease.

Clause 22. The method of clause 21, wherein the method further comprises contacting the sample with a second antibody or antigen-binding fragment thereof, wherein the second antibody or antigen-binding fragment comprises an immunoglobulin HC variable domain sequence and an immunoglobulin LC variable domain sequence, wherein: (a) the immunoglobulin HC variable domain sequence comprises (i) an HC CDR1 comprising the amino acid sequence of SEQ ID NO: 12, (ii) an HC CDR2 comprising the amino acid sequence of SEQ ID NO: 13, and (iii) an HC CDR3 comprising the amino acid sequence of SEQ ID NO: 14; and (b) the immunoglobulin LC variable domain sequence comprises (i) an LC CDR1 comprising the amino acid sequence of SEQ ID NO: 16, (ii) an LC CDR2 comprising the amino acid sequence of SEQ ID NO: 17, and (iii) an LC CDR3 comprising the amino acid sequence of SEQ ID NO: 18.

Clause 23. The method of clause 21, wherein the method further comprises contacting the sample with a second antibody or antigen-binding fragment thereof, wherein the second antibody or antigen-binding fragment comprises an immunoglobulin HC variable domain sequence and an immunoglobulin LC variable domain sequence, wherein: (a) the immunoglobulin HC variable domain sequence comprises (i) an HC CDR1 comprising the amino acid sequence of SEQ ID NO: 20, (ii) an HC CDR2 comprising the amino acid sequence of SEQ ID NO: 21, and (iii) an HC CDR3 comprising the amino acid sequence of SEQ ID NO: 22; and (b) the immunoglobulin LC variable domain sequence comprises (i) an LC CDR1 comprising the amino acid sequence of SEQ ID NO: 24, (ii) an LC CDR2 comprising the amino acid sequence of SEQ ID NO: 25, and (iii) an LC CDR3 comprising the amino acid sequence of SEQ ID NO: 26.

Clause 24. The method of any one of clauses 21-23, wherein the neurodegenerative disease is frontotemporal lobar degeneration (FTLD).

Clause 25. An immunoassay kit for selectively detecting TAR DNA-binding protein 43 (TDP-43; SEQ ID NO: 1) in a biological sample, the kit comprising: an antibody or antigen-binding fragment thereof, wherein the antibody or antigen-binding fragment comprises an immunoglobulin heavy chain (HC) variable domain sequence and an immunoglobulin light chain (LC) variable domain sequence, wherein: (a) the immunoglobulin HC variable domain sequence comprises (i) an HC CDR1 comprising the amino acid sequence of SEQ ID NO: 4, (ii) an HC CDR2 comprising the amino acid sequence of SEQ ID NO: 5, and (iii) an HC CDR3 comprising the amino acid sequence of SEQ ID NO: 6; and (b) the immunoglobulin LC variable domain sequence comprises (i) an LC CDR1 comprising the amino acid sequence of SEQ ID NO: 8, (ii) an LC CDR2 comprising the amino acid sequence of SEQ ID NO: 9, and (iii) an LC CDR3 comprising the amino acid sequence of SEQ ID NO: 10; and, a detection reagent.

Clause 26. The kit of clause 25, further comprising a solid support for the antibody or antigen-binding fragment thereof.

Clause 27. The kit of clause 25 or clause 26, further comprising a detection means.

Clause 28. The kit of clause 27, wherein the detection means is one or more of fluorescent, luminescent, radioactive, and colorimetric.

Clause 29. The kit of any one of clauses 25-28, wherein the detection reagent is one or more of colorimetric substrates, chemiluminescent substrates, and fluorescent substrates.

Clause 30. The kit of any one of clauses 25-29, further comprising a second antibody or antigen-binding fragment thereof, wherein the second antibody or antigen-binding fragment comprises an immunoglobulin HC variable domain sequence and an immunoglobulin LC variable domain sequence, wherein: (a) the immunoglobulin HC variable domain sequence comprises (i) an HC CDR1 comprising the amino acid sequence of SEQ ID NO: 12, (ii) an HC CDR2 comprising the amino acid sequence of SEQ ID NO: 13, and (iii) an HC CDR3 comprising the amino acid sequence of SEQ ID NO: 14; and (b) the immunoglobulin LC variable domain sequence comprises (i) an LC CDR1 comprising the amino acid sequence of SEQ ID NO: 16, (ii) an LC CDR2 comprising the amino acid sequence of SEQ ID NO: 17, and (iii) an LC CDR3 comprising the amino acid sequence of SEQ ID NO: 18.

Clause 31. The kit of any one of clauses 25-29, further comprising a second antibody or antigen-binding fragment thereof, wherein the second antibody or antigen-binding fragment comprises an immunoglobulin HC variable domain sequence and an immunoglobulin LC variable domain sequence, wherein: (a) the immunoglobulin HC variable domain sequence comprises (i) an HC CDR1 comprising the amino acid sequence of SEQ ID NO: 20, (ii) an HC CDR2 comprising the amino acid sequence of SEQ ID NO: 21, and (iii) an HC CDR3 comprising the amino acid sequence of SEQ ID NO: 22; and (b) the immunoglobulin LC variable domain sequence comprises (i) an LC CDR1 comprising the amino acid sequence of SEQ ID NO: 24, (ii) an LC CDR2 comprising the amino acid sequence of SEQ ID NO: 25, and (iii) an LC CDR3 comprising the amino acid sequence of SEQ ID NO: 26.

Clause 32. A method for selecting whether to enroll a subject in a clinical trial for frontotemporal lobar degeneration with TAR DNA-binding protein 43 inclusions (FTLD-TDP), comprising: (a) measuring expression levels of TAR DNA-binding protein 43 (TDP-43; SEQ ID NO: 1) in a sample from the subject, wherein the measuring comprises contacting the sample with an antibody or antigen-binding fragment thereof, wherein the antibody or antigen-binding fragment comprises an immunoglobulin heavy chain (HC) variable domain sequence and an immunoglobulin light chain (LC) variable domain sequence, wherein: (a1) the immunoglobulin HC variable domain sequence comprises (a1a) an HC CDR1 comprising the amino acid sequence of SEQ ID NO: 4, (a1b) an HC CDR2 comprising the amino acid sequence of SEQ ID NO: 5, and (a1c) an HC CDR3 comprising the amino acid sequence of SEQ ID NO: 6; and (a2) the immunoglobulin LC variable domain sequence comprises (a2a) an LC CDR1 comprising the amino acid sequence of SEQ ID NO: 8, (a2b) an LC CDR2 comprising the amino acid sequence of SEQ ID NO: 9, and (a2c) an LC CDR3 comprising the amino acid sequence of SEQ ID NO: 10; (b) comparing the expression levels of the TDP-43 to a threshold expression level; and, wherein: (b1) if the expression levels of TDP-43 are above the threshold expression level, the subject is selected for the clinical trial; or, (b2) if the expression levels of TDP-43 are below the threshold expression level, the subject is not selected for the clinical trial.

Clause 33. The method of clause 32, wherein the measuring further comprises contacting the sample with a second antibody or antigen-binding fragment thereof, wherein the second antibody or antigen-binding fragment comprises an immunoglobulin HC variable domain sequence and an immunoglobulin LC variable domain sequence, wherein: (a) the immunoglobulin HC variable domain sequence comprises (i) an HC CDR 1 comprising the amino acid sequence of SEQ ID NO: 12, (ii) an HC CDR2 comprising the amino acid sequence of SEQ ID NO: 13, and (iii) an HC CDR3 comprising the amino acid sequence of SEQ ID NO: 14; and (b) the immunoglobulin LC variable domain sequence comprises (i) an LC CDR1 comprising the amino acid sequence of SEQ ID NO: 16, (ii) an LC CDR2 comprising the amino acid sequence of SEQ ID NO: 17, and (iii) an LC CDR3 comprising the amino acid sequence of SEQ ID NO: 18.

Clause 34. The method of clause 32, wherein the measuring further comprises contacting the sample with a second antibody or antigen-binding fragment thereof, wherein the second antibody or antigen-binding fragment comprises an immunoglobulin HC variable domain sequence and an immunoglobulin LC variable domain sequence, wherein: (a) the immunoglobulin HC variable domain sequence comprises (i) an HC CDR1 comprising the amino acid sequence of SEQ ID NO: 20, (ii) an HC CDR2 comprising the amino acid sequence of SEQ ID NO: 21, and (iii) an HC CDR3 comprising the amino acid sequence of SEQ ID NO: 22; and (b) the immunoglobulin LC variable domain sequence comprises (i) an LC CDR1 comprising the amino acid sequence of SEQ ID NO: 24, (ii) an LC CDR2 comprising the amino acid sequence of SEQ ID NO: 25, and (iii) an LC CDR3 comprising the amino acid sequence of SEQ ID NO: 26.

```
SEQUENCES
TDP-43 Full length
                                    SEQ ID NO: 1
MSEYIRVTEDENDEPIEIPSEDDGTVLLSTVTAQFPGACG

LRYRNPVSQCMRGVRLVEGILHAPDAGWGNLVYVVNYPKD

NKRKMDETDASSAVKVKRAVQKTSDLIVLGLPWKTTEQDL

KEYFSTFGEVLMVQVKKDLKTGHSKGFGFVRFTEYETQVK

VMSQRHMIDGRWCDCKLPNSKQSQDEPLRSRKVFVGRCTE

DMTEDELREFFSQYGDVMDVFIPKPFRAFAFVTFADDQIA

QSLCGEDLIIKGISVHISNAEPKHNSNRQLERSGRFGGNP

GGFGNQGGFGNSRGGGAGLGNNQGSNMGGGMNFGAFSINP

AMMAAAQAALQSSWGMMGMLASQQNQSGPSGNNQNQGNMQ

REPNQAFGSGNNSYSGSNSGAAIGWGSASNAGSGSGFNGG

FGSSMDSKSSGWGMNH

260 AA-360 AA of TDP-43
                                    SEQ ID NO: 2
AEPKHNSNRQLERSGRFGGNPGGFGNQGGFGNSRGGGAGL

GNNQGSNMGGGMNFGAFSINPAMMAAAQAALQSSWGMMGM

LASQQNQSGPSGNNQNQGNMQ

Heavy chain variable domain (VH) amino
acid sequence of anti-TDP-43 antibody
MAb#9
                                    SEQ ID NO: 3
QVQLGESGPELKKPGETVKISCKASGDTFTANTMHWVKQS

PGRGFKSLEWIDTSYSGETRAHDFGGRFAFSLETSQSTAY

LQMQNLKTEDTAIYFCVRGLADYWGQGTKVTVSS

VH complementarity-determining region
(CDR)1 amino acid sequence of anti-
TDP-43 antibody
MAb#9
                                    SEQ ID NO: 4
ANTMH VH CDR2 amino acid sequence of anti-
TDP-43 antibody MAb#9
                                    SEQ ID NO: 5
WIDTSYSGETRAHDFGG VH CDR3 amino acid sequence of anti-
TDP-43 antibody MAb#9
```

VL CDR1 amino acid sequence of anti-
TDP-43 antibody MAb#4
                                                     SEQ ID NO: 16
KSTNSHLRTEGILYLR

SEQ ID NO: 6
GLADY

Light chain variable domain (VL) amino
acid sequence of
anti-TDP-43 antibody MAb#9
                                                SEQ ID NO: 7
DIELTQSPLTLSVSAGQSVTISCRTSQSIVHSNGATYLEW

YLQRPGYSPKLLIYLVSNDFSGVPHRFTGTGSGTDFTLQI

SRVEARDLGIYYCFQASYFPYTFGGGTRLEIKR

VL CDR1 amino acid sequence of anti-
TDP-43 antibody MAb#9
                                                SEQ ID NO: 8
RTSQSIVHSNGATYLE VL CDR2 amino acid sequence of anti-
TDP-43 antibody MAb#9
                                                SEQ ID NO: 9
LVSNDFS VL CDR3 amino acid sequence of anti-
TDP-43 antibody MAb#9
                                                SEQ ID NO: 10
FQASYFPYT Heavy chain variable domain (VH) amino
acid sequence of anti-TDP-43 antibody MAb#4
                                                SEQ ID NO: 11
QVQLVESGGGLVKPGGSLKLSCATSGFTFTAYETMWVRQP

PGKALEWIDFISYSRNETGETRAIEFGGRFTISRDSSQSI

LYLQMNTLRGEDSATYYCARDRGLSAEDIYWGQGTKVTVS

S

VH CDR1 amino acid sequence of anti-
TDP-43 antibody MAb#4
                                                SEQ ID NO: 12
AYETM VH CDR2 amino acid sequence of anti-
TDP-43 antibody MAb#4
                                                SEQ ID NO: 13
WIDFISYSRNETGETRAIEFGG VH CDR3 amino acid sequence of anti-
TDP-43 antibody MAb#4
                                                SEQ ID NO: 14
GLSAEDIY Light chain variable domain (VL) amino
acid sequence of
anti-TDP-43 antibody MAb#4
                                                SEQ ID NO: 15
DIELTQSPLTLSVTIGQSASISCKSTNSHLRTEGILYLRW

LLQRPGQSPKRLIYLVSIADSGVPDRFTGSGSGTDFTLKI

SRVEAEDLGVYYCAQSTRFPYTFGGGTRLEIKR

VL CDR2 amino acid sequence of anti-
TDP-43 antibody MAb#4
                                                SEQ ID NO: 17
LVSIADS VL CDR3 amino acid sequence of anti-
TDP-43 antibody MAb#4
                                                SEQ ID NO: 18
AQSTRFPYT Heavy chain variable domain (VH)
amino acid sequence of
anti-TDP-43 antibody MAb#5
                                                SEQ ID NO: 19
QVQLEQSGPELVQPGASVKISCKASGDSFTAQYMHWVKQS

HVKSLEWTGHIGPYEGSTPYNGNFKDKGSLTVDKSSSTAY

MELHSLTSEDSAVYYCARSSGLEIFKSWGQGTPVTVSS

VH CDR1 amino acid sequence of anti-
TDP-43 antibody MAb#5
                                                SEQ ID NO: 20
AQYMH VH CDR2 amino acid sequence of anti-
TDP-43 antibody MAb#5
                                                SEQ ID NO: 21
WTGHIGPYEGSTPYNG VH CDR3 amino acid sequence of anti-
TDP-43 antibody MAb#5
                                                SEQ ID NO: 22
GLEIFKS Light chain variable domain (VL) amino
acid sequence of
anti-TDP-43 antibody MAb#5
                                                SEQ ID NO: 23
DILMTQSPASLAVSLGQRATISCRESQSIVESKGNTYLEW

YLQKPGKAPKLLIYEVTNHFSGVPSRFSGSRSGTDFTLTI

SSLQPEDFGIYYCFQESNTPYTFGQGTKLEIKR

VL CDR1 amino acid sequence of anti-
TDP-43 antibody MAb#5
                                                SEQ ID NO: 24
RESQSIVESKGNTYLE VL CDR2 amino acid sequence of anti-
TDP-43 antibody MAb#5
                                                SEQ ID NO: 25
EVTNHFS VL CDR3 amino acid sequence of anti-
TDP-43 antibody MAb#5
                                                SEQ ID NO: 26
FQESNTPYT

---

SEQUENCE LISTING

Sequence total quantity: 26
SEQ ID NO: 1          moltype = AA  length = 416
FEATURE               Location/Qualifiers
source                1..416
                      mol_type = protein
                      organism = synthetic construct
SEQUENCE: 1
MSEYIRVTED ENDEPIEIPS EDDGTVLLST VTAQFPGACG LRYRNPVSQC MRGVRLVEGI   60
LHAPDAGWGN LVYVVNYPKD NKRKMDETDA SSAVKVKRAV QKTSDLIVLG LPWKTTEQDL  120
KEYFSTFGEV LMVQVKKDLK TGHSKGFGFV RFTEYETQVK VMSQRHMIDG RWCDCKLPNS  180

```
KQSQDEPLRS RKVFVGRCTE DMTEDELREF FSQYGDVMDV FIPKPFRAFA FVTFADDQIA  240
QSLCGEDLII KGISVHISNA EPKHNSNRQL ERSGRFGGNP GGFGNQGGFG NSRGGGAGLG  300
NNQGSNMGGG MNFGAFSINP AMMAAAQAAL QSSWGMMGML ASQQNQSGPS GNNQNQGNMQ  360
REPNQAFGSG NNSYSGSNSG AAIGWGSASN AGSGSGFNGG FGSSMDSKSS GWGMNH      416

SEQ ID NO: 2                moltype = AA   length = 101
FEATURE                     Location/Qualifiers
source                      1..101
                            mol_type = protein
                            organism = synthetic construct
SEQUENCE: 2
AEPKHNSNRQ LERSGRFGGN PGGFGNQGGF GNSRGGGAGL GNNQGSNMGG GMNFGAFSIN  60
PAMMAAAQAA LQSSWGMMGM LASQQNQSGP SGNNQNQGNM Q                      101

SEQ ID NO: 3                moltype = AA   length = 114
FEATURE                     Location/Qualifiers
source                      1..114
                            mol_type = protein
                            organism = synthetic construct
SEQUENCE: 3
QVQLGESGPE LKKPGETVKI SCKASGDTFT ANTMHWVKQS PGRGFKSLEW IDTSYSGETR  60
AHDFGGRFAF SLETSQSTAY LQMQNLKTED TAIYFCVRGL ADYWGQGTKV TVSS        114

SEQ ID NO: 4                moltype = AA   length = 7
FEATURE                     Location/Qualifiers
source                      1..7
                            mol_type = protein
                            organism = synthetic construct
SEQUENCE: 4
VHANTMH                                                            7

SEQ ID NO: 5                moltype = AA   length = 19
FEATURE                     Location/Qualifiers
source                      1..19
                            mol_type = protein
                            organism = synthetic construct
SEQUENCE: 5
VHWIDTSYSG ETRAHDFGG                                               19

SEQ ID NO: 6                moltype = AA   length = 7
FEATURE                     Location/Qualifiers
source                      1..7
                            mol_type = protein
                            organism = synthetic construct
SEQUENCE: 6
VHGLADY                                                            7

SEQ ID NO: 7                moltype = AA   length = 113
FEATURE                     Location/Qualifiers
source                      1..113
                            mol_type = protein
                            organism = synthetic construct
SEQUENCE: 7
DIELTQSPLT LSVSAGQSVT ISCRTSQSIV HSNGATYLEW YLQRPGYSPK LLIYLVSNDF  60
SGVPHRFTGT GSGTDFTLQI SRVEARDLGI YYCFQASYFP YTFGGGTRLE IKR         113

SEQ ID NO: 8                moltype = AA   length = 18
FEATURE                     Location/Qualifiers
source                      1..18
                            mol_type = protein
                            organism = synthetic construct
SEQUENCE: 8
VLRTSQSIVH SNGATYLE                                                18

SEQ ID NO: 9                moltype = AA   length = 9
FEATURE                     Location/Qualifiers
source                      1..9
                            mol_type = protein
                            organism = synthetic construct
SEQUENCE: 9
VLLVSNDFS                                                          9

SEQ ID NO: 10               moltype = AA   length = 11
FEATURE                     Location/Qualifiers
source                      1..11
                            mol_type = protein
                            organism = synthetic construct
SEQUENCE: 10
VLFQASYFPY T                                                       11
```

-continued

```
SEQ ID NO: 11              moltype = AA  length = 121
FEATURE                    Location/Qualifiers
source                     1..121
                           mol_type = protein
                           organism = synthetic construct
SEQUENCE: 11
QVQLVESGGG LVKPGGSLKL SCATSGFTFT AYETMWVRQP PGKALEWIDF ISYSRNETGE   60
TRAIEFGGRF TISRDSSQSI LYLQMNTLRG EDSATYYCAR DRGLSAEDIY WGQGTKVTVS   120
S                                                                   121

SEQ ID NO: 12              moltype = AA  length = 5
FEATURE                    Location/Qualifiers
source                     1..5
                           mol_type = protein
                           organism = synthetic construct
SEQUENCE: 12
AYETM                                                               5

SEQ ID NO: 13              moltype = AA  length = 22
FEATURE                    Location/Qualifiers
source                     1..22
                           mol_type = protein
                           organism = synthetic construct
SEQUENCE: 13
WIDFISYSRN ETGETRAIEF GG                                            22

SEQ ID NO: 14              moltype = AA  length = 8
FEATURE                    Location/Qualifiers
source                     1..8
                           mol_type = protein
                           organism = synthetic construct
SEQUENCE: 14
GLSAEDIY                                                            8

SEQ ID NO: 15              moltype = AA  length = 113
FEATURE                    Location/Qualifiers
source                     1..113
                           mol_type = protein
                           organism = synthetic construct
SEQUENCE: 15
DIELTQSPLT LSVTIGQSAS ISCKSTNSHL RTEGILYLRW LLQRPGQSPK RLIYLVSIAD   60
SGVPDRFTGS GSGTDFTLKI SRVEAEDLGV YYCAQSTRFP YTFGGGTRLE IKR          113

SEQ ID NO: 16              moltype = AA  length = 16
FEATURE                    Location/Qualifiers
source                     1..16
                           mol_type = protein
                           organism = unidentified
SEQUENCE: 16
KSTNSHLRTE GILYLR                                                   16

SEQ ID NO: 17              moltype = AA  length = 7
FEATURE                    Location/Qualifiers
source                     1..7
                           mol_type = protein
                           organism = synthetic construct
SEQUENCE: 17
LVSIADS                                                             7

SEQ ID NO: 18              moltype = AA  length = 9
FEATURE                    Location/Qualifiers
source                     1..9
                           mol_type = protein
                           organism = synthetic construct
SEQUENCE: 18
AQSTRFPYT                                                           9

SEQ ID NO: 19              moltype = AA  length = 118
FEATURE                    Location/Qualifiers
source                     1..118
                           mol_type = protein
                           organism = synthetic construct
SEQUENCE: 19
QVQLEQSGPE LVQPGASVKI SCKASGDSFT AQYMHWVKQS HVKSLEWTGH IGPYEGSTPY   60
NGNFKDKGSL TVDKSSSTAY MELHSLTSED SAVYYCARSS GLEIFKSWGQ GTPVTVSS     118

SEQ ID NO: 20              moltype = AA  length = 5
FEATURE                    Location/Qualifiers
```

-continued

```
source                  1..5
                        mol_type = protein
                        organism = synthetic construct
SEQUENCE: 20
AQYMH                                                               5

SEQ ID NO: 21           moltype = AA  length = 16
FEATURE                 Location/Qualifiers
source                  1..16
                        mol_type = protein
                        organism = synthetic construct
SEQUENCE: 21
WTGHIGPYEG STPYNG                                                   16

SEQ ID NO: 22           moltype = AA  length = 7
FEATURE                 Location/Qualifiers
source                  1..7
                        mol_type = protein
                        organism = synthetic construct
SEQUENCE: 22
GLEIFKS                                                             7

SEQ ID NO: 23           moltype = AA  length = 113
FEATURE                 Location/Qualifiers
source                  1..113
                        mol_type = protein
                        organism = synthetic construct
SEQUENCE: 23
DILMTQSPAS LAVSLGQRAT ISCRESQSIV ESKGNTYLEW YLQKPGKAPK LLIYEVTNHF   60
SGVPSRFSGS RSGTDFTLTI SSLQPEDFGI YYCFQESNTP YTFGQGTKLE IKR          113

SEQ ID NO: 24           moltype = AA  length = 16
FEATURE                 Location/Qualifiers
source                  1..16
                        mol_type = protein
                        organism = synthetic construct
SEQUENCE: 24
RESQSIVESK GNTYLE                                                   16

SEQ ID NO: 25           moltype = AA  length = 7
FEATURE                 Location/Qualifiers
source                  1..7
                        mol_type = protein
                        organism = synthetic construct
SEQUENCE: 25
EVTNHFS                                                             7

SEQ ID NO: 26           moltype = AA  length = 9
FEATURE                 Location/Qualifiers
source                  1..9
                        mol_type = protein
                        organism = synthetic construct
SEQUENCE: 26
FQESNTPYT                                                           9
```

The invention claimed is:

1. An antibody or antigen-binding fragment thereof comprising an immunoglobulin heavy chain (HC) variable domain sequence and an immunoglobulin light chain (LC) variable domain sequence, wherein:

(a) the immunoglobulin HC variable domain sequence comprises (i) an HC CDR1 comprising the amino acid sequence of SEQ ID NO: 4, (ii) an HC CDR2 comprising the amino acid sequence of SEQ ID NO: 5, and (iii) an HC CDR3 comprising the amino acid sequence of SEQ ID NO: 6; and (b) the immunoglobulin LC variable domain sequence comprises (i) an LC CDR1 comprising the amino acid sequence of SEQ ID NO: 8, (ii) an LC CDR2 comprising the amino acid sequence of SEQ ID NO: 9, and (iii) an LC CDR3 comprising the amino acid sequence of SEQ ID NO: 10.

2. The antibody or antigen-binding fragment thereof of claim 1, wherein the immunoglobulin HC variable domain sequence comprises the amino acid sequence of SEQ ID NO: 3; and the immunoglobulin LC variable domain sequence comprises the amino acid sequence of SEQ ID NO: 7.

3. An immunoassay kit comprising one or more of the antibodies or antigen-binding fragments thereof of claim 1.

4. An immunoassay kit for selectively detecting TAR DNA-binding protein 43 (TDP-43; SEQ ID NO: 1) in a biological sample, the kit comprising:

an antibody or antigen-binding fragment thereof, wherein the antibody or antigen-binding fragment comprises an immunoglobulin heavy chain (HC) variable domain sequence and an immunoglobulin light chain (LC) variable domain sequence, wherein:

(a) the immunoglobulin HC variable domain sequence comprises (i) an HC CDR1 comprising the amino acid sequence of SEQ ID NO: 4, (ii) an HC CDR2 comprising the amino acid sequence of SEQ ID NO: 5, and (iii) an HC CDR3 comprising the amino acid sequence of SEQ ID NO: 6; and (b) the immunoglobulin LC variable domain sequence comprises (i) an LC CDR1 comprising the amino acid sequence of SEQ ID NO: 8, (ii) an LC CDR2 comprising the amino acid sequence of SEQ ID NO: 9, and (iii) an LC CDR3 comprising the amino acid sequence of SEQ ID NO: 10; and, a detection reagent.

5. The kit of claim 4, further comprising a solid support for the antibody or antigen-binding fragment thereof.

6. The kit of claim 4, wherein the detection reagent is one or more of colorimetric substrates, chemiluminescent substrates, and fluorescent substrates.

7. The kit of claim 4, further comprising a second antibody or antigen-binding fragment thereof, wherein the second antibody or antigen-binding fragment comprises an immunoglobulin HC variable domain sequence and an immunoglobulin LC variable domain sequence, wherein:

(a) the immunoglobulin HC variable domain sequence comprises (i) an HC CDR1 comprising the amino acid sequence of SEQ ID NO: 12, (ii) an HC CDR2 comprising the amino acid sequence of SEQ ID NO: 13, and (iii) an HC CDR3 comprising the amino acid sequence of SEQ ID NO: 14; and (b) the immunoglobulin LC variable domain sequence comprises (i) an LC CDR1 comprising the amino acid sequence of SEQ ID NO: 16, (ii) an LC CDR2 comprising the amino acid sequence of SEQ ID NO: 17, and (iii) an LC CDR3 comprising the amino acid sequence of SEQ ID NO: 18.

8. The kit of claim 4, further comprising a second antibody or antigen-binding fragment thereof, wherein the second antibody or antigen-binding fragment comprises an immunoglobulin HC variable domain sequence and an immunoglobulin LC variable domain sequence, wherein:

(a) the immunoglobulin HC variable domain sequence comprises (i) an HC CDR1 comprising the amino acid sequence of SEQ ID NO: 20, (ii) an HC CDR2 comprising the amino acid sequence of SEQ ID NO: 21, and (iii) an HC CDR3 comprising the amino acid sequence of SEQ ID NO: 22; and (b) the immunoglobulin LC variable domain sequence comprises (i) an LC CDR1 comprising the amino acid sequence of SEQ ID NO: 24, (ii) an LC CDR2 comprising the amino acid sequence of SEQ ID NO: 25, and (iii) an LC CDR3 comprising the amino acid sequence of SEQ ID NO: 26.

* * * * *